(12) United States Patent
Shaaltiel et al.

(10) Patent No.: US 8,741,620 B2
(45) Date of Patent: Jun. 3, 2014

(54) HUMAN LYSOSOMAL PROTEINS FROM PLANT CELL CULTURE

(75) Inventors: Yoseph Shaaltiel, Kibbutz HaSolelim (IL); Gideon Baum, Kibbutz Ayelet HaShachar (IL); Daniel Bartfeld, Kibbutz Moran (IL); Sharon Hashmueli, Ramot-Naftali (IL); Ayala Lewkowicz, Kfar-Vradim (IL)

(73) Assignee: Protalix Ltd., Carmiel (IL)

( * ) Notice: Subject to any disclaimer, the term of this patent is extended or adjusted under 35 U.S.C. 154(b) by 0 days.

(21) Appl. No.: 13/555,243

(22) Filed: Jul. 23, 2012

(65) Prior Publication Data

US 2012/0282231 A1 Nov. 8, 2012

Related U.S. Application Data

(60) Division of application No. 13/080,692, filed on Apr. 6, 2011, now Pat. No. 8,227,230, which is a division of application No. 11/790,991, filed on Apr. 30, 2007, now Pat. No. 7,951,557, which is a continuation-in-part of application No. 10/554,387, filed as application No. PCT/IL2004/000181 on Feb. 24, 2004, now abandoned.

(30) Foreign Application Priority Data

Apr. 27, 2003 (IL) .......................................... 155588

(51) Int. Cl.
*C12N 9/00* (2006.01)
*C12N 9/42* (2006.01)
*C12N 1/20* (2006.01)
*C12N 15/00* (2006.01)
*C07H 21/04* (2006.01)

(52) U.S. Cl.
USPC ..... 435/209; 435/183; 435/252.3; 435/320.1; 536/23.1

(58) Field of Classification Search
None
See application file for complete search history.

(56) References Cited

U.S. PATENT DOCUMENTS

| | | |
|---|---|---|
| 467,993 A | 2/1892 | Jorgensen et al. |
| 2,147,271 A | 2/1939 | Schwarz et al. |
| 2,341,259 A | 2/1944 | Baldwin |
| 2,836,434 A | 5/1958 | Heden |
| 3,201,327 A | 8/1965 | Beck |
| 3,468,520 A | 9/1969 | Duryea et al. |
| 3,504,185 A | 3/1970 | Zweig et al. |
| 3,540,700 A | 11/1970 | Freedman et al. |
| 3,705,082 A | 12/1972 | Hondermarck et al. |
| 3,743,582 A | 7/1973 | Kitai et al. |
| 3,793,154 A | 2/1974 | Efthymiou |
| 3,806,423 A | 4/1974 | Karrenbauer et al. |
| 3,950,227 A | 4/1976 | Efthymiou |
| 4,179,339 A | 12/1979 | Sogi et al. |
| 4,228,243 A | 10/1980 | Iizuka |
| 4,328,317 A | 5/1982 | Prentice et al. |
| 4,491,549 A | 1/1985 | Fischer et al. |
| 4,519,984 A | 5/1985 | Hitzman |
| 4,668,632 A | 5/1987 | Young et al. |
| 4,708,938 A | 11/1987 | Hickinbotham |
| 4,713,345 A | 12/1987 | Ramsden |
| 4,717,668 A | 1/1988 | Keilman et al. |
| 4,725,548 A | 2/1988 | Karrer |
| 4,888,294 A | 12/1989 | Van Wezel et al. |
| 4,908,315 A | 3/1990 | Kertz |
| 4,931,401 A | 6/1990 | Safi |
| 5,043,283 A | 8/1991 | Endo et al. |
| 5,073,491 A | 12/1991 | Familletti |
| 5,081,036 A | 1/1992 | Familletti |
| 5,100,801 A | 3/1992 | Ward et al. |
| 5,166,072 A | 11/1992 | Krauling et al. |
| 5,188,946 A | 2/1993 | Ward et al. |
| 5,225,346 A | 7/1993 | Matsumiya et al. |
| 5,240,598 A | 8/1993 | Portier et al. |
| 5,246,855 A | 9/1993 | Katinger et al. |
| 5,267,791 A | 12/1993 | Christian et al. |
| 5,342,781 A | 8/1994 | Su |
| 5,367,110 A | 11/1994 | Galili |
| 5,372,945 A | 12/1994 | Alchas et al. |
| 5,409,833 A | 4/1995 | Hu et al. |
| 5,534,417 A | 7/1996 | Arad et al. |
| 5,549,892 A | 8/1996 | Friedman et al. |
| 5,565,015 A | 10/1996 | Kobayashi |

(Continued)

FOREIGN PATENT DOCUMENTS

| | | |
|---|---|---|
| CN | 1875111 | 12/2006 |
| DE | 2654725 | 8/1977 |

(Continued)

OTHER PUBLICATIONS

Accession AAW07885. Jan. 28, 1997.*

(Continued)

*Primary Examiner* — Christian Fronda

(57) ABSTRACT

A device, system and method for producing glycosylated proteins in plant culture, particularly proteins having a high mannose glycosylation, while targeting such proteins with an ER signal and/or by-passing the Golgi. The invention further relates to vectors and methods for expression and production of enzymatically active high mannose lysosomal enzymes using transgenic plant root, particularly carrot cells. More particularly, the invention relates to host cells, particularly transgenic suspended carrot cells, vectors and methods for high yield expression and production of biologically active high mannose Glucocerebrosidase (GCD). The invention further provides for compositions and methods for the treatment of lysosomal storage diseases.

6 Claims, 21 Drawing Sheets
(13 of 21 Drawing Sheet(s) Filed in Color)

(56) References Cited

U.S. PATENT DOCUMENTS

| | | | |
|---|---|---|---|
| 5,612,188 | A | 3/1997 | Shuler et al. |
| 5,929,304 | A | 7/1999 | Radin et al. |
| 6,054,637 | A | 4/2000 | Boller et al. |
| 6,083,725 | A | 7/2000 | Selden et al. |
| 6,096,546 | A | 8/2000 | Raskin |
| 6,190,913 | B1 | 2/2001 | Singh |
| 6,194,560 | B1 | 2/2001 | Arntzen et al. |
| 6,210,166 | B1 | 4/2001 | Jenkins et al. |
| 6,391,638 | B1 | 5/2002 | Shaaltiel |
| 6,432,698 | B1 | 8/2002 | Gaugler et al. |
| 6,709,862 | B2 | 3/2004 | Curtis |
| 6,815,184 | B2 | 11/2004 | Stomp et al. |
| 6,846,968 | B1 | 1/2005 | Erwin et al. |
| 7,655,781 | B2 | 2/2010 | Shemesh et al. |
| 7,951,557 | B2 | 5/2011 | Shaaltiel et al. |
| 2002/0015708 | A1 | 2/2002 | Stram et al. |
| 2002/0088024 | A1 | 7/2002 | Garger et al. |
| 2002/0110915 | A1 | 8/2002 | Shaaltiel |
| 2002/0127219 | A1 | 9/2002 | Okkels et al. |
| 2003/0077806 | A1 | 4/2003 | Selden et al. |
| 2005/0032211 | A1 | 2/2005 | Shaaltiel |
| 2005/0272146 | A1 | 12/2005 | Hodge et al. |
| 2005/0281805 | A1 | 12/2005 | LeBowitz et al. |
| 2005/0282269 | A1 | 12/2005 | Proulx |
| 2006/0204487 | A1 | 9/2006 | Shaaltiel et al. |
| 2008/0038232 | A1 | 2/2008 | Shaaltiel et al. |
| 2008/0132743 | A1 | 6/2008 | Mack et al. |
| 2009/0053743 | A1 | 2/2009 | Link et al. |
| 2009/0053762 | A1 | 2/2009 | Shaaltiel |
| 2009/0082548 | A1 | 3/2009 | Shaaltiel et al. |
| 2009/0208477 | A1 | 8/2009 | Shaaltiel et al. |
| 2010/0112700 | A1 | 5/2010 | Shaaltiel et al. |
| 2010/0136673 | A1 | 6/2010 | Shaaltiel |
| 2011/0250181 | A1 | 10/2011 | Shaaltiel et al. |

FOREIGN PATENT DOCUMENTS

| | | |
|---|---|---|
| DE | 69718812 | 1/2003 |
| EP | 0200792 | 12/1986 |
| EP | 0343885 | 11/1989 |
| EP | 0350723 | 1/1990 |
| EP | 0447256 | 9/1991 |
| EP | 0462065 | 12/1991 |
| EP | 0713966 | 5/1996 |
| EP | 0938544 | 1/2003 |
| GB | 1053848 | 1/1967 |
| GB | 2202549 | 9/1988 |
| JP | 63-109772 | 5/1988 |
| JP | 02-119771 | 5/1990 |
| JP | 4-229182 | 8/1992 |
| JP | 08-503615 | 4/1996 |
| JP | 10-084802 | 4/1998 |
| JP | 10-507916 | 8/1998 |
| JP | 11-012143 | 1/1999 |
| JP | 2000-053549 | 2/2000 |
| JP | 2000-128752 | 5/2000 |
| JP | 2001-502526 | 2/2001 |
| JP | 2002-238580 | 8/2002 |
| JP | 2002-526116 | 8/2002 |
| JP | 2003-180354 | 7/2003 |
| JP | 2007-511231 | 5/2007 |
| NL | 1012782 | 4/2001 |
| WO | WO 88/00234 | 1/1988 |
| WO | WO 94/12628 | 6/1994 |
| WO | WO 96/12801 | 5/1996 |
| WO | WO 96/13599 | 5/1996 |
| WO | WO 97/10353 | 3/1997 |
| WO | WO 98/13469 | 4/1998 |
| WO | WO 99/07210 | 2/1999 |
| WO | WO 00/20612 | 4/2000 |
| WO | WO 02/08404 | 1/2002 |
| WO | WO 02/15927 | 2/2002 |
| WO | WO 02/40686 | 5/2002 |
| WO | WO 02/68666 | 6/2002 |
| WO | WO 02/083888 | 10/2002 |
| WO | WO 03/013598 | 2/2003 |
| WO | WO 2004/003207 | 1/2004 |
| WO | WO 2004/005480 | 1/2004 |
| WO | WO 2004/096978 | 11/2004 |
| WO | WO 2005/049784 | 6/2005 |
| WO | WO 2005/080544 | 9/2005 |
| WO | WO 2006/038209 | 4/2006 |
| WO | WO 2007/005882 | 1/2007 |
| WO | WO 2008/132743 | 11/2008 |
| WO | WO 2008/135991 | 11/2008 |

OTHER PUBLICATIONS

Accession AAR15823. Mar. 19, 1992.*
Schueler et al. Neurochem Res. Apr. 2002;27(4):325-30, Abstract.*
Office Action Dated Dec. 3, 2012 From the Israeli Patent Office Re.: Application No. 182888 and Its Translation Into English.
Examination Report Dated Feb. 8, 2013 From the Government of India, Patent Office, Intellectual Property Building Re. Application No. 930/CHENP/2008.
Summons to Attend Oral Proceedings Pursuant to Rule 115(1) EPC Dated Feb. 14, 2013 From the European Patent Office Re. Application No. 10012376.9.
Translation of Notice of the Reason for Rejection Dated Feb. 27, 2013 From the Korean Intellectual Property Office Re. Application No. 2005-7020434.
Translation of Office Action Dated Jan. 25, 2013 From the State Intellectual Property Office of the People's Republic of China Re. Application No. 201110112706.3.
Translation of Search Report Dated Jan. 25, 2013 From the State Intellectual Property Office of the People's Republic of China Re. Application No. 201110112706.3.
Communication Pursuant to Article 94(3) EPC Dated May 10, 2012 From the European Patent Office Re. Application No. 10012374.4.
Communication Pursuant to Article 94(3) EPC Dated Feb. 12, 2009 From the European Patent Office Re.: Application No. 04713966.2.
Communication Pursuant to Article 94(3) EPC Dated Jan. 20, 2012 From the European Patent Office Re. Application No. 10012376.9.
Communication Pursuant to Article 94(3) EPC Dated Jan. 30, 2012 From the European Patent Office Re. Application No. 10012372.8.
Communication Pursuant to Article 96(2) EPC Dated Oct. 5, 2011 From the European Patent Office Re.: Application No. 08738278.4.
Communication Pursuant to Article 96(2) EPC Dated Oct. 31, 2007 From the European Patent Office Re.: Application No. 04713966.2.
Communication Pursuant to Rules 70(2) and 70a(2) EPC and Reference to Rule 39(1) EPC Dated Jul. 19, 2011 From the European Patent Office Re. Application No. 10012373.6.
Communication Under Rule 71(3) EPC Dated Dec. 1, 2011 From the European Patent Office Re.: Application No. 04713966.2.
European Search Report and the European Search Opinion Dated Apr. 1, 2011 From the European Patent Office Re. Application No. 10012375.1.
European Search Report and the European Search Opinion Dated Apr. 5, 2011 From the European Patent Office Re. Application No. 10012374.4.
European Search Report and the European Search Opinion Dated Apr. 8, 2011 From the European Patent Office Re. Application No. 10012372.8.
European Search Report and the European Search Opinion Dated Apr. 8, 2011 From the European Patent Office Re. Application No. 10012376.9.
European Search Report and the European Search Opinion Dated May 27, 2011 From the European Patent Office Re. Application No. 10012373.6.
Examination Report Dated Aug. 2, 2011 From the Government of India, Patent Office, Intellectual Property Building Re.: Application No. 3478/CHENP/2006.
Examination Report Dated Sep. 5, 2011 From the Instituto Mexicano de la Propriedad Industrial Re. Application No. MX/a/2009/011751 and Its Summary in English.
Examination Report Dated Apr. 7, 2011 From the Instituto Mexicano de la Propriedad Industrial Re. Application No. PA/a/2005/011507.

(56) References Cited

OTHER PUBLICATIONS

Examination Report Dated Aug. 12, 2005 From the Government of India, Patent Office Re.: Application No. 631/del/2001.
Examination Report Dated Jan. 12, 2012 From the Federal Institute of Industrial Property of the Federal Service for Intellectual Property, Patents and Trademark of the Russian Federation Re. Application No. 2009143751 and Its Summary in English.
Examination Report Dated Jun. 12, 2007 From the Government of India, Patent Office Re.: Application No. 3150/CHENP/2005.
Examination Report Dated Sep. 12, 2011 From the Instituto Mexicano de la Propriedad Industrial Re. Application No. PA/a/2005/011507.
Examination Report Dated Sep. 13, 2011 From the Intellectual Property Office of Singapore, Issued by the Hungarian Patent Office on Aug. 25, 2011 Re. Application No. 200907212-5.
Examination Report Dated Jun. 18, 2010 From the Instituto Mexicano de la Propriedad Industrial Re.: Application No. PA/a/2006/009612.
Examination Report Dated Jun. 24, 2011 From the Government of India, Patent Office, Intellectual Property Building Re. Application No. 930/CHENP/2008.
Examination Report Dated Sep. 25, 2009 From the Instituto Mexicano de la Propriedad Industrial Re.: Application No. PA/a/2006/009612.
Examination Report Dated Aug. 31, 2009 From the Australian Government, IP Australia Re.: Application No. 2005214181.
Examination Request Dated Aug. 16, 2007 to the Australian Government, IP Australia Re.: Application No. 2005214181.
Examiner's Report Dated Dec. 1, 2008 From the Australian Government, IP Australia Re.: Application No. 2004234635.
Examiner's Report Dated Jan. 5, 2010 From the Australian Patent Office Re.: Application No. 2004234635.
Examiner's Report Dated Jan. 18, 2010 From the Australian Government, IP Australia Re. Application No. 2007201909.
Formal Examination Dated Jan. 26, 2010 From the ROSPATENT, Federal State Office, Federal Institution of Industrial Property of the Federal Office of Intellectual Property, Patents and Trademarks of the Russian Federation Re.: Application No. 2009148012 and Its Summary Into English.
International Preliminary Report on Patentability Dated Apr. 12, 2007 From the International Preliminary Examining Authority Re.: Application No. PCT/IL04/00181.
International Preliminary Report on Patentability Dated Nov. 19, 2009 From the International Bureau of WIPO Re.: Application No. PCT/IL2008/000614.
International Preliminary Report on Patentability Dated Apr. 21, 2006 From the International Preliminary Examining Authority Re.: Application No. PCT/IL2005/000228.
International Preliminary Report on Patentability Dated Mar. 23, 2006 From the International Bureau of WIPO Re.: Application No. PCT/IL2004/000181.
International Preliminary Report on Patentability Dated Apr. 29, 2010 From the International Bureau of WIPO Re.: Application No. PCT/IL2008/000576.
International Search Report and the Written Opinion Dated Apr. 9, 2010 From the International Searching Authority Re.: Application No. PCT/IL08/00576.
International Search Report and the Written Opinion Dated Dec. 15, 2005 From the International Searching Authority Re.: Application No. PCT/IL2005/000228.
International Search Report Dated Feb. 17, 2006 From the International Searching Authority Re.: Application No. PCT/IL04/00181.
International Search Report Dated May 27, 2009 From the International Searching Authority Re.: Application No. PCT/IL2008/000614.
Interview Summary Dated Apr. 7, 2011 From the US Patent and Trademark Office Re.: U.S. Appl. No. 12/385,894.
Invitation Pursuant to Article 94(3) and Rule 71(1) EPC Dated Jun. 17, 2011 From the European Patent Office Re.: Application No. 04713966.2.
Invitation Pursuant to Article 94(3) and Rule 71(1) EPC Dated Mar. 31, 2011 From the European Patent Office Re.: Application No. 04713966.2.
Invitation Pursuant to Rule 63(1) EPC Dated Mar. 25, 2011 From the European Patent Office Re. Application No. 10012373.6.
Notice of Acceptance Dated Dec. 8, 2010 From the South African Patent Office Re. Application No. 2009/07804.
Notice of Allowance Dated May 10, 2012 From the US Patent and Trademark Office Re. U.S. Appl. No. 13/080,692.
Notice of Allowance Dated May 20, 2011 From the Instituto Mexicano de la Propriedad Industrial Re.: Application No. PA/a/2006/009612.
Notice of Allowance of Oct. 16, 2009 From the US Patent and Trademark Office Re.: U.S. Appl. No. 10/554,387.
Notification of the Results of the Examination Dated Oct. 14, 2008 From the Patent Office of the Russian Federation Re.: Application No. 2005136874 and Its Translation Into English.
Office Action Dated Feb. 6, 2009 From the State Intellectual Property Office of the People's Republic of China Re.: Application No. 200480017916.2.
Office Action Dated Jan. 6, 2010 From the Israel Patent Office Re.: Application No. 177586 and Its Translation Into English.
Office Action Dated Jun. 9, 2011 From the US Patent and Trademark Office Re. U.S. Appl. No. 13/008,048.
Office Action Dated Dec. 10, 2008 From the Israeli Patent Office Re.: Application No. 171561 and Its Translation Into English.
Office Action Dated Jul. 15, 2010 From the Israel Patent Office Re.: Application No. 177586 and Its Translation Into English.
Office Action Dated Dec. 22, 2011 From the Israeli Patent Office Re.: Application No. 171561 and Its Translation Into English.
Office Action Dated Dec. 22, 2011 From the US Patent and Trademark Office Re. U.S. Appl. No. 13/008,048.
Office Action Dated Sep. 23, 2009 From the Israeli Patent Office Re.: Application No. 182888 and Its Translation Into English.
Office Action Dated Jul. 25, 2010 From the Israeli Patent Office Re.: Application No. 171561 and Its Translation Into English.
Office Action Dated Oct. 27, 2011 From the Israel Patent Office Re. Application No. 201799 and Its Translation Into English.
Office Action Dated Jun. 28, 2011 From the Israeli Patent Office Re.: Application No. 182888 and Its Translation Into English.
Office Letter Dated Jan. 14, 2008 From the Government of India, Patent Office Re.: Application No. 3150/CHENP/2005.
Official Action Dated Feb. 2, 2011 From the US Patent and Trademark Office Re.: U.S. Appl. No. 12/385,894.
Official Action Dated Apr. 5, 2012 From the US Patent and Trademark Office Re. U.S. Appl. No. 13/080,694.
Official Action Dated Apr. 6, 2010 From the US Patent and Trademark Office Re.: U.S. Appl. No. 11/979,813.
Official Action Dated Jun. 6, 2008 From the US Patent and Trademark Office Re.: U.S. Appl. No. 11/790,991.
Official Action Dated Apr. 8, 2009 From the US Patent and Trademark Office Re.: U.S. Appl. No. 10/554,387.
Official Action Dated Jan. 8, 2008 From the US Patent and Trademark Office Re.: U.S. Appl. No. 10/784,295.
Official Action Dated Mar. 8, 2010 From the US Patent and Trademark Office Re.: U.S. Appl. No. 11/790,991.
Official Action Dated Jan. 9, 2008 From the US Patent and Trademark Office Re.: U.S. Appl. No. 10/554,387.
Official Action Dated Mar. 9, 2010 From the US Patent and Trademark Office Re.: U.S. Appl. No. 12/385,894.
Official Action Dated Aug. 10, 2011 From the US Patent and Trademark Office Re. U.S. Appl. No. 10/554,387.
Official Action Dated Nov. 12, 2010 From the US Patent and Trademark Office Re. U.S. Appl. No. 12/690,977.
Official Action Dated Nov. 14, 2008 From the US Patent and Trademark Office Re.: U.S. Appl. No. 10/784,295.
Official Action Dated Oct. 14, 2009 From the Its Patent and Trademark Office Re.: U.S. Appl. No. 11/790,991.
Official Action Dated Jul. 16, 2012 From the US Patent and Trademark Office Re. U.S. Appl. No. 12/451,188.
Official Action Dated Aug. 17, 2010 From the US Patent and Trademark Office Re.: U.S. Appl. No. 11/979,813.

(56) References Cited

OTHER PUBLICATIONS

Official Action Dated Feb. 18, 2010 From the US Patent and Trademark Office Re.: U.S. Appl. No. 10/554,387.
Official Action Dated Jun. 18, 2007 From the US Patent and Trademark Office Re.: U.S. Appl. No. 10/784,295.
Official Action Dated Oct. 18, 2011 From ROSPATENT, Federal Government Institution, Federal Institute of Industrial Property of the Federal Service for Intellectual Property, Patents and Trademarks of the Russian Federation Re. Application No. 2009140906 and Its Summary in English.
Official Action Dated Jul. 20, 2012 From the US Patent and Trademark Office Re. U.S. Appl. No. 13/080,694.
Official Action Dated Jul. 21, 2008 From the US Patent and Trademark Office Re.: U.S. Appl. No. 10/554,387.
Official Action Dated Jun. 21, 2010 From the US Patent and Trademark Office Re.: U.S. Appl. No. 12/385,894.
Official Action Dated Jul. 22, 2009 From the US Patent and Trademark Office Re.: U.S. Appl. No. 10/784,295.
Official Action Dated Feb. 24, 2012 From the US Patent and Trademark Office Re. U.S. Appl. No. 13/080,692.
Official Action Dated Sep. 26, 2008 From the US Patent and Trademark Office Re.: U.S. Appl. No. 11/790,991.
Official Action Dated Jan. 29, 2008 From the US Patent and Trademark Office Re.: U.S. Appl. No. 11/790,991.
Official Action Dated Oct. 29, 2010 From the US Patent and Trademark Office Re.: U.S. Appl. No. 10/554,387.
Official Action Dated Oct. 31, 2008 From Patent Office of the Russian Federation Re.: 2007147328/15(051871).
Protocol Dated Jun. 17, 2009 From the Patent Office of the Russian Federation Re.: Application No. 2005136874 and a Summary in English.
Requisition by the Examiner Dated Aug. 3, 2006 From the Canadian Intellectual Property Office Re.: Application No. 2,266,851.
Requisition by the Examiner Dated Feb. 7, 2012 From the Canadian Intellectual Property Office Re. Application No. 2,523,539.
Requisition by the Examiner Dated Dec. 9, 2010 From the Canadian Intellectual Property Office Re. Application No. 2,523,539.
Requisition by the Examiner Dated May 31, 2011 From the Canadian Intellectual Property Office Re. Application No. 2,557,525.
Response Dated Dec. 1, 2010 to Notice of Reason for Rejection of Aug. 31, 2010 From the Japanese Patent Office Re. Application No. 2007-500352.
Response Dated Jan. 1, 2012 to European Search Report and the European Search Opinion of May 27, 2011 From the European Patent Office Re. Application No. 10012373.6.
Response Dated Jun. 1, 2011 to Requisition by the Examiner of Dec. 9, 2010 From the Canadian Intellectual Property Office Re. Application No. 2,523,539.
Response Dated Jun. 2, 2011 to Official Action of Feb. 2, 2011 From the US Patent and Trademark Office Re.: U.S. Appl. No. 12/385,894.
Response Dated Aug. 3, 2011 to Notice of Reason for Rejection of May 20, 2011 From the Japanese Patent Office Re. Application No. 2007-500352.
Response Dated Dec. 5, 2011 to European Search Report and the European Search Opinion of Apr. 5, 2011 From the European Patent Office Re. Application No. 10012374.4.
Response Dated Dec. 6, 2011 to European Search Report and the European Search Opinion of Apr. 1, 2011 From the European Patent Office Re. Application No. 10012375.1.
Response Dated Jul. 6, 2010 to Official Action of Apr. 6, 2010 From the US Patent and Trademark Office Re.: U.S. Appl. No. 11/979,813.
Response Dated Jun. 6, 2010 to Office Action of Jan. 6, 2010 From the Israel Patent Office Re.: Application No. 177586.
Response Dated Jul. 7, 2011 to Examination Report of Apr. 7, 2011 From the Instituto Mexicano de la Propriedad Industrial Re. Application No. PA/a/2005/011507.
Response Dated Jul. 7, 2011 to Written Opinion and Search Report Dated Feb. 11, 2011 From the Intellectual Property Office of Singapore Re. Application No. 200907212-5.
Response Dated Jul. 8, 2010 to Official Action of Mar. 8, 2010 From the US Patent and Trademark Office Re.: U.S. Appl. No. 11/790,991.
Response Dated Jun. 8, 2010 to Official Action of Mar. 9, 2010 From the US Patent and Trademark Office Re.: U.S. Appl. No. 12/385,894.
Response Dated Jan. 9, 2011 to Notice of Acceptance of Dec. 8, 2010 From the South African Patent Office Re. Application No. 2009/07804.
Response Dated Jun. 9, 2011 to the Notice of the Reason for Rejection of Mar. 12, 2011 From the Korean Intellectual Property Office Re. Application No. 2005-7020434.
Response Dated Nov. 10, 2011 to Notice of Reason for Rejection Dated Sep. 16, 2011 From the Japanese Patent Office Re. Application No. 2007-500352.
Response Dated Jul. 12, 2011 to Supplementary European Search Report and the European Search Opinion of Dec. 16, 2010 From the European Patent Office Re. Application No. 08738278.4.
Response Dated Apr. 13, 2011 to Notice of Reason for Rejection of Jan. 4, 2011 From the Japanese Patent Office Re.: Application No. 2006-507577.
Response Dated Jul. 13, 2010 to Official Action of Mar. 29, 2010 From ROSPATENT, Federal Government Institution, Federal Institute of Industrial Property of the Federal Service for Intellectual Property, Patents and Trademarks of the Russian Federation Re. Application No. 2009140906.
Response Dated Feb. 14, 2010 to Office Action of Nov. 6, 2009 From the State Intellectual Property Office of the People's Republic of China Re.: Application No. 200480017916.2.
Response Dated Feb. 14, 2011 to Examination Report of Jun. 18, 2010 From the Instituto Mexicano de la Propriedad Industrial Re.: Application No. PA/a/2006/009612.
Response Dated Feb. 15, 2011 to Examinees Report of Jan. 18, 2010 From the Australian Government, IP Australia Re. Application No. 2007201909.
Response Dated Nov. 15, 2010 to Office Action of Jul. 15, 2010 From the Israel Patent Office Re.: Application No. 177586.
Response Dated Nov. 16, 2011 to European Search Report and the European Search Opinion of Apr. 8, 2011 From the European Patent Office Re. Application No. 10012372.8.
Response Dated Aug. 17, 2010 to Official Action of Feb. 18, 2010 From the US Patent and Trademark Office Re.: U.S. Appl. No. 10/554,387.
Response Dated Nov. 17, 2010 to Written Opinion and Search Report of Jun. 18, 2010 Issued by the Hungarian Patent Office at May 13, 2010 From the Intellectual Property Office of Singapore Re. Application No. 200907212-5.
Response Dated Mar. 18, 2010 to Notice of Reason for Rejection of Dec. 4, 2009 From the Japanese Patent Office Re.: Application No. 2006-507577.
Response Dated Apr. 19, 2011 to Invitation Pursuant to Rule 63(1) EPC of Mar. 25, 2011 From the European Patent Office Re. Application No. 10012373.6.
Response Dated Dec. 20, 2010 to Written Opinion of Jun. 14, 2010 From the Intellectual Property Office of Singapore Re. Application No. 2009073719.
Response Dated Nov. 20, 2011 to European Search Report and the European Search Opinion of Apr. 8, 2011 From the European Patent Office Re. Application No. 10012376.9.
Response Dated Jul. 21, 2011 to Invitation Pursuant to Article 94(3) and Rule 71(1) EPC of Jun. 17, 2011 From the European Patent Office Re.: Application No. 04713966.2.
Response Dated Apr. 22, 2010 to Examination Report Dated Sep. 25, 2009 From the Instituto Mexicano de la Propriedad Industrial Re.: Application No. PA/a/2006/009612.
Response Dated Dec. 22, 2011 to Notice of the Reason for Rejection of Sep. 7, 2011 From the Korean Intellectual Property Office (KIPO) Re. Application No. 2011-7014421.
Response Dated Dec. 22, 2011 to Written Opinion of Jul. 26, 2011 From the Intellectual Property Office of Singapore, Issued by the Hungarian Patent Office on Apr. 6, 2011 Re. Application No. 2009073719.
Response Dated Mar. 22, 2010 to Examiner's Report of Jan. 5, 2010 From the Australian Patent Office Re.: Application No. 2004234635.

(56) References Cited

OTHER PUBLICATIONS

Response Dated Nov. 22, 2010 to Official Action of Jun. 21, 2010 From the US Patent and Trademark Office Re.: U.S. Appl. No. 12/385,894.
Response Dated Nov. 24, 2010 to Office Action of Jul. 25, 2010 From the Israeli Patent Office Re.: Application No. 171561.
Response Dated Nov. 24, 2011 to Notice of the Reason for Rejection of Aug. 24, 2011 From the Korean Intellectual Property Office (KIPO) Re. Application No. 2006-7019631.
Response Dated Apr. 25, 2010 to Office Action of Sep. 23, 2009 From the Israeli Patent Office Re.: Application No. 182888.
Response Dated Aug. 25, 2010 to Summons to Attend Oral Proceedings Pursuant to Rule 115(1) EPC of Jul. 23, 2010 From the European Patent Office Re.: Application No. 04713966.2.
Response Dated May 26, 2011 to Invitation Pursuant to Article 94(3) and Rule 71(1) EPC of Mar. 31, 2011 From the European Patent Office Re.: Application No. 04713966.2.
Response Dated Jul. 27, 2009 to Official Action of Apr. 8, 2009 From the US Patent and Trademark Office Re.: U.S. Appl. No. 10/554,387.
Response Dated Apr. 28, 2011 to Official Action of Oct. 29, 2010 From the US Patent and Trademark Office Re.: U.S. Appl. No. 10/554,387.
Response Dated Nov. 28, 2010 to Examination Report of Aug. 31, 2009 From the Australian Government, IP Australia Re.: Application No. 2005214181.
Response Dated Nov. 28, 2011 to Office Action of Jun. 9, 2011 From the US Patent and Trademark Office Re. U.S. Appl. No. 13/008,048.
Response Dated Nov. 28, 2011 to Office Action of Jun. 28, 2011 From the Israeli Patent Office Re.: Application No. 182888.
Response Dated Jun. 29, 2010 to Office Action of May 19, 2010 From the State Intellectual Property Office of the People's Republic of China Re.: Application No. 200480017916.2.
Response Dated Nov. 30, 2009 to Examiner's Report of Dec. 1, 2008 From the Australian Government, IP Australia Re.: Application No. 2004234635.
Response Dated Nov. 30, 2011 to Requisition by the Examiner of May 31, 2011 From the Canadian Intellectual Property Office Re. Application No. 2,557,525.
Response Dated Mar. 31, 2011 to Search Report and Written Opinion Dated Nov. 8, 2010 From the Intellectual Property Office of Singapore Issued by the Austrian Patent Office Re. Application No. 200717273-7.
Restriction Official Action Dated Jul. 11, 2012 From the US Patent and Trademark Office Re. U.S. Appl. No. 12/451,295.
Restriction Official Action Dated Mar. 12, 2012 From the US Patent and Trademark Office Re.: U.S. Appl. No. 12/451,188.
Restriction Official Action Dated Oct. 28, 2011 From the US Patent and Trademark Office Re. U.S. Appl. No. 13/080,692.
Restriction Official Action Dated Nov. 29, 2011 From the US Patent and Trademark Office Re. U.S. Appl. No. 13/080,694.
Search Report and Written Opinion Dated Nov. 8, 2010 From the Intellectual Property Office of Singapore Issued by the Austrian Patent Office Re. Application No. 200717273-7.
Search Report and Written Opinion Dated Jun. 14, 2010 From the Intellectual Property Office of Singapore, Issued by the Hungarian Patent Office on May 12, 2010 Re. Application No. 2009073719.
Search Report Dated Dec. 23, 2008 From the Intellectual Property Office of Singapore Issued by the Australian Patent Office Re.: Application No. SG 200800359-2.
Summary of Official Action Dated Mar. 29, 2010 From ROSPATENT, Federal Government Institution, Federal Institute of Industrial Property of the Federal Service for Intellectual Property, Patents and Trademarks of the Russian Federation Re. Application No. 2009140906.
Summons to Attend Oral Proceedings Pursuant to Rule 115(1) EPC Dated Jul. 23, 2010 From the European Patent Office Re.: Application No. 04713966.2.
Supplementary European Search Report and the European Search Opinion Dated Dec. 16, 2010 From the European Patent Office Re. Application No. 08738278.4.

Supplementary Partial European Search Report Dated Mar. 7, 2007 From the European Patent Office Re.: Application No. 04713966.2.
Translation of Notice of Reason for Rejection Dated Dec. 4, 2009 From the Japanese Patent Office Re.: Application No. 2006-507577.
Translation of Notice of Reason for Rejection Dated Jan. 4, 2011 From the Japanese Patent Office Re.: Application No. 2006-507577.
Translation of Notice of Reason for Rejection Dated May 8, 2012 From the Japanese Patent Office Re. Application No. 2010-507055.
Translation of Notice of Reason for Rejection Dated Sep. 16, 2011 From the Japanese Patent Office Re. Application No. 2007-500352.
Translation of Notice of Reason for Rejection Dated May 20, 2011 From the Japanese Patent Office Re. Application No. 2007-500352.
Translation of Notice of Reason for Rejection Dated Jun. 28, 2012 From the Korean Intellectual Property Office Re. Application No. 2011-7014421.
Translation of Notice of Reason for Rejection Dated Aug. 31, 2010 From the Japanese Patent Office Re. Application No. 2007-500352.
Translation of Notice of Reason for Rejection Dated Jan. 31, 2012 From the Japanese Patent Office Re.: Application No. 2006-507577.
Translation of Notice of the Reason for Rejection Dated Sep. 7, 2011 From the Korean Intellectual Property Office (KIPO) Re. Application No. 2011-7014421.
Translation of Notice of the Reason for Rejection Dated Mar. 12, 2011 From the Korean Intellectual Property Office Re. Application No. 2005-7020434.
Translation of Notice of the Reason for Rejection Dated Feb. 17, 2012 From the Korean Intellectual Property Office Re. Application No. 2005-7020434.
Translation of Notice of the Reason for Rejection Dated Jun. 20, 2012 From the Korean Intellectual Property Office Re. Application No. 10-2005-7020434.
Translation of Notice of the Reason for Rejection Dated Aug. 24, 2011 From the Korean Intellectual Property Office (KIPO) Re. Application No. 2006-7019631.
Translation of Notice of the Reason for Rejection Dated Apr. 26, 2012 From the Korean Intellectual Property Office (KIPO) Re. Application No. 2006-7019631.
Translation of Office Action Dated Nov. 6, 2009 From the State Intellectual Property Office of the People's Republic of China Re.: Application No. 200480017916.2.
Translation of Office Action Dated May 19, 2010 From the State Intellectual Property Office of the People's Republic of China Re.: Application No. 200480017916.2.
Translation of Request Dated Mar. 24, 2009 From the Patent Office of Ukraine Re. : Application No. 200511193.
Translation of the Office Action Dated Aug. 31, 2007 Form the Patent Office of the People's Republic of China Re.: Application No. 200480017916.2.
Translation of the Official Action Dated Jan. 16, 2007 From the Japanese Patent Office Re.: Application No. 515465/98.
Written Opinion and Search Report Dated Feb. 11, 2011 From the Intellectual Property Office of Singapore, Issued by the Hungarian Patent Office on Jan. 21, 2011 Re. Application No. 200907212-5.
Written Opinion and Search Report Dated Jun. 18, 2010 From the Intellectual Property Office of Singapore, Issued by the Hungarian Patent Office at May 13, 2010 Re. Application No. 200907212-5.
Written Opinion Dated Feb. 17, 2006 From the International Searching Authority Re.: Application No. PCT/IL04/00181.
Written Opinion Dated Dec. 23, 2008 From the Intellectual Property Office of Singapore Issued by the Australian Patent Office Re.: Application No. SG 200800359-2.
Written Opinion Dated Jul. 26, 2011 From the Intellectual Property Office of Singapore, Issued by the Hungarian Patent Office on Apr. 6, 2011 Re. Application No. 2009073719.
Written Opinion Dated May 27, 2009 From the International Searching Authority Re.: Application No. PCT/IL2008/000614.
Alfermann et al. "Natural Product Formation by Plant Cell Biotechnology. Results and Perspectives", Plant Cell, Tissue and Organ Culture, 43: 199-205, 1995.
Atkinson "Protein Trafficking in the Secretary and Endocytic Pathways", G817 Eukaryotic Cell Biology 2006, Internet Article, XP007917298, Retrieved From the Internet, p. 1-10, 2006.

(56) References Cited

OTHER PUBLICATIONS

Atkinson "RecName: Full—Polygalacturonase; Short=PG; EC=3.2.1.15; AltName: Full=Pectinase; Flags: Precursor", UniProtKB/Swiss-Prot., Medline=95062722, PGLR_MALDO, Accession No. P48978, Feb. 1, 1996.
Aviezer et al. "A Plant-Derived Recombinant Human Glucocerebrosidase Enzyme—A Preclinical and Phase I Investigation", PLoS One, 4(3): 1-6, Mar. 2009.
Barton et al. "Therapeutic Response to Intravenous Infusions of Glucocerebrosidase in a Patient With Gaucher Disease", Proc. Natl. Acad. Sci. USA 87: 1913-1916, Mar. 1990.
Berg-Fussman et al. "Human Acid Beta-Glucosidase. N-Glycosylation Site Occupancy and the Effect of Glycosylation on Enzymatic Activity", The Journal of Biological Chemistry, 268(20): 14861-14866, Jul. 15, 1993.
Boller et al. "DNA Sequence Encoding Vacuole Targetting Peptide—Esp. Signal Region of Tobacco Chitinase or Glucanase Gene, and Derived Recombinant DNA, Vectors, Etc. Functional in Plants", Database GenBank, US National Library of Medicine, No. AAR15823, 2003.
Boller et al. Alignment to Patent US 6,054,637, Apr. 25, 2000.
Borrell "Virus Hits Genzyme Plant, Halting Production of Orphan Drugs", SciAmericanblog 2009.
Branden et al. "Prediction, Engineering, and Design of Protein Structures", Introduction to Protein Structure, Garland Publishing, p. 247, 1991.
Chica et al. "Semi-Rational Approaches to Engineering Enzyme Activity: Combining the Benefits of Directed Evolution and Rational Design", Current Opinion in Biotechnology, 16(4): 378-384, Aug. 2005.
Chrispeels et al. "The Production of Recombinant Glycoproteins With Defined Non-Immunogenic Glycans", Transgenic Plant: A Production System for Industrial and Pharmaceutical Proteins, Chap.2: 99-102, 1996.
Cramer et al. "Bioproduction of Human Enzymes in Transgenic Tobacco", Annals of the New York Academy of Sciences, 792: 62-71, May 25, 1996.
Cramer et al. "Transgenic Plants for Therapeutic Proteins: Linking Upstream and Downstream Strategies", Current Topics in Microbiology and Immunology, XP009038354, 240: 95-108, 1992. p. 109-112, § 1.
Crooy et al. "Recombinant Glucocerebrosidase and Lyme Disease Vaccine Made by Genetic Engineering (No. 11 in a Series of Articles to Promote a Better Understanding of the Use of Genetic Engineering", Journal of Biotechnology, 76: 259-263, 2000.
Davis et al. "MemO: A Consensus Approach to the Annotation of a Protein's Membrane Organization", in Silico Biology, XP009141065, 6(5): 387-399, 2006. p. 391-392, 395, 397.
Dulk-Ra et al. "Electroporation of *Agrobacterium tumefaciens*", Methods in Molecular Biology, 55: 63-72, 1995. Abstract.
Erickson et al. "Biosynthesis of the Lysosomal Enzyme Glucocerebrosidase", The Journal of Biological Chemistry, 260(26): 14319-14324, 1985.
ExPASy "NiceZyme View of Enzyme: EC 3.2.1.45", UniProtKB/Swiss-Prot, ExPASy, 2008.
Fischer et al. "Molecular Farming of Pharmaceutical Proteins", Transgenic Research, 9: 279-299, 2000.
Fu et al. "Retention of Subunits of the Oligosaccharyltransferase Complex in the Endoplasmic Reticulum", The Journal of Biological Chemistry, XP002624334, 275(6): 3984-3990, Feb. 11, 2000. p. 3984, col. 2, § 2.
Gaucher "Cerezyme", Gaucher's Association UK Website, http://www.gaucher.org.uk/newsstory.php?action=show&id=73, Apr. 22, 2010.
Germain "Fabry Disease: Recent Advances in Enzyme Replacement Therapy", Expert Opinion on Investigational Drugs, 11(10): 1467-1476, Oct. 2002.
Giddings et al. "Transgenic Plants as Factories for Biopharmaceuticals", Nature Biotechnology, 18(11): 1151-1155, Nov. 2000.
Gomez et al. "Tonoplast and Soluble Vacuolar Proteins Are Targeted by Different Mechanisms", The Plant Cell, 5: 1113-1124, Sep. 1993.
Gomord et al. "Plant-Specific Glycosylation Patterns in the Context of Therapeutic Protein Production", Plant Biotechnology Journal, 8: 564-587, 2010.
Gomord et al. "Posttranslational Modification of Therapeutic Proteins in Plants", Current Opinion in Plant Biology, 7: 171-181, 2004.
Hardegger et al. "Transformation and Regeneration of Carrot (*Daucus carota* L.)", Molecular Breeding, 4: 119-127, 1998. Abstract.
Haseloff et al. "Removal of a Cryptic Intron and Subcellular Localization of Green Fluorescent Protein Are Required to Mark Transgenic *Arabidopsis* Plants Brightly", Proc. Natl. Acad. Sci. USA, 94: 2122-2127, Mar. 1997.
Hayes et al. "Remodelled, Recombinant Glucocerebrosidase (r-GCR)", Accession AAW07885, Jan. 28, 1997.
Hein et al. "Evaluation of Immunoglobulins From Plant Cells", Biotechnology Progress, XP001037084, 7(5): 455-461, 1991.
Hellens et al. "PGreen: A Versatile and Flexible Binary Ti Vector for Agrobacterium-Mediated Plant Transformation", Plant Molecular Biology, 42(6): 819-832, 2000. Abstract.
Holwerda et al. "In Vitro Processing of Aleurain, A Barley Vacuolar Thiol Protease", The Plant Cell, 2: 1091-1106, Nov. 1990.
Holwerda et al. "Proaleurain Vacuolar Targeting Is Mediated by Short Contiguous Peptide Interactions", The Plant Cell, 4: 307-318, Mar. 1992.
Hood et al. "Plant Binary Vector P1G121-Hm DNA, Complete Sequence", GenBank Nucleotide, Accession No. AB489142.1, 2009.
Horowitz "Human Glucocerebrosidase mRNA, Complete Cds", GenBank Nucleotide, Accession No. M19285.1, 1993.
James et al. "The Production of Foreign Proteins From Genetically Modified Plant Cells", Advances in Biochemical Engineering/Biotechnology, 72: 127-156, 2001.
Jefferson et al. "GUS Fusions: ?-Glucuronidase as a Sensitive and Versatile Gene Fusion Marker in Higher Plants", The EMBO Journal, 6(13): 3901-3907, 1987.
Karg et al. "The Production of Biopharmaceuticals in Plant Systems", Biotechnology Advances, XP002624335, 27(6): 879-894, Nov. 2009.
Ko et al. "Function and Glycosylation of Plant-Derived Antiviral Monoclonal Antibody", Proc. Natl. Acad. Sci. USA, 100(13): 8013-8018, 2003. p. 8013.
Laemmli "Relevant Page on Gel Electrophoresis", Nature, 227: 681, 1970.
Lee et al. "High-Density Algal Photobioreactors Using Light-Emitting Diodes", Biotechnology and Bioengineering, 44: 1161-1167, 1994.
Lerouge et al. "N-Glycoprotein Biosynthesis in Plants: Recent Developments and Future Trends", Plant Molecular Biology, XP002140796, 38: 31-48, Jan. 1, 1998. Figs.1, 2, 3, 5, 7.
Ma et al. "Genetic Modification: The Production of Recombinant Pharmaceutical Proteins in Plants", Nature Reviews Genetics 4: 794-805, 2003. Abstract.
Martin et al. "Glucosylceramidase Precursors (Beta-Glucocerebrosidase) (Acid Beta-Glucosidase) (D-Glucosyl-N-Acylsphingosine Glucohydrolase)", Fed. Proc., 43, 1984, GenBank NCBI Accession No. P04062, UniProtKB: Locus GLCM_HUMAN, GI: 121283, Apr. 1, 1993.
Martin et al. "Glycosylation and Processing of High Levels of Active Human Glucoceerebrosidase in Invertebrate Cells Using a Baculovirus Expression Vector", DNA, 7(2): 99-106, 1988.
Moran et al. "Fabry Kidney Disease", Saudi Journal of Kidney Diseases and Transplantation, 14(3): 367-377, 2003.
Neuhaus et al. "A Short C-Terminal Sequence Is Necessary and Sufficient for the Targeting of Chitinases to the Plant Vacuole (Cucumber / *Nicotiana silvestris* / *Nicotiana tabacum* / Plant Defense / Secretion)", Proc. Natl. Acad. Sci. USA, 88: 10362-10366, Nov. 1991. Abstract.
Neuhaus et al. "Mutation Analysis of the C-Terminal Vacuolar Targeting Peptide of Tobacco Chitinase: Low Specificity of the Sorting System, and Gradual Transition Between Intracellular Retention and Secretion Into the Extracellular Space", The Plant Journal, 5(1): 45-54, 1994.

(56) References Cited

OTHER PUBLICATIONS

Neuhaus et al. "Sorting of Proteins to Vacuoles in Plant Cells", Plant Molecular Biology, 38: 127-144, 1998.
Ozeki et al. "Effects of Inoculum Density, Zeatin and Sucrose on Anthocyanin Accumulation in a Carrot Suspension Culture", Plant Cell Tissue Organ Culture, 5: 45-53, 1985.
Podsakoff et al. "Human Glucocerebrosidase (GC) #2", WPI Score Search Results, Accession No. AAE02446, Aug. 10, 2001.
Press Release 2 "Protalix BioTherapeutics Announces Preliminary Top-Line Positive Data From Taliglucerase Alfa Switchover Trial", Protalix Biotherapeutics, Nov. 2, 2010.
Press Release 3 "Protalix RioTherapeutics Announces French ATU Granted for Taliglicerase Alfa for the Treatment of Gaucher Disease", Protalix Biotherapeutics, Jul. 13, 2010.
Ratner "Pfizer Stakes a Claim in Plant Cell-Made Biopharmaceuticals", Nature Biotechnology, 28(2): 107-108, Feb. 2010. Press Release 1.
Rayon et al. "The Protein N-Glycosylation in Plants", Journal of Experimental Botany, 49(326): 1463-1472, Sep. 1998.
Schähs et al. "Production of a Monoclonal Antibody in Plants With a Humanized N-Glycosylation Pattern", Plant Biotechnology Journal, 5(5): 657-663, Sep. 2007. Abstract.
Seffernick et al. "Melamine Deaminase and Atrazine Chlorohydrolase: 98 Percent Identical But Functionally Different", Journal of Bacteriology, 183(8): 2405-2410, Apr. 2001.
Sen et al. "Developments in Directed Evolution for Improving Enzyme Functions", Applied Biochemistry and Biotechnology, 143(3): 212-223, Dec. 2007.
Shaaltiel et al. "Production of Glucocerebrosidase With Terminal Mannose Glycans for Enzyme Replacement Therapy of Gaucher's Disease Using a Plant Cell System", Plant Biotechnology Journal, XP002609251, 5(5): 579-590, Sep. 2007.
Sharp et al. "Characterization of Monoclonal Antibody Fragments Produced by Plant Cells", Biotechnology and Bioengineering, XP002432979, 73(5): 338-346, 2001. p. 345, col. 2, § 2.
Sorge et al. "Glucocerebrosidase Precursor (5' End Put.); Putative [*Homo sapiens*]", Database NCBI, GenBank Accession No. AAA35873, Apr. 27, 1993.
Sorge et al. "Molecular Cloning and Nucleotide Sequence of Human Glucocerebrosidase cDNA", Proc. Natl. Acad. Sci. USA, 82: 7289-7293, Nov. 1985.
Sorge et al. Alignments, Sequence List, 10/554387 SEQ ID No. 8.
Strous et al. "Differential Effects of Brefeldin A on Transport of Secretory and Lysomal Proteins", The Journal of Biological Chemistry, XP009141068, 268(4): 2341-2347, Feb. 5, 1993. Abstract.
Syrkin Wurtele et al. "A Simple, Efficient Method for the Agrobacterium-Mediated Transformation of Carrot Callus Cells", Plant Science, 61(2): 253-262, 1989.
Tsuji et al. "Alpha-Galactosidase [*Homo sapiens*]", GenBank EMBL, Version CAA29232.1, GI:757912, Accession No. CAA29232.
Tsuji et al. "Nucleotide Sequence of cDNA Containing the Complete Cosing Sequence for Human Lysosomal Glucocerebrosidase", The Journal of Biological Chemistry, 261(1): 50-53, Jan. 5, 1986.
Tsuji et al. "RecName: Full=Alpha-Galactosidase A; EC=3. 2.1.22; AltName: Full=Alpha-D-Galactosidase A; AltName: Full=Alpha-D-Galactoside Galactohydrolase; AltName: Full=Melibiase; AltName: INN=Agalsidase; Flags: Precursor", UniProtKB/Swiss-Prot., Medline=87246603, AGAL_HUMAN, Accession No. P06280, Jan. 1, 1988.
Van Patten et al. "Effect of Mannose Chain length on Targeting of Glucocerebrosidase for Enzyme Replacement Therapy of Gaucher Disease", Glycobiology, 17(5): 467-478, 2007.
Van Weely et al. "Function of Oligosaccharide Modifications in Glucocerebrebrosidase, A Membrane-Associated Lysosomal Hydrolase", European Journal of Biochemistry, 191(3): 669-677, 1990.
Vitale et al. "The Endoplasmic Reticulum—Gateway of the Secretory Pathway", The Plant Cell, 11: 615-628, Apr. 1999.
Wandelt et al. "Vicilin With Carboxy-Terminal KDEL Is Retained in the Endoplasmic Reticulum and Accumulates to High Levels in the Leaves of Transgenic Plants", Plant Journal, 2(2): 181-192, Mar. 1992. Abstract. Witkowski et al. "Conversion of A ?-Ketoacyl Synthase to a Malonyl Decarboxylase by Replacement of the Active-Site Cysteine With Glutamine", Biochemistry, 38(36): 11643-11650, 1999.
Zhu et al. "Novel Polynucleic Acid Segment Useful for Modulating Gene Expression Within a Cell by Posttranscriptional Gene Silencing, and for Augmenting a Plant Cell Genome", Database GenBank, US National Library of Medicine, No. ABP81239, 2003.
Communication Pursuant to Article 94(3) EPC Dated Sep. 12, 2012 From the European Patent Office Re. Application No. 10012373.6.
Communication Pursuant to Article 94(3) EPC Dated Aug. 14, 2012 From the European Patent Office Re. Application No. 10012375.1.
Communication Pursuant to Article 94(3) EPC Dated Aug. 28, 2012 From the European Patent Office Re. Application No. 10012372.8.
Office Action Dated Aug. 28, 2012 From the US Patent and Trademark Office Re. U.S. Appl. No. 13/008,048.
Notice of Allowance Dated Nov. 13, 2012 From the US Patent and Trademark Office Re. U.S. Appl. No. 13/080,694.
Requisition by the Examiner Dated Oct. 11, 2012 From the Canadian Intellectual Property Office Re. Application No. 2,557,525.
Translation of Notice of Reason for Rejection Dated Nov. 13, 2012 From the Japanese Patent Office Re. Application No. 2011-99013.
Translation of Office Action Dated Sep. 29, 2012 From the State Intellectual Property Office of the People's Republic of China Re. Application No. 200880023217.7.
Written Opinion Dated Oct. 23, 2012 From the Intellectual Property Office of Singapore Issued by the Austrian Patent Office Re. Application No. 200717273-7.
Braun et al. "Metabolic Correction and Cross-Correction of Mucopolysaccharidosis Type II (Hunter Syndrome) by Retroviral-Mediated Gene Transfer and Expression of Human Iduronate-2-Sultatase", Proc. Natl. Acad. Sci. USA, 90: 11830-11834, Dec. 1993.

* cited by examiner

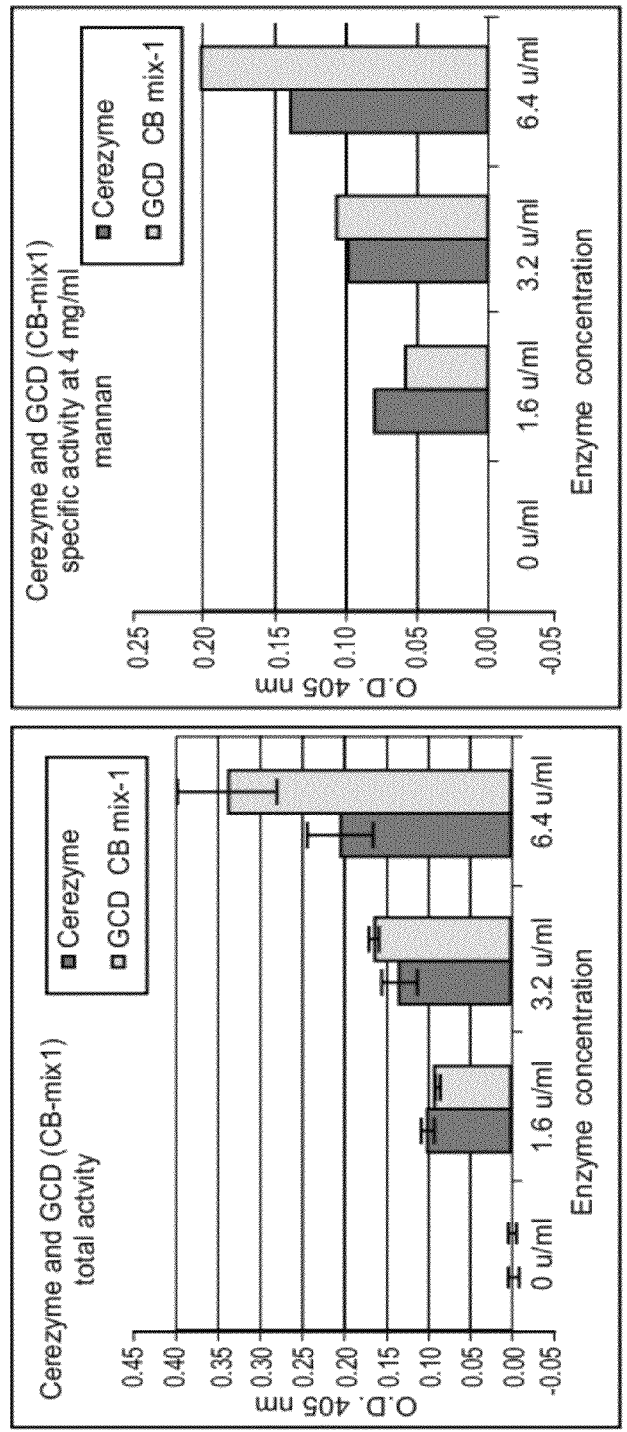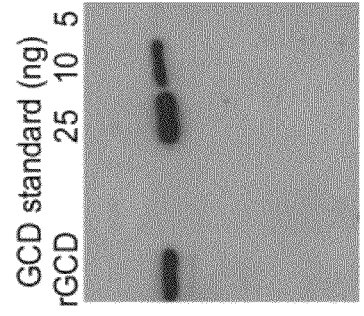
Fig. 5c
Fig. 5d

Theoretical monoisotopic mass for [M+Na]$^+$ molecular ion = 1171.5

Theoretical monoisotopic mass for [M+Na]$^+$ molecular ion = 1331.6

Theoretical monoisotopic mass for [M+Na]$^+$ molecular ion = 1345.6

Theoretical monoisotopic mass for [M+Na]$^+$ molecular ion = 1505.7

Theoretical monoisotopic mass for [M+Na]$^+$ molecular ion = 1579.8

Theoretical monoisotopic mass for [M+Na]$^+$ molecular ion = 1709.7

Theoretical monoisotopic mass for [M+Na]$^+$ molecular ion = 1750.9

Theoretical monoisotopic mass for [M+Na]$^+$ molecular ion = 1783.9

Theoretical monoisotopic mass for [M+Na]⁺ molecular ion = 1989.0

Theoretical monoisotopic mass for [M+Na]⁺ molecular ion = 1997.0

Theoretical monoisotopic mass for [M+Na]⁺ molecular ion = 2130.0

Theoretical monoisotopic mass for [M+Na]⁺ molecular ion = 2193.1

Theoretical monoisotopic mass for [M+Na]$^+$ molecular ion = 2375.2

Theoretical monoisotopic mass for [M+Na]$^+$ molecular ion = 2375.2

Key: ▼ Fucose
● Galactose
□ N-Acetylglucosamine
○ Mannose
⬠ Xylose

SEQUENCE LISTING

<160> NUMBER OF SEQ ID NOS: 15

<210> SEQ ID NO 1
<211> LENGTH: 22
<212> TYPE: PRT
<213> ORGANISM: Artificial sequence
<220> FEATURE:
<223> OTHER INFORMATION: ER signal peptide

<400> SEQUENCE: 1

Met Lys Thr Asn Leu Phe Leu Phe Leu Ile Phe Ser Leu Leu Leu Ser
1               5                   10                  15

Leu Ser Ser Ala Glu Phe
            20

<210> SEQ ID NO 2
<211> LENGTH: 7
<212> TYPE: PRT
<213> ORGANISM: Artificial sequence
<220> FEATURE:
<223> OTHER INFORMATION: Vacuolar targeting signal from Tobacco
      chitinase A

<400> SEQUENCE: 2

Asp Leu Leu Val Asp Thr Met
1               5

<210> SEQ ID NO 3
<211> LENGTH: 21
<212> TYPE: DNA
<213> ORGANISM: Artificial sequence
<220> FEATURE:
<223> OTHER INFORMATION: Single strand DNA oligonucleotide

<400> SEQUENCE: 3
cagaattcgc ccgcccctgc a                                        21

<210> SEQ ID NO 4
<211> LENGTH: 22
<212> TYPE: DNA
<213> ORGANISM: Artificial sequence
<220> FEATURE:
<223> OTHER INFORMATION: Single strand DNA oligonucleotide

<400> SEQUENCE: 4
ctcagatctt ggcgatgcca ca                                       22

<210> SEQ ID NO 5
<211> LENGTH: 19
<212> TYPE: DNA
<213> ORGANISM: Artificial sequence
<220> FEATURE:
<223> OTHER INFORMATION: Single strand DNA oligonucleotide

<400> SEQUENCE: 5
ctcagaagac cagagggct                                           19

<210> SEQ ID NO 6
<211> LENGTH: 17
<212> TYPE: DNA
<213> ORGANISM: Artificial sequence
<220> FEATURE:
<223> OTHER INFORMATION: Single strand DNA oligonucleotide

<400> SEQUENCE: 6
caaagcggcc atcgtgc                                             17

<210> SEQ ID NO 7
<211> LENGTH: 1491
<212> TYPE: DNA
<213> ORGANISM: Homo sapiens

<400> SEQUENCE: 7
gcccgcccct gcatccctaa aagcttcggc tacagctcgg tggtgtgtgt ctgcaatgcc    60

```
acatactgtg actcctttga ccccccgacc tttcctgccc ttggtacctt cagccgctat    120
gagagtacac gcagtgggcg acggatggag ctgagtatgg ggcccatcca ggctaatcac    180
acgggcacag gcctgctact gaccctgcag ccagaacaga agttccagaa agtgaaggga    240
tttggagggg ccatgacaga tgctgctgct ctcaacatcc ttgccctgtc acccctgcc     300 caaaatttgc tacttaaatc gtacttctct gaagaaggaa tcggatataa catcatccgg    360
gtacccatgg ccagctgtga cttctccatc cgcacctaca cctatgcaga cacccctgat    420
gatttccagt tgcacaactt cagcctccca gaggaagata ccaagctcaa gatacccctg    480
attcaccgag ccctgcagtt ggcccagcgt cccgtttcac tccttgccag cccctggaca    540
tcacccactt ggctcaagac caatggagcg gtgaatggga aggggtcact caagggacag    600
cccggagaca tctaccacca gacctgggcc agatactttg tgaagttcct ggatgcctat    660
gctgagcaca agttacagtt ctgggcagtg acagctgaaa atgagccttc tgctgggctg    720
ttgagtggat accccttcca gtgcctgggc ttcacccctg aacatcagcg agacttcatt    780
gcccgtgacc taggtcctac cctcgccaac agtactcacc acaatgtccg cctactcatg    840
ctggatgacc aacgcttgct gctgccccac tgggcaaagg tggtactgac agacccagaa    900
gcagctaaat atgttcatgg cattgctgta cattggtacc tggactttct ggctccagcc    960
aaagccaccc taggggagac acaccgcctg ttccccaaca ccatgctctt tgcctcagag   1020
gcctgtgtgg gctccaagtt ctgggagcag agtgtgcggc taggctcctg ggatcgaggg   1080
atgcagtaca gccacagcat catcacgaac ctcctgtacc atgtggtcgg ctggaccgac   1140
tggaaccttg ccctgaaccc cgaaggagga cccaattggg tgcgtaactt tgtcgacagt   1200
cccatcattg tagacatcac caaggacacg ttttacaaac agcccatgtt ctaccacctt   1260
ggccacttca gcaagttcat tcctgagggc tcccagagag tggggctggt tgccagtcag   1320
aagaacgacc tggacgcagt ggcactgatg catcccgatg ctctgctgt tgtggtcgtg   1380 ctaaaccgct cctctaagga tgtgcctctt accatcaagg atcctgctgt gggcttcctg   1440
gagacaatct cacctggcta ctccattcac acctacctgt ggcatcgcca g            1491
```

<210> SEQ ID NO 8
<211> LENGTH: 497
<212> TYPE: PRT
<213> ORGANISM: Homo sapiens

<400> SEQUENCE: 8

```
Ala Arg Pro Cys Ile Pro Lys Ser Phe Gly Tyr Ser Ser Val Val Cys
1               5                   10                  15

Val Cys Asn Ala Thr Tyr Cys Asp Ser Phe Asp Pro Thr Phe Pro
            20                  25                  30

Ala Leu Gly Thr Phe Ser Arg Tyr Glu Ser Thr Arg Ser Gly Arg Arg
        35                  40                  45

Met Glu Leu Ser Met Gly Pro Ile Gln Ala Asn His Thr Gly Thr Gly
    50                  55                  60

Leu Leu Leu Thr Leu Gln Pro Glu Gln Lys Phe Gln Lys Val Lys Gly
65                  70                  75                  80

Phe Gly Gly Ala Met Thr Asp Ala Ala Ala Leu Asn Ile Leu Ala Leu
                85                  90                  95

Ser Pro Pro Ala Gln Asn Leu Leu Leu Lys Ser Tyr Phe Ser Glu Glu
            100                 105                 110

Gly Ile Gly Tyr Asn Ile Ile Arg Val Pro Met Ala Ser Cys Asp Phe
        115                 120                 125
```

Ser Ile Arg Thr Tyr Thr Tyr Ala Asp Thr Pro Asp Asp Phe Gln Leu
130                 135                 140

His Asn Phe Ser Leu Pro Glu Glu Asp Thr Lys Leu Lys Ile Pro Leu
145                 150                 155                 160

Ile His Arg Ala Leu Gln Leu Ala Gln Arg Pro Val Ser Leu Leu Ala
                165                 170                 175

Ser Pro Trp Thr Ser Pro Thr Trp Leu Lys Thr Asn Gly Ala Val Asn
            180                 185                 190

Gly Lys Gly Ser Leu Lys Gly Gln Pro Gly Asp Ile Tyr His Gln Thr
        195                 200                 205

Trp Ala Arg Tyr Phe Val Lys Phe Leu Asp Ala Tyr Ala Glu His Lys
210                 215                 220

Leu Gln Phe Trp Ala Val Thr Ala Glu Asn Glu Pro Ser Ala Gly Leu
225                 230                 235                 240

Leu Ser Gly Tyr Pro Phe Gln Cys Leu Gly Phe Thr Pro Glu His Gln
                245                 250                 255

Arg Asp Phe Ile Ala Arg Asp Leu Gly Pro Thr Leu Ala Asn Ser Thr
            260                 265                 270

His His Asn Val Arg Leu Leu Met Leu Asp Asp Gln Arg Leu Leu Leu
        275                 280                 285

Pro His Trp Ala Lys Val Val Leu Thr Asp Pro Glu Ala Ala Lys Tyr
290                 295                 300

Val His Gly Ile Ala Val His Trp Tyr Leu Asp Phe Leu Ala Pro Ala
305                 310                 315                 320

Lys Ala Thr Leu Gly Glu Thr His Arg Leu Phe Pro Asn Thr Met Leu
                325                 330                 335

Phe Ala Ser Glu Ala Cys Val Gly Ser Lys Phe Trp Glu Gln Ser Val
            340                 345                 350

Arg Leu Gly Ser Trp Asp Arg Gly Met Gln Tyr Ser His Ser Ile Ile
        355                 360                 365

Thr Asn Leu Leu Tyr His Val Val Gly Trp Thr Asp Trp Asn Leu Ala
370                 375                 380

Leu Asn Pro Glu Gly Gly Pro Asn Trp Val Arg Asn Phe Val Asp Ser
385                 390                 395                 400

Pro Ile Ile Val Asp Ile Thr Lys Asp Thr Phe Tyr Lys Gln Pro Met
                405                 410                 415

Phe Tyr His Leu Gly His Phe Ser Lys Phe Ile Pro Glu Gly Ser Gln
            420                 425                 430

Arg Val Gly Leu Val Ala Ser Gln Lys Asn Asp Leu Asp Ala Val Ala
        435                 440                 445

Leu Met His Pro Asp Gly Ser Ala Val Val Val Leu Asn Arg Ser
450                 455                 460

Ser Lys Asp Val Pro Leu Thr Ile Lys Asp Pro Ala Val Gly Phe Leu
465                 470                 475                 480

Glu Thr Ile Ser Pro Gly Tyr Ser Ile His Thr Tyr Leu Trp His Arg
                485                 490                 495

Gln

<210> SEQ ID NO 9
<211> LENGTH: 338
<212> TYPE: DNA
<213> ORGANISM: Cauliflower mosaic virus

<400> SEQUENCE: 9
ttttcacaaa gggtaatatc gggaaacctc ctcggattcc attgcccagc tatctgtcac      60

-continued

```
ttcatcgaaa ggacagtaga aaaggaaggt ggctcctaca aatgccatca ttgcgataaa    120
ggaaaggcta tcgttcaaga tgcctctacc gacagtggtc ccaaagatgg accccaccc     180 acgaggaaca tcgtggaaaa agaagacgtt ccaaccacgt cttcaaagca agtggattga    240
tgtgatatct ccactgacgt aagggatgac gcacaatccc actatccttc gcaagaccct    300
tcctctatat aaggaagttc atttcatttg gagaggac                            338
```

<210> SEQ ID NO 10
<211> LENGTH: 66
<212> TYPE: DNA
<213> ORGANISM: Artificial sequence
<220> FEATURE:
<223> OTHER INFORMATION: Nucleic acid sequence encoding the ER signal
      peptide

<400> SEQUENCE: 10

```
atgaagacta atcttttct ctttctcatc ttttcacttc tcctatcatt atcctcggcc    60
gaattc                                                              66
```

<210> SEQ ID NO 11
<211> LENGTH: 21
<212> TYPE: DNA
<213> ORGANISM: Artificial sequence
<220> FEATURE:
<223> OTHER INFORMATION: Nucleic acid sequence encoding the vacuolar
      targeting sequence

<400> SEQUENCE: 11

```
gatcttttag tcgatactat g                                             21
```

<210> SEQ ID NO 12
<211> LENGTH: 167
<212> TYPE: DNA
<213> ORGANISM: Artificial sequence
<220> FEATURE:
<223> OTHER INFORMATION: Nucleic acid sequence of the Agrobacterium
      tumefaciens terminator
<220> FEATURE:
<221> NAME/KEY: misc_feature
<222> LOCATION: (162)..(162)
<223> OTHER INFORMATION: n is a, c, g, or t

<400> SEQUENCE: 12

```
taatttcatg atctgttttg ttgtattccc ttgcaatgca gggcctaggg ctatgaataa    60
agttaatgtg tgaatgtgtg aatgtgtgat tgtgacctga agggatcacg actataatcg    120
tttataataa acaaagactt tgtcccaaaa accccccccc cngcaga                 167
```

<210> SEQ ID NO 13
<211> LENGTH: 2186
<212> TYPE: DNA
<213> ORGANISM: Artificial sequence
<220> FEATURE:
<223> OTHER INFORMATION: nucleic acid sequence encoding high mannose
      human glucocerebrosidase (GCD)
<220> FEATURE:
<221> NAME/KEY: misc_feature
<222> LOCATION: (2181)..(2181)
<223> OTHER INFORMATION: n is a, c, g, or t

<400> SEQUENCE: 13

```
ttttcacaaa gggtaatatc gggaaacctc ctcggattcc attgcccagc tatctgtcac    60
ttcatcgaaa ggacagtaga aaaggaaggt ggctcctaca aatgccatca ttgcgataaa    120
ggaaaggcta tcgttcaaga tgcctctacc gacagtggtc ccaaagatgg accccaccc     180
```

```
acgaggaaca tcgtggaaaa agaagacgtt ccaaccacgt cttcaaagca agtggattga    240
tgtgatatct ccactgacgt aagggatgac gcacaatccc actatccttc gcaagaccct    300
tcctctatat aaggaagttc atttcatttg gagaggacag gcttcttgag atccttcaac    360
aattaccaac aacaacaaac aacaaacaac attacaatta ctatttacaa ttacagtcga    420
gggatccaag gagatataac aatgaagact aatcttttc tctttctcat cttttcactt    480
ctcctatcat tatcctcggc cgaattcgcc cgcccctgca tccctaaaag cttcggctac    540
agctcggtgg tgtgtgtctg caatgccaca tactgtgact cctttgaccc ccgacctt    600 cctgcccttg gtaccttcag ccgctatgag agtacacgca gtgggcgacg gatggagctg    660 agtatgggc ccatccaggc taatcacacg ggcacaggcc tgctactgac cctgcagcca    720
gaacagaagt tccagaaagt gaagggattt ggaggggcca tgacagatgc tgctgctctc    780
aacatccttg ccctgtcacc ccctgcccaa aatttgctac ttaaatcgta cttctctgaa    840
gaaggaatcg gatataacat catccgggta cccatggcca gctgtgactt ctccatccgc    900
acctacacct atgcagacac ccctgatgat ttccagttgc acaacttcag cctcccagag    960
gaagatacca agctcaagat accctgatt caccgagcc tgcagttggc ccagcgtccc    1020
gtttcactcc ttgccagccc ctggacatca cccacttggc tcaagaccaa tggagcggtg    1080
aatgggaagg ggtcactcaa gggacagccc ggagacatct accaccagac tgggccaga    1140 tactttgtga agttcctgga tgcctatgct gagcacaagt tacagttctg gcagtgaca    1200 gctgaaaatg agccttctgc tgggctgttg agtggatacc ccttccagtg cctgggcttc    1260 accctgaac atcagcgaga cttcattgcc cgtgacctag gtcctaccct cgccaacagt    1320
actcaccaca atgtccgcct actcatgctg gatgaccaac gcttgctgct gccccactgg    1380
gcaaaggtgg tactgacaga cccagaagca gctaaatatg ttcatggcat tgctgtacat    1440
tggtacctgg acttctggc tccagccaaa gccaccctag gggagacaca ccgcctgttc    1500
cccaacacca tgctctttgc ctcagaggcc tgtgtgggct ccaagttctg ggagcagagt    1560
gtgcggctag gctcctggga tcagggatg cagtacagcc acagcatcat cacgaacctc    1620
ctgtaccatg tggtcggctg gaccgactgg aaccttgccc tgaaccccga aggaggaccc    1680
aattgggtgc gtaactttgt cgacagtccc atcattgtag acatcaccaa ggacacgttt    1740
tacaaacagc ccatgttcta ccaccttggc cacttcagca agttcattcc tgagggctcc    1800
cagagagtgg ggctggttgc cagtcagaag aacgacctgg acgcagtggc actgatgcat    1860
cccgatggct ctgctgttgt ggtcgtgcta aaccgctcct ctaaggatgt gcctcttacc    1920
atcaaggatc ctgctgtggg cttcctggag acaatctcac ctggctactc cattcacacc    1980
tacctgtggc atcgccaaga tcttttagtc gatactatgt aatttcatga tctgttttgt    2040
tgtattccct tgcaatgcag ggcctagggc tatgaataaa gttaatgtgt gaatgtgtga    2100
atgtgtgatt gtgacctgaa gggatcacga ctataatcgt ttataataaa caaagacttt    2160
gtcccaaaaa cccccccccc ngcaga                                         2186
```

<210> SEQ ID NO 14
<211> LENGTH: 526
<212> TYPE: PRT
<213> ORGANISM: Artificial sequence
<220> FEATURE:
<223> OTHER INFORMATION: High mannose human glucocerebrosidase (GCD)

<400> SEQUENCE: 14

Met Lys Thr Asn Leu Phe Leu Phe Leu Ile Phe Ser Leu Leu Leu Ser

-continued

```
1               5               10              15
Leu Ser Ser Ala Glu Phe Ala Arg Pro Cys Ile Pro Lys Ser Phe Gly
                20              25              30

Tyr Ser Ser Val Val Cys Val Cys Asn Ala Thr Tyr Cys Asp Ser Phe
        35              40              45

Asp Pro Pro Thr Phe Pro Ala Leu Gly Thr Phe Ser Arg Tyr Glu Ser
    50              55              60

Thr Arg Ser Gly Arg Arg Met Glu Leu Ser Met Gly Pro Ile Gln Ala
65              70              75              80

Asn His Thr Gly Thr Gly Leu Leu Leu Thr Leu Gln Pro Glu Gln Lys
                85              90              95

Phe Gln Lys Val Lys Gly Phe Gly Gly Ala Met Thr Asp Ala Ala Ala
                100             105             110

Leu Asn Ile Leu Ala Leu Ser Pro Pro Ala Gln Asn Leu Leu Leu Lys
            115             120             125

Ser Tyr Phe Ser Glu Glu Gly Ile Gly Tyr Asn Ile Ile Arg Val Pro
            130             135             140

Met Ala Ser Cys Asp Phe Ser Ile Arg Thr Tyr Thr Tyr Ala Asp Thr
145             150             155             160

Pro Asp Asp Phe Gln Leu His Asn Phe Ser Leu Pro Glu Glu Asp Thr
                165             170             175

Lys Leu Lys Ile Pro Leu Ile His Arg Ala Leu Gln Leu Ala Gln Arg
                180             185             190

Pro Val Ser Leu Leu Ala Ser Pro Trp Thr Ser Pro Thr Trp Leu Lys
                195             200             205

Thr Asn Gly Ala Val Asn Gly Lys Gly Ser Leu Lys Gly Gln Pro Gly
            210             215             220

Asp Ile Tyr His Gln Thr Trp Ala Arg Tyr Phe Val Lys Phe Leu Asp
225             230             235             240

Ala Tyr Ala Glu His Lys Leu Gln Phe Trp Ala Val Thr Ala Glu Asn
                245             250             255

Glu Pro Ser Ala Gly Leu Leu Ser Gly Tyr Pro Phe Gln Cys Leu Gly
            260             265             270

Phe Thr Pro Glu His Gln Arg Asp Phe Ile Ala Arg Asp Leu Gly Pro
        275             280             285

Thr Leu Ala Asn Ser Thr His His Asn Val Arg Leu Leu Met Leu Asp
        290             295             300

Asp Gln Arg Leu Leu Leu Pro His Trp Ala Lys Val Val Leu Thr Asp
305             310             315             320

Pro Glu Ala Ala Lys Tyr Val His Gly Ile Ala Val His Trp Tyr Leu
                325             330             335

Asp Phe Leu Ala Pro Ala Lys Ala Thr Leu Gly Glu Thr His Arg Leu
            340             345             350

Phe Pro Asn Thr Met Leu Phe Ala Ser Glu Ala Cys Val Gly Ser Lys
            355             360             365

Phe Trp Glu Gln Ser Val Arg Leu Gly Ser Trp Asp Arg Gly Met Gln
    370             375             380

Tyr Ser His Ser Ile Ile Thr Asn Leu Leu Tyr His Val Val Gly Trp
385             390             395             400

Thr Asp Trp Asn Leu Ala Leu Asn Pro Glu Gly Gly Pro Asn Trp Val
                405             410             415

Arg Asn Phe Val Asp Ser Pro Ile Ile Val Asp Ile Thr Lys Asp Thr
                420             425             430
```

```
Phe Tyr Lys Gln Pro Met Phe Tyr His Leu Gly His Phe Ser Lys Phe
        435                 440                 445

Ile Pro Glu Gly Ser Gln Arg Val Gly Leu Val Ala Ser Gln Lys Asn
    450                 455                 460

Asp Leu Asp Ala Val Ala Leu Met His Pro Asp Gly Ser Ala Val Val
465                 470                 475                 480

Val Val Leu Asn Arg Ser Ser Lys Asp Val Pro Leu Thr Ile Lys Asp
                485                 490                 495

Pro Ala Val Gly Phe Leu Glu Thr Ile Ser Pro Gly Tyr Ser Ile His
                500                 505                 510

Thr Tyr Leu Trp His Arg Gln Asp Leu Leu Val Asp Thr Met
            515                 520                 525

<210> SEQ ID NO 15
<211> LENGTH: 506
<212> TYPE: PRT
<213> ORGANISM: Artificial sequence
<220> FEATURE:
<223> OTHER INFORMATION: Processed plant produced human recombinant GCD
      protein

<400> SEQUENCE: 15

Glu Phe Ala Arg Pro Cys Ile Pro Lys Ser Phe Gly Tyr Ser Ser Val
1               5                   10                  15

Val Cys Val Cys Asn Ala Thr Tyr Cys Asp Ser Phe Asp Pro Pro Thr
                20                  25                  30

Phe Pro Ala Leu Gly Thr Phe Ser Arg Tyr Glu Ser Thr Arg Ser Gly
            35                  40                  45

Arg Arg Met Glu Leu Ser Met Gly Pro Ile Gln Ala Asn His Thr Gly
    50                  55                  60

Thr Gly Leu Leu Leu Thr Leu Gln Pro Glu Gln Lys Phe Gln Lys Val
65                  70                  75                  80

Lys Gly Phe Gly Gly Ala Met Thr Asp Ala Ala Ala Leu Asn Ile Leu
                85                  90                  95

Ala Leu Ser Pro Pro Ala Gln Asn Leu Leu Leu Lys Ser Tyr Phe Ser
                100                 105                 110

Glu Glu Gly Ile Gly Tyr Asn Ile Ile Arg Val Pro Met Ala Ser Cys
            115                 120                 125

Asp Phe Ser Ile Arg Thr Tyr Thr Tyr Ala Asp Thr Pro Asp Asp Phe
    130                 135                 140

Gln Leu His Asn Phe Ser Leu Pro Glu Glu Asp Thr Lys Leu Lys Ile
145                 150                 155                 160

Pro Leu Ile His Arg Ala Leu Gln Leu Ala Gln Arg Pro Val Ser Leu
                165                 170                 175

Leu Ala Ser Pro Trp Thr Ser Pro Thr Trp Leu Lys Thr Asn Gly Ala
                180                 185                 190

Val Asn Gly Lys Gly Ser Leu Lys Gly Gln Pro Gly Asp Ile Tyr His
            195                 200                 205

Gln Thr Trp Ala Arg Tyr Phe Val Lys Phe Leu Asp Ala Tyr Ala Glu
    210                 215                 220

His Lys Leu Gln Phe Trp Ala Val Thr Ala Glu Asn Glu Pro Ser Ala
225                 230                 235                 240

Gly Leu Leu Ser Gly Tyr Pro Phe Gln Cys Leu Gly Phe Thr Pro Glu
                245                 250                 255

His Gln Arg Asp Phe Ile Ala Arg Asp Leu Gly Pro Thr Leu Ala Asn
                260                 265                 270
```

```
Ser Thr His His Asn Val Arg Leu Leu Met Leu Asp Asp Gln Arg Leu
        275             280             285
Leu Leu Pro His Trp Ala Lys Val Val Leu Thr Asp Pro Glu Ala Ala
        290             295             300
Lys Tyr Val His Gly Ile Ala Val His Trp Tyr Leu Asp Phe Leu Ala
305             310             315             320
Pro Ala Lys Ala Thr Leu Gly Glu Thr His Arg Leu Phe Pro Asn Thr
                325             330             335
Met Leu Phe Ala Ser Glu Ala Cys Val Gly Ser Lys Phe Trp Glu Gln
            340             345             350
Ser Val Arg Leu Gly Ser Trp Asp Arg Gly Met Gln Tyr Ser His Ser
        355             360             365
Ile Ile Thr Asn Leu Leu Tyr His Val Val Gly Trp Thr Asp Trp Asn
        370             375             380
Leu Ala Leu Asn Pro Glu Gly Gly Pro Asn Trp Val Arg Asn Phe Val
385             390             395             400
Asp Ser Pro Ile Ile Val Asp Ile Thr Lys Asp Thr Phe Tyr Lys Gln
            405             410             415
Pro Met Phe Tyr His Leu Gly His Phe Ser Lys Phe Ile Pro Glu Gly
            420             425             430
Ser Gln Arg Val Gly Leu Val Ala Ser Gln Lys Asn Asp Leu Asp Ala
        435             440             445
Val Ala Leu Met His Pro Asp Gly Ser Ala Val Val Val Val Leu Asn
        450             455             460
Arg Ser Ser Lys Asp Val Pro Leu Thr Ile Lys Asp Pro Ala Val Gly
465             470             475             480
Phe Leu Glu Thr Ile Ser Pro Gly Tyr Ser Ile His Thr Tyr Leu Trp
            485             490             495
His Arg Gln Asp Leu Leu Val Asp Thr Met
            500             505
```

HUMAN LYSOSOMAL PROTEINS FROM PLANT CELL CULTURE

RELATED APPLICATIONS

This application is a divisional of U.S. patent application Ser. No. 13/080,692 filed on Apr. 6, 2011, which is a divisional of U.S. patent application Ser. No. 11/790,991 filed on Apr. 30, 2007, now U.S. Pat. No. 7,951,557, which is a continuation-in-part of pending U.S. patent application Ser. No. 10/554,387 filed on Oct. 25, 2005, which is a National Phase of PCT Patent Application No. PCT/IL2004/000181 having International Filing Date of Feb. 24, 2004, which claims the benefit of priority of Israel Patent Application No. 155588 filed on Apr. 27, 2003, now abandoned. The contents of the above applications are all incorporated herein by reference.

FIELD OF THE INVENTION

The present invention relates to transformed host cells for the production of high mannose proteins and a method and system for producing these proteins, particularly in plant culture.

BACKGROUND OF THE INVENTION

Gaucher's disease is the most prevalent lysosomal storage disorder. It is caused by a recessive genetic disorder (chromosome 1 q21-q31) resulting in deficiency of glucocerebrosidase, also known as glucosylceramidase, which is a membrane-bound lysosomal enzyme that catalyzes the hydrolysis of the glycosphingolipid glucocerebroside (glucosylceramide, GlcCer) to glucose and ceramide. Gaucher disease is caused by point mutations in the hGCD (human glucocerebrosidase) gene (GBA), which result in accumulation of GlcCer in the lysosomes of macrophages. The characteristic storage cells, called Gaucher cells, are found in liver, spleen and bone marrow. The associated clinical symptoms include severe hepatosplenomegaly, anemia, thrombocytopenia and skeletal deterioration.

The gene encoding human GCD was first sequenced in 1985 (6) The protein consists of 497 amino acids derived from a 536-mer pro-peptide. The mature hGCD contains five N-glycosylation amino acid consensus sequences (Asn-X-Ser/Thr). Four of these sites are normally glycosylated. Glycosylation of the first site is essential for the production of active protein. Both high-mannose and complex oligosaccharide chains have been identified (7). hGCD from placenta contains 7% carbohydrate, 20% of which is of the high-mannose type (8). Biochemical and site-directed mutagenesis studies have provided an initial map of regions and residues important to folding, activator interaction, and active site location (9).

Treatment of placental hGCD with neuraminidase (yielding an asialo enzyme) results in increased clearance and uptake rates by rat liver cells with a concomitant increase in hepatic enzymatic activity (Furbish et al., 1981, Biochim. Biophys. Acta 673:425-434). This glycan-modified placental hGC is currently used as a therapeutic agent in the treatment of Gaucher's disease. Biochemical and site-directed mutagenesis studies have provided an initial map of regions and residues important to folding, activator interaction, and active site location [Grace et al., J. Biol. Chem. 269:2283-2291 (1994)].

There are three different types of Gaucher disease, each determined by the level of hGC activity. The major cells affected by the disease are the macrophages, which are highly enlarged due to GlcCer accumulation, and are thus referred to as "Gaucher cells".

The identification of a defect in GCD as the primary cause of Gaucher's disease led to the development of enzyme replacement therapy as a therapeutic strategy for this disorder.

De Duve first suggested that replacement of the missing lysosomal enzyme with exogenous biologically active enzyme might be a viable approach to treatment of lysosomal storage diseases [Fed Proc. 23:1045 (1964)].

Since that time, various studies have suggested that enzyme replacement therapy may be beneficial for treating various lysosomal storage diseases. The best success has been shown with individuals with type I Gaucher disease, who were treated with exogenous enzyme (β-glucocerebrosidase), prepared from placenta (Ceredase™) or, more recently, recombinantly (Cerezyme™).

Unmodified glucocerebrosidase derived from natural sources is a glycoprotein with four carbohydrate chains. This protein does not target the phagocytic cells in the body and is therefore of limited therapeutic value. In developing the current therapy for Gaucher's disease, the terminal sugars on the carbohydrate chains of glucocerebrosidase are sequentially removed by treatment with three different glycosidases. This glycosidase treatment results in a glycoprotein whose terminal sugars consist of mannose residues. Since phagocytes have mannose receptors that recognize glycoproteins and glycopeptides with oligosaccharide chains that terminate in mannose residues, the carbohydrate remodeling of glucocerebrosidase has improved the targeting of the enzyme to these cells [Furbish et al., Biochem. Biophys. Acta 673:425, (1981)].

As indicated herein, glycosylation plays a crucial role in hGCD activity, therefore deglycosylation of hGCD expressed in cell lines using either tunicamycin (Sf9 cells) or point mutations abolishing all glycosylation sites (both Sf9 and COS-1 cells), results in complete loss of enzymatic activity. In addition, hGCD expressed in *E. coli* was found to be inactive. Further research indicated the significance of the various glycosylation sites for protein activity. In addition to the role of glycosylation in the actual protein activity, the commercially produced enzyme contains glycan sequence modifications that facilitate specific drug delivery. The glycosylated proteins are remodeled following extraction to include only mannose containing glycan sequences.

The human GCD enzyme contains 4 glycosylation sites and 22 lysines. The recombinantly produced enzyme (Cerezyme™) differs from the placental enzyme (Ceredase™) in position 495 where an arginine has been substituted with a histidine. Furthermore, the oligosaccharide composition differs between the recombinant and the placental GCD as the former has more fucose and N-acetyl-glucosamine residues while the latter retains one high mannose chain. As mentioned above, both types of GCDs are treated with three different glycosidases (neuraminidase, galactosidase, and P—N acetyl-glucosaminidase) to expose terminal mannoses, which enables targeting of phagocytic cells. A pharmaceutical preparation comprising the recombinantly produced enzyme is described in U.S. Pat. No. 5,549,892. It should be noted that all references mentioned are hereby incorporated by reference as if fully set forth herein.

One drawback associated with existing lysosomal enzyme replacement therapy treatment is that the in vivo bioactivity of the enzyme is undesirably low, e.g. because of low uptake, reduced targeting to lysosomes of the specific cells where the substrate is accumulated, and a short functional in vivo half-life in the lysosomes.

Another major drawback of the existing GCD recombinant enzymes is their expense, which can place a heavy economic burden on health care systems. The high cost of these recombinant enzymes results from a complex purification protocol, and the relatively large amounts of the therapeutic required for existing treatments. There is therefore, an urgent need to reduce the cost of GCD so that this life saving therapy can be provided to all who require it more affordably.

Proteins for pharmaceutical use have been traditionally produced in mammalian or bacterial expression systems. In the past decade a new expression system has been developed in plants. This methodology utilizes *Agrobacterium*, a bacteria capable of inserting single stranded DNA molecules (T-DNA) into the plant genome. Due to the relative simplicity of introducing genes for mass production of proteins and peptides, this methodology is becoming increasingly popular as an alternative protein expression system (1).

While post translational modifications do not exist in bacterial expression systems, plant derived expression systems do facilitate these modifications known to be crucial for protein expression and activity. One of the major differences between mammalian and plant protein expression system is the variation of protein sugar side chains, caused by the differences in biosynthetic pathways. Glycosylation was shown to have a profound effect on activity, folding, stability, solubility, susceptibility to proteases, blood clearance rate and antigenic potential of proteins. Hence, any protein production in plants should take into consideration the potential ramifications of plant glycosylation.

Protein glycosylation is divided into two categories: N-linked and O-linked modifications (2). The two types differ in amino acid to which the glycan moiety is attached to —N-linked are attached to Asn residues, while O-linked are attached to Ser or Thr residues. In addition, the glycan sequences of each type bear unique distinguishing features. Of the two types, N-linked glycosylation is the more abundant, and its effect on protein function has been extensively studied. O-linked glycans, on the other hand are relatively scarce, and less information is available regarding their affect on proteins.

SUMMARY OF THE INVENTION

The background art does not teach or suggest a device, system or method for selectively producing glycosylated proteins in plant culture. The background art also does not teach or suggest such a device, system or method for producing high mannose proteins in plant culture. The background art also does not teach or suggest a device, system or method for producing proteins in plant culture through the endoplasmic reticulum (ER). The background art also does not teach or suggest such a device, system or method for producing proteins in plant culture through the endoplasmic reticulum (ER) while by-passing the Golgi body. The background art also does not teach or suggest such a device, system or method for producing proteins in plant culture by using an ER signal to by-pass the Golgi body.

The present invention overcomes these disadvantages of the background art by providing a device, system and method for producing glycosylated proteins in plant culture, particularly proteins having a high mannose glycosylation, while optionally and preferably targeting (and/or otherwise manipulating processing of) such proteins with an ER signal. Without wishing to be limited by a single hypothesis, it is believed that such targeting causes the proteins to by-pass the Golgi body and thereby to retain the desired glycosylation, particularly high mannose glycosylation. It should be noted that the term "plant culture" as used herein includes any type of transgenic and/or otherwise genetically engineered plant cell that is grown in culture. The genetic engineering may optionally be permanent or transient. Preferably, the culture features cells that are not assembled to form a complete plant, such that at least one biological structure of a plant is not present. Optionally and preferably, the culture may feature a plurality of different types of plant cells, but preferably the culture features a particular type of plant cell. It should be noted that optionally plant cultures featuring a particular type of plant cell may be originally derived from a plurality of different types of such plant cells.

The plant cells may be grown according to any type of suitable culturing method, including but not limited to, culture on a solid surface (such as a plastic culturing vessel or plate for example) or in suspension.

The invention further relates to vectors and methods for expression and production of enzymatically active high mannose lysosomal enzymes using transgenic plant root, particularly carrot cells. More particularly, the invention relates to host cells, particularly transgenic suspended carrot cells, vectors and methods for high yield expression and production of biologically active high mannose Glucocerebrosidase (GCD). The invention further provides for compositions and methods for the treatment of lysosomal storage diseases.

The present invention is also of a device, system and method for providing sufficient quantities of biologically active lysosomal enzymes, and particularly, human GCD, to deficient cells. The present invention is also of host cells comprising new vector compositions that allow for efficient production of genes encoding lysosomal enzymes, such as GCD.

The present invention therefore solves a long-felt need for an economically viable technology to produce proteins having particular glycosylation requirements, such as the high mannose glycosylation of lysosomal enzymes such as GCD for example. The present invention is able to solve this long felt need by using plant cell culture.

In order to further explain the present invention, a brief explanation is now provided of the biosynthetic pathway of high-mannose proteins. The basic biosynthesis pathway of high-mannose and complex N-linked glycans is highly conserved among all eukaryotes. Biosynthesis begins in the Endoplasmic Reticulum (ER) with the transfer of the glycan precursor from a dolichol lipid carrier to a specific Asn residue on the protein by the oligosaccharyl transferase. The precursor is subsequently modified in the ER by glycosidases I and II and a hypothetical mannosidase to yield the high mannose structures, similar to the process occurring in mammals.

Further modifications of the glycan sequence to complex and hybrid structures occur in the Golgi. Such modifications include removal of one of the four mannose residues by α-mannosidase I, addition of an N-acetylglucosamine residue, removal of the two additional mannose residues by α-mannosidase II, addition of N-acetylglucosamine and optionally, at this stage, xylose and fucose residues may be added to yield plant specific N-linked glycans. After the transfer of xylose and fucose to the core, complex type N-glycans can be further processed via the addition of terminal fucose and galactose. Further modifications may take place during the glycoprotein transport.

Several approaches are currently used in the background art to control and tailor protein glycosylation in plants, all of which have significant deficiencies, particularly in comparison to the present invention. Gross modifications, such as complete inhibition of glycosylation or the removal of glycosylation sites from the peptide chain is one strategy. However, this approach can result in structural defects. An additional approach involves knock-out and introduction of specific carbohydrate processing enzymes. Again, this approach is difficult and may also have detrimental effects on the plant cells themselves.

The present invention overcomes these deficiencies of the background art approaches by using an ER signal and/or by blocking secretion from the ER to the Golgi body. Without wishing to be limited by a single hypothesis, since a high mannose structure of lysosomal enzymes is preferred, if secretion can be blocked and the protein can be maintained in the ER, naturally occurring high mannose structures are obtained without the need for remodeling.

As indicated above, proteins transported via the endomembrane system first pass into the endoplasmic reticulum. The necessary transport signal for this step is represented by a signal sequence at the N-terminal end of the molecule, the so-called signal peptide. As soon as this signal peptide has fulfilled its function, which is to insert the precursor protein attached to it into the endoplasmic reticulum, it is split off proteolytically from the precursor protein. By virtue of its specific function, this type of signal peptide sequence has been conserved to a high degree during evolution in all living cells, irrespective of whether they are bacteria, yeasts, fungi, animals or plants.

Many plant proteins, which are inserted into the endoplasmic reticulum by virtue of the signal peptide do not reside in the ER, but are transported from the endoplasmic reticulum to the Golgi and continue trafficking from the Golgi to the vacuoles. One class of such sorting signals for this traffic resides are signals that reside on the C-terminal part of the precursor protein [Neuhaus and Rogers, (1998) Plant Mol. Biol. 38:127-144]. Proteins containing both an N-terminal signal peptide for insertion into the endoplasmic reticulum and a C-terminal vacuolar targeting signal are expected to contain complex glycans, which is attached to them in the Golgi [Lerouge et al., (1998) Plant Mol. Biol. 38:31-48]. The nature of such C-terminal sorting signals can vary very widely. U.S. Pat. No. 6,054,637 describes peptide fragments obtained from the region of tobacco basic chitinase, which is a vacuolar protein that act as vacuolar targeting peptides. An example for a vacuolar protein containing a C-terminal targeting signal and complex glycans is the phaseolin storage protein from bean seeds [Frigerio et al., (1998) Plant Cell 10:1031-1042; Frigerio et al., (2001) Plant Cell 13:1109-1126.].

The paradigm is that in all eukaryotic cells vacuolar proteins pass via the ER and the Golgi before sequestering in the vacuole as their final destination. Surprisingly, the transformed plant root cells of the present invention produced an unexpected high mannose GCD. Advantageously, this high mannose product was found to be biologically active and therefore no further steps were needed for its activation. Without wishing to be limited by a single hypothesis, it would appear that the use of an ER signal with the recombinant protein being produced in plant cell culture was able to overcome transportation to the Golgi, and hence to retain the desired high mannose glycosylation. Optionally, any type of mechanism which is capable to produce high mannose glycosylation, including any type of mechanism to by-pass the Golgi, may be used in accordance with the present invention.

In a first aspect, the present invention relates to a host cell producing a high mannose recombinant protein of interest. This cell may be transformed or transfected with a recombinant nucleic acid molecule encoding a protein of interest or with an expression vector comprising the nucleic acid molecule. Such nucleic acid molecule comprises a first nucleic acid sequence encoding the protein of interest operably linked to a second nucleic acid sequence encoding a vacuolar targeting signal peptide. The first nucleic acid sequence may be optionally further operably linked to a third nucleic acid sequence encoding an ER (endoplasmic reticulum) targeting signal peptide. The host cell of the invention is characterized in that the protein of interest is produced by the cell in a highly mannosylated form.

The host cell of the invention may be a eukaryotic or prokaryotic cell.

In one embodiment, the host cell of the invention is a prokaryotic cell, preferably, a bacterial cell, most preferably, an *Agrobacterium tumefaciens* cell. These cells are used for infecting the preferred plant host cells described below.

In another preferred embodiment, the host cell of the invention may be a eukaryotic cell, preferably, a plant cell, and most preferably, a plant root cell selected from the group consisting of *Agrobacterium rihzogenes* transformed root cell, celery cell, ginger cell, horseradish cell and carrot cell.

In a preferred embodiment, the plant root cell is a carrot cell. It should be noted that the transformed carrot cells of the invention are grown in suspension. As mentioned above and described in the Examples, these cells were transformed with the *Agrobacterium tumefaciens* cells.

In another embodiment, the recombinant nucleic acid molecule comprised within the host cell of the invention, comprises a first nucleic acid sequence encoding a lysosomal enzyme that is in operable linkage with a second nucleic acid sequence encoding a vacuolar targeting signal peptide derived from the basic tobacco chitinase A gene. This vacuolar signal peptide has the amino acid sequence as denoted by SEQ ID NO: 2. The first nucleic acid sequence may be optionally further linked in an operable linkage with a third nucleic acid sequence encoding an ER (endoplasmic reticulum) targeting signal peptide as denoted by SEQ ID NO: 1. In one embodiment, the recombinant nucleic acid molecule comprised within the host cell of the invention further comprises a promoter that is functional in plant cells. This promoter should be operably linked to the recombinant molecule of the invention.

In another embodiment, this recombinant nucleic acid molecule may optionally further comprise an operably linked terminator which is preferably functional in plant cells. The recombinant nucleic acid molecule of the invention may optionally further comprise additional control, promoting and regulatory elements and/or selectable markers. It should be noted that these regulatory elements are operably linked to the recombinant molecule.

In a preferred embodiment, the high mannose protein of interest produced by the host cell of the invention may be a high mannose glycoprotein having exposed mannose terminal residues.

Such high mannose protein may be according to another preferred embodiment, a lysosomal enzyme selected from the group consisting of glucocerebrosidase (GCD), acid sphingomyelinase, hexosaminidase, α-N-acetylgalactosaminidise, acid lipase, α-galactosidase, glucocerebrosidase, α-L-iduronidase, iduronate sulfatase, α-mannosidase and sialidase. In a preferred embodiment, the lysosomal enzyme may be the human glucocerebrosidase (GCD). Hereinafter recombinant GCD, rGCD, rhGCD all refer to various forms of recombinant human GCD unless otherwise indicated.

As previously described, Gaucher's disease, the most prevalent lysosomal storage disorder, is caused by point mutations in the hGCD (human glucocerebrosidase) gene (GBA), which result in accumulation of GlcCer in the lysosomes of macrophages. The identification of GCD deficiency as the primary cause of Gaucher's disease led to the development of enzyme replacement therapy as a therapeutic strategy for this disorder. However, glycosylation plays a crucial role in hGCD activity and uptake to target cells.

Therefore, according to other preferred embodiments of the present invention, suitably glycosylated hGCD is preferably provided by controlling the expression of hGCD in plant cell culture, optionally and more preferably by providing an ER signal and/or otherwise by optionally and more preferably blocking transportation to the Golgi.

Optionally and preferably, the hGCD has at least one oligosaccharide chain comprising an exposed mannose residue for the treatment or prevention of Gaucher's disease.

Still further, in a particular embodiment, this preferred host cell is transformed or transfected by a recombinant nucleic acid molecule which further comprises an $^{35}S$ promoter from Cauliflower Mosaic Virus, an octopine synthase terminator of *Agrobacterium tumefaciens* and TMV (Tobacco Mosaic Virus) omega translational enhancer element. According to a preferred embodiment, this recombinant nucleic acid molecule comprises the nucleic acid sequence substantially as denoted by SEQ ID NO: 13 and encodes a high mannose GCD having the amino acid sequence substantially as denoted by SEQ ID NOs: 14 or 15.

It should be appreciated that the present invention further provides for an expression vector comprising a nucleic acid molecule encoding a biologically active lysosomal enzyme.

In one preferred embodiment, the expression vector of the invention comprises a nucleic acid molecule encoding a biologically active high mannose human glucocerebrosidase (GCD). Preferably, this preferred expression vector comprises a nucleic recombinant nucleic acid molecule which having the nucleic acid sequence substantially as denoted by SEQ ID NO: 13.

In a second aspect, the present invention relates to a recombinant high mannose protein produced by the host cell of the invention.

In a preferred embodiment, this high mannose protein may be a biologically active high mannose lysosomal enzyme selected from the group consisting of glucocerebrosidase (GCD), acid sphingomyelinase, hexosaminidase, α-N-acetylgalactosaminidise, acid lipase, α-galactosidase, glucocerebrosidase, α-L-iduronidase, iduronate sulfatase, α-mannosidase and sialidase. Most preferably, this lysosomal enzyme may be human glucocerebrosidase (GCD).

Still further, the invention provides for a recombinant biologically active high mannose lysosomal enzyme having at least one oligosaccharide chain comprising an exposed mannose residue.

According to a preferred embodiment, the recombinant lysosomal enzyme of the invention can bind to a mannose receptor on a target cell in a target site. Preferably, this site may be within a subject suffering from a lysosomal storage disease.

It should be noted that the recombinant lysosomal enzyme has increased affinity for the target cell, in comparison with the corresponding affinity of a naturally occurring lysosomal enzyme for the target cell. In a specific embodiment, the target cell at the target site may be a Kupffer cell in the liver of the subject.

In a preferred embodiment, the recombinant lysosomal enzyme may be selected from the group consisting of glucocerebrosidase (GCD), acid sphingomyelinase, hexosaminidase, α-N-acetylgalactosaminidise, acid lipase, α-galactosidase, glucocerebrosidase, α-L-iduronidase, iduronate sulfatase, α-mannosidase or sialidase.

Most preferably, this recombinant lysosomal enzyme is glucocerebrosidase (GCD).

In a third aspect, the invention relates to a method of producing a high mannose protein. Accordingly, the method of the invention comprises the steps of: (a) preparing a culture of recombinant host cells transformed or transfected with a recombinant nucleic acid molecules encoding a recombinant protein of interest or with an expression vector comprising the recombinant nucleic acid molecules; (b) culturing these host cell culture prepared by step (a) under conditions permitting the expression of the protein, wherein the host cells produce the protein in a highly mannosylated form; (c) recovering the protein from the cells and harvesting the cells from the culture provided in (a); and (d) purifying the protein of step (c) by a suitable protein purification method.

According to a preferred embodiment, the host cell used by this method is the host cell of the invention.

In another preferred embodiment, the high mannose protein produced by the method of the invention may be a biologically active high mannose lysosomal enzyme having at least one oligosaccharide chain comprising an exposed mannose residue.

This recombinant enzyme can bind to a mannose receptor on a target cell in a target site. More particularly, the recombinant enzyme produced by the method of the invention has increased affinity for the target cell, in comparison with the corresponding affinity of a naturally occurring lysosomal enzyme to the target cell. Accordingly, the target cell at the target site may be Kupffer cell in the liver of the subject.

In a specific embodiment, this lysosomal enzyme may be selected from the group consisting of glucocerebrosidase (GCD), acid sphingomyelinase, hexosaminidase, α-N-acetylgalactosaminidise, acid lipase, α-galactosidase, glucocerebrosidase, α-L-iduronidase, iduronate sulfatase, α-mannosidase and sialidase. Most preferably, this lysosomal enzyme may be glucocerebrosidase (GCD).

In another preferred embodiment, the host cell used by the method of the invention may be a plant root cell selected from the group consisting of *Agrobacterium rihzogenes* transformed root cell, celery cell, ginger cell, horseradish cell and carrot cell. Most preferably, the plant root cell is a carrot cell. It should be particularly noted that in the method of the invention, the transformed host carrot cells are grown in suspension.

In a further aspect, the present invention relates to a method for treating a subject having lysosomal storage disease using exogenous recombinant lysosomal enzyme, comprising: (a) providing a recombinant biologically active form of lysosomal enzyme purified from transformed plant root cells, and capable of efficiently targeting cells abnormally deficient in the lysosomal enzyme. This recombinant biologically active enzyme has exposed terminal mannose residues on appended oligosaccharides; and (b) administering a therapeutically effective amount of the recombinant biologically active lysosomal enzyme to the subject. In a preferred embodiment, the recombinant high mannose lysosomal enzyme used by the method of the invention may be produced by the host cell of the invention. Preferably, this host cell is a carrot cell.

In another preferred embodiment, the lysosomal enzyme used by the method of the invention may be a high mannose enzyme comprising at least one oligosaccharide chain having an exposed mannose residue. This recombinant enzyme can bind to a mannose receptor on a target cell in a target site within a subject. More preferably, this recombinant lysosomal enzyme has increased affinity for these target cells, in comparison with the corresponding affinity of a naturally occurring lysosomal enzyme to the target cell.

More specifically, the lysosomal enzyme used by the method of the invention may be selected from the group consisting of glucocerebrosidase (GCD), acid sphingomyelinase, hexosaminidase, α-N-acetylgalactosaminidise, acid lipase, α-galactosidase, glucocerebrosidase, α-L-iduronidase, iduronate sulfatase, α-mannosidase or sialidase. Preferably, this lysosomal enzyme is glucocerebrosidase (GCD).

According to a preferred embodiment, the method of the invention is therefore intended for the treatment of a lysosomal storage disease, particularly Gaucher's disease.

In such case the target cell at the target site may be a Kupffer cell in the liver of the subject.

The invention further provides for a pharmaceutical composition for the treatment of a lysosomal storage disease comprising as an active ingredient a recombinant biologically active high mannose lysosomal enzyme as defined by the invention. The composition of the invention may optionally further comprise pharmaceutically acceptable dilluent, carrier or excipient.

In a specific embodiment, the composition of the invention is intended for the treatment of Gaucher's disease. Such composition may preferably comprise as an effective ingredient a biologically active high mannose human glucocerebrosidase (GCD), as defined by the invention.

The invention further relates to the use of a recombinant biologically active high mannose lysosomal enzyme of the invention in the manufacture of a medicament for the treatment or prevention of a lysosomal storage disease. More particularly, such disease may be Gaucher's disease.

Accordingly, this biologically active lysosomal enzyme is a biologically active high mannose human glucocerebrosidase (GCD), as defined by the invention.

According to the present invention, there is provided a host cell producing a high mannose recombinant protein, comprising a polynucleotide encoding the recombinant protein and a signal for causing the recombinant protein to be produced as a high mannose protein. Preferably, the polynucleotide comprises a first nucleic acid sequence encoding the protein of interest operably linked to a second nucleic acid sequence encoding a signal peptide. Optionally, the signal peptide comprises an ER (endoplasmic reticulum) targeting signal peptide. Preferably, the polynucleotide further comprises a third nucleic acid sequence for encoding a vacuolar targeting signal peptide.

Preferably, the signal causes the recombinant protein to be targeted to the ER. More preferably, the signal comprises a signal peptide for causing the recombinant protein to be targeted to the ER. Most preferably, the polynucleotide comprises a nucleic acid segment for encoding the signal peptide.

Optionally and preferably, the signal causes the recombinant protein to by-pass the Golgi. Preferably, the signal comprises a signal peptide for causing the recombinant protein to not be targeted to the Golgi. More preferably, the polynucleotide comprises a nucleic acid segment for encoding the signal peptide.

Optionally and preferably, the host cell is any one of a eukaryotic and a prokaryotic cell. Optionally, the prokaryotic cell is a bacterial cell, preferably an *Agrobacterium tumefaciens* cell. Preferably, the eukaryotic cell is a plant cell. More preferably, the plant cell is a plant root cell selected from the group consisting of *Agrobacterium rihzogenes* transformed root cell, celery cell, ginger cell, horseradish cell and carrot cell. Most preferably, the plant root cell is a carrot cell.

Preferably, the recombinant polynucleotide comprises a first nucleic acid sequence encoding the protein of interest that is in operable link with a second nucleic acid sequence encoding a vacuolar targeting signal peptide derived from the basic tobacco chitinase A gene, which vacuolar signal peptide has the amino acid sequence as denoted by SEQ ID NO: 2, wherein the first nucleic acid sequence is optionally further operably linked to a third nucleic acid sequence encoding an ER (endoplasmic reticulum) targeting signal peptide as denoted by SEQ ID NO: 1.

More preferably, the recombinant polynucleotide further comprises a promoter that is functional in plant cells, wherein the promoter is operably linked to the recombinant molecule.

Most preferably, the recombinant polynucleotide further comprises a terminator that is functional in plant cells, wherein the terminator is operably linked to the recombinant molecule.

Also most preferably, the recombinant polynucleotide optionally further comprises additional control, promoting and regulatory elements and/or selectable markers, wherein the regulatory elements are operably linked to the recombinant molecule.

Preferably, the high mannose protein is a high mannose glycoprotein having glycosylation with at least one exposed mannose residue. More preferably, the high mannose protein is a biologically active high mannose lysosomal enzyme selected from the group consisting of glucocerebrosidase (GCD), acid sphingomyelinase, hexosaminidase, α-N-acetylgalactosaminidise, acid lipase, α-galactosidase, glucocerebrosidase, α-L-iduronidase, iduronate sulfatase, α-mannosidase and sialidase Most preferably, the lysosomal enzyme is human glucocerebrosidase (GCD).

Preferably, the GCD comprises the amino acid sequence substantially as denoted by SEQ ID NO: 8, encoded by the nucleic acid sequence as denoted by SEQ ID NO: 7.

More preferably, the cell is transformed or transfected with a recombinant polynucleotide or with an expression vector comprising the molecule, which recombinant polynucleotide further comprises an $^{35}S$ promoter from Cauliflower Mosaic Virus, an octopine synthase terminator of *Agrobacterium tumefaciens*, and the regulatory element is the TMV (Tobacco Mosaic Virus) omega translational enhancer element, and having the nucleic acid sequence substantially as denoted by SEQ ID NO: 13 encoding GCD having the amino acid sequence substantially as denoted by SEQ ID NOs: 14 or 15.

According to preferred embodiments, there is provided a recombinant high mannose protein produced by the host cell described above.

Preferably, the high mannose protein is a biologically active high mannose lysosomal enzyme selected from the group consisting of glucocerebrosidase (GCD), acid sphingomyelinase, hexosaminidase, α-N-acetylgalactosaminidise, acid lipase, α-galactosidase, glucocerebrosidase, α-L-iduronidase, iduronate sulfatase, α-mannosidase and sialidase.

More preferably, the lysosomal enzyme is human glucocerebrosidase (GCD).

According to other preferred embodiments of the present invention, there is provided a recombinant biologically active high mannose lysosomal enzyme having at least one oligosaccharide chain comprising an exposed mannose residue.

According to still other preferred embodiments, there is provided a recombinant protein, comprising a first portion having signal peptide activity and a second portion having lysosomal enzyme activity, the first portion causing the second portion to be processed in a plant cell with at least one oligosaccharide chain comprising an exposed mannose residue.

Preferably, the lysosomal enzyme comprises a protein for the treatment or prevention of Gaucher's disease.

More preferably, the protein comprises hGCD.

Preferably, the first portion comprises a plant cell ER targeting signal peptide. More preferably, the recombinant enzyme can bind to a mannose receptor on a target cell in a target site within a subject suffering from a lysosomal storage disease. Most preferably, the recombinant lysosomal enzyme has increased affinity for the target cell, in comparison with the corresponding affinity of a naturally occurring lysosomal enzyme for the target cell.

Also most preferably, the recombinant lysosomal enzyme is selected from the group consisting of glucocerebrosidase (GCD), acid sphingomyelinase, hexosaminidase, α-N-acetylgalactosaminidise, acid lipase, α-galactosidase, glucocerebrosidase, α-L-iduronidase, iduronate sulfatase, α-mannosidase or sialidase.

Preferably, the recombinant lysosomal enzyme is glucocerebrosidase (GCD).

Also preferably, the target cell at the target site is a Kupffer cell in the liver of the subject.

According to still other preferred embodiments there is provided a recombinant high mannose protein, produced in plant cell culture. Preferably, the protein features a plant signal peptide for targeting a protein to the ER.

More preferably, the plant signal peptide comprises a peptide for targeting the protein to the ER in a root plant cell culture. Most preferably, the root plant cell culture comprises carrot cells.

According to yet other preferred embodiments there is provided a recombinant high mannose hGCD protein, produced in plant cell culture.

According to still other preferred embodiments there is provided use of a plant cell culture for producing a high mannose protein.

According to other preferred embodiments there is provided a method of producing a high mannose protein comprising: preparing a culture of recombinant host cells transformed or transfected with a recombinant polynucleotide encoding for a recombinant protein; culturing the host cell culture under conditions permitting the expression of the protein, wherein the host cells produce the protein in a highly mannosylated form.

Preferably, the host cell culture is cultured in suspension. More preferably, the method further comprises purifying the protein.

According to other preferred embodiments, the method is performed with the host cell as previously described. Preferably, the high mannose protein is a biologically active high mannose lysosomal enzyme having at least one oligosaccharide chain comprising an exposed mannose residue. More preferably, the recombinant enzyme binds to a mannose receptor on a target cell in a target site. Most preferably, the recombinant enzyme has increased affinity for the target cell, in comparison with the corresponding affinity of a naturally occurring lysosomal enzyme to the target cell.

Preferably, the lysosomal enzyme is selected from the group consisting of glucocerebrosidase (GCD), acid sphingomyelinase, hexosaminidase, α-N-acetylgalactosaminidise, acid lipase, α-galactosidase, glucocerebrosidase, α-L-iduronidase, iduronate sulfatase, α-mannosidase and sialidase.

More preferably, the lysosomal enzyme is glucocerebrosidase (GCD). Most preferably, the target cell at the target site is Kupffer cell in the liver of the subject.

Preferably, the host cell is a plant root cell selected from the group consisting of *Agrobacterium rihzogenes* transformed root cell, celery cell, ginger cell, horseradish cell and carrot cell.

More preferably, the plant root cell is a carrot cell.

Most preferably, the transformed host carrot cells are grown in suspension.

According to still other preferred embodiments there is provided a method for treating a subject having lysosomal storage disease using exogenous recombinant lysosomal enzyme, comprising: providing a recombinant biologically active form of lysosomal enzyme purified from transformed plant root cells, and capable of efficiently targeting cells abnormally deficient in the lysosomal enzyme, wherein the recombinant biologically active enzyme has exposed terminal mannose residues on appended oligosaccharides; and administering a therapeutically effective amount of the recombinant biologically active lysosomal enzyme to the subject. This method may optionally be performed with any host cell and/or protein as previous described.

Preferably, the recombinant enzyme can bind to a mannose receptor on a target cell in a target site within a subject. More preferably, the recombinant lysosomal enzyme has increased affinity for the target cell, in comparison with the corresponding affinity of a naturally occurring lysosomal enzyme to the target cell. Most preferably, the lysosomal enzyme is selected from the group consisting of glucocerebrosidase (GCD), acid sphingomyelinase, hexosaminidase, α-N-acetylgalactosaminidise, acid lipase, α-galactosidase, glucocerebrosidase, α-L-iduronidase, iduronate sulfatase, α-mannosidase or sialidase. Also most preferably, the lysosomal enzyme is glucocerebrosidase (GCD).

Also most preferably, the lysosomal storage disease is Gaucher's disease. Also most preferably, the target cell at the target site is a Kupffer cell in the liver of the subject.

According to still other preferred embodiments there is provided a pharmaceutical composition for the treatment of a lysosomal storage disease comprising as an active ingredient a recombinant biologically active high mannose lysosomal enzyme as described above, which composition optionally further comprises pharmaceutically acceptable dilluent, carrier or excipient. Preferably, the lysosomal storage disease is Gaucher's disease. More preferably, the recombinant lysosomal enzyme is a biologically active high mannose human glucocerebrosidase (GCD).

According to still other preferred embodiments there is provided the use of a recombinant biologically active high mannose lysosomal enzyme as described above, in the manufacture of a medicament for the treatment or prevention of a lysosomal storage disease. Preferably, the disease is Gaucher's disease. More preferably, the biologically active lysosomal enzyme is a biologically active high mannose human glucocerebrosidase (GCD).

The invention will be further described on the hand of the following figures, which are illustrative only and do not limit the scope of the invention which is also defined by the appended claims.

BRIEF DESCRIPTION OF THE FIGURES

The patent or application file contains at least one drawing executed in color. Copies of this patent or patent application publication with color drawing(s) will be provided by the Office upon request and payment of the necessary fee.

The invention is herein described, by way of example only, with reference to the accompanying drawings, wherein:

FIG. 1A shows the resulting expression cassette comprising $^{35}$S promoter from Cauliflower Mosaic Virus, TMV (Tobacco Mosaic Virus) omega translational enhancer element, ER targeting signal, the human GCD sequence (also denoted by SEQ ID NO: 7), vacuolar signal and octopine synthase terminator sequence from *Agrobacterium tumefaciens*.

FIG. 1B shows a schematic map of pGreenll plasmid backbone.

FIG. 3A represents a standard run of this purification step. The fractions collected during the run were monitored by enzyme activity assay, as shown by FIG. 3B, and tubes exhibiting enzymatic activity (in the elution peak) were pooled. FIG. 3C shows coomassie-blue stain of elution fractions assayed for activity.

FIG. 4A represents a standard run of this purification step.

FIG. 4B shows the fractions collected during the run that were monitored by enzyme activity assay.

FIG. 4C shows coomassie-blue stain of elution fractions assayed for activity.

FIG. 5 shows activity of recombinant hGCD following uptake by peritoneal macrophages (FIGS. 5A-5C), while FIG. 5D shows a Western blot of recombinant GCD according to the present invention.

FIG. 9a is a Coomassie blue stained SDS-PAGE analysis of the plant produced hGCD of the invention (lanes 1 and 2, 5 and 10 µg of protein, respectively) and Cerezyme®, (lanes 3 and 4, 5 and 10 µg protein, respectively). FIG. 9b is a Western blot analysis of SDS-PAGE separated recombinant human GCD (lanes 1 and 2, 50 and 10 ng respectively) of the present invention compared to the commercial Cerezyme® enzyme. SDS-PAGE-separated proteins were blotted onto nitrocellulose (lanes 3 and 4, 50 and 100 ng antigen, respectively), and immunodetected using a polyclonal anti-GCD antibody and peroxidase-conjugated goat anti-rabbit HRP secondary antibody. Note the consistency of size and immune reactivity between the plant recombinant GCD of the present invention and the mammalian-cell (CHO) prepared enzyme (Cerezyme®). MW=molecular weight standard markers.

FIG. 10a shows the results of a major glycan structure analysis of the GCD, indicating all structures and their relative amounts based on HPLC, enzyme array digests and MALDI. Retention time of individual glycans is compared to the retention times of a standard partial hydrolysis of dextran giving a ladder of glucose units (GU). FIG. 10b shows the glycan structures of the mammalian-cell (CHO) prepared enzyme (Cerezyme®), before and after the in-vitro modification process. Note the predominance of the xylose and exposed mannose glycosides in the recombinant human GCD of the present invention.

DETAILED DESCRIPTION OF THE INVENTION

Figure 1A:
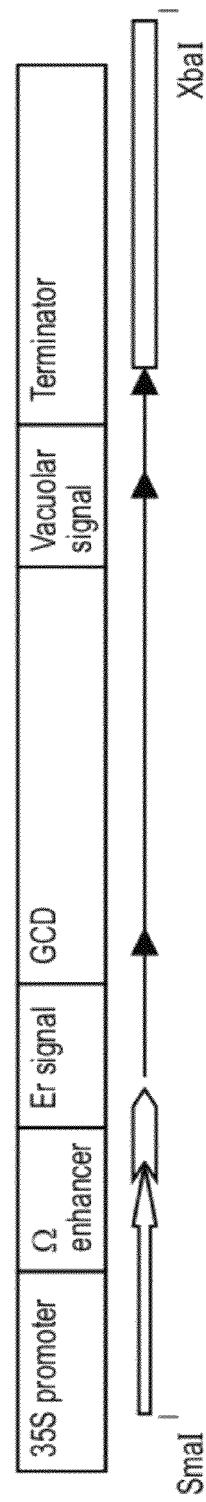
FIG. 1A-1B.

Proteins for pharmaceutical use have been traditionally produced in mammalian or bacterial expression systems. In the past few years a promising new expression system was found in plants. Due to the relative simplicity of introducing new genes and potential for mass production of proteins and peptides, 'molecular pharming' is becoming increasingly popular as a protein expression system.

One of the major differences between mammalian and plant protein expression system is the variation of protein glycosylation sequences, caused by the differences in biosynthetic pathways. Glycosylation was shown to have a profound effect on activity, folding, stability, solubility, susceptibility to proteases, blood clearance rate and antigenic potential of proteins. Hence, any protein production in plants should take into consideration the potential ramifications of plant glycosylation.

This is well illustrated by the difficulties encountered in previous attempts to produce biologically active mammalian proteins in plants. For example, U.S. Pat. No. 5,929,304, to Radin et al (Crop Tech, Inc) discloses the production, in tobacco plants, of a human α-L-iduronase (IDUA) and a glucocerebrosidase (hGC), by insertion of the relevant human lysosomal enzyme coding sequences into an expression cassette for binary plasmid for *A. tumefaciens*-mediated transformation of tobacco plants. Despite demonstration of recombinant human lysosomal protein production in the transgenic plants, and the detection of catalytic activity in the recombinant protein, no binding to or uptake into target cells was disclosed, and the lysosomal enzyme compositions remained unsuitable for therapeutic applications, presumably due to the absence of accurate glycosylation of the protein, and subsequent inability of the polypeptides to interact efficiently with their target cells/tissue though a specific receptor.

Carbohydrate moiety is one of the most common post-translational modifications of proteins. Protein glycosylation is divided into two categories: N-linked and O-linked. The two types differ in amino acid to which the glycan moiety is attached on protein —N-linked are attached to Asn residues, while O-linked are attached to Ser or Thr residues. In addition, the glycan sequences of each type bear unique distinguishing features. Of the two types, N-linked glycosylation is the more abundant, and its effect on proteins has been extensively studied. O-linked glycans, on other hand are relatively scarce, and less information is available regarding their influence on proteins. The majority of data available on protein glycosylation in plants focuses on N-linked, rather than O-linked glycans.

The present invention describes herein a plant expression system based on transgenic plant cells, which are preferably root cells, optionally and preferably grown in suspension. This expression system is particularly designed for efficient production of a high mannose protein of interest. The term "high mannose" includes glycosylation having at least one exposed mannose residue.

Thus, in a first aspect, the present invention relates to a host cell producing a high mannose recombinant protein of interest. Preferably, the recombinant protein features an ER (endoplasmic reticulum) signal peptide, more preferably an ER targeting signal peptide. Alternatively or additionally, the recombinant protein features a signal that causes the protein to by-pass the Golgi. The signal preferably enables the recombinant protein to feature high mannose glycosylation, more preferably by retaining such glycosylation, and most preferably by targeting the ER and/or by by-passing the Golgi. As described in greater detail herein, such a signal is preferably implemented as a signal peptide, which more preferably forms part of the protein sequence, optionally and more preferably through engineering the protein to also feature the signal peptide as part of the protein. It should be noted that the signal may optionally be a targeting signal, a retention signal, an avoidance (by-pass) signal, or any combination thereof, or any other type of signal capable of providing the desired high mannose glycosylation structure.

Without wishing to be limited by a single hypothesis, it would appear that the use of an ER targeting signal with the recombinant protein being produced in plant cell culture was able to overcome transportation to the Golgi, and hence to retain the desired high mannose glycosylation. Optionally, any type of mechanism which is capable to produce high mannose glycosylation, including any type of mechanism to by-pass the Golgi, may be used in accordance with the present invention. ER targeting signal peptides are well known in the art; they are N-terminal signal peptides. Optionally any suitable ER targeting signal peptide may be used with the present invention.

A host cell according to the present invention may optionally be transformed or transfected (permanently and/or transiently) with a recombinant nucleic acid molecule encoding a protein of interest or with an expression vector comprising the nucleic acid molecule. Such nucleic acid molecule comprises a first nucleic acid sequence encoding the protein of interest, optionally and preferably operably linked to a second nucleic acid sequence encoding a vacuolar targeting signal peptide. It should be noted that as used herein, the term "operably" linked does not necessarily refer to physical linkage. The first nucleic acid sequence may optionally and preferably further be operably linked to a third nucleic acid sequence encoding an ER (endoplasmic reticulum) targeting signal peptide. In one embodiment, the cell of the invention is characterized in that the protein of interest is produced by the cell in a form that includes at least one exposed mannose residue, but is preferably a highly mannosylated form. In a more preferred embodiment, the cell of the protein of interest is produced by the cell in a form that includes an exposed mannose and at least one xylose residue, in yet a more preferred embodiment, in a form that further includes an exposed mannose and at least one fucose residue. In a most preferred embodiment, the protein is produced by the cell in a form that includes an exposed mannose, a core α (1,2) xylose residue and a core α-(1,3) fucose residue.

"Cells", "host cells" or "recombinant host cells" are terms used interchangeably herein. It is understood that such terms refer not only to the particular subject cells but to the progeny or potential progeny of such a cell. Because certain modifications may occur in succeeding generation due to either mutation or environmental influences, such progeny may not, in fact, be identical to the parent cell, but are still included within the scope of the term as used herein. "Cell" or "host cell" as used herein refers to cells which can be transformed with naked DNA or expression vectors constructed using recombinant DNA techniques. As used herein, the term "transfection" means the introduction of a nucleic acid, e.g., naked DNA or an expression vector, into a recipient cells by nucleic acid-mediated gene transfer. "Transformation", as used herein, refers to a process in which a cell's genotype is changed as a result of the cellular uptake of exogenous DNA or RNA, and, for example, the transformed cell expresses a recombinant form of the desired protein.

It should be appreciated that a drug resistance or other selectable marker is intended in part to facilitate the selection of the transformants. Additionally, the presence of a selectable marker, such as drug resistance marker may be of use in keeping contaminating microorganisms from multiplying in the culture medium. Such a pure culture of the transformed host cell would be obtained by culturing the cells under conditions which are required for the induced phenotype's survival.

As indicated above, the host cells of the invention may be transfected or transformed with a nucleic acid molecule. As used herein, the term "nucleic acid" refers to polynucleotides such as deoxyribonucleic acid (DNA), and, where appropriate, ribonucleic acid (RNA). The terms should also be understood to include, as equivalents, analogs of either RNA or DNA made from nucleotide analogs, and, as applicable to the embodiment being described, single-stranded (such as sense or antisense) and double-stranded polynucleotides.

In yet another embodiment, the cell of the invention may be transfected or transformed with an expression vector comprising the recombinant nucleic acid molecule. "Expression Vectors", as used herein, encompass vectors such as plasmids, viruses, bacteriophage, integratable DNA fragments, and other vehicles, which enable the integration of DNA fragments into the genome of the host. Expression vectors are typically self-replicating DNA or RNA constructs containing the desired gene or its fragments, and operably linked genetic control elements that are recognized in a suitable host cell and effect expression of the desired genes. These control elements are capable of effecting expression within a suitable host. Generally, the genetic control elements can include a prokaryotic promoter system or a eukaryotic promoter expression control system. Such system typically includes a transcriptional promoter, an optional operator to control the onset of transcription, transcription enhancers to elevate the level of RNA expression, a sequence that encodes a suitable ribosome binding site, RNA splice junctions, sequences that terminate transcription and translation and so forth. Expression vectors usually contain an origin of replication that allows the vector to replicate independently of the host cell.

Plasmids are the most commonly used form of vector but other forms of vectors which serves an equivalent function and which are, or become, known in the art are suitable for use herein. See, e.g., Pouwels et al. Cloning Vectors: a Laboratory Manual (1985 and supplements), Elsevier, N.Y.; and Rodriquez, et al. (eds.) Vectors: a Survey of Molecular Cloning Vectors and their Uses, Buttersworth, Boston, Mass. (1988), which are incorporated herein by reference.

In general, such vectors contain, in addition, specific genes which are capable of providing phenotypic selection in transformed cells. The use of prokaryotic and eukaryotic viral expression vectors to express the genes coding for the polypeptides of the present invention are also contemplated.

Optionally, the vector may be a general plant vector (as described with regard to the Examples below). Alternatively, the vector may optionally be specific for root cells.

In one preferred embodiment, the cell of the invention may be a eukaryotic or prokaryotic cell.

In a specific embodiment, the cell of the invention is a prokaryotic cell, preferably, a bacterial cell, most preferably, an *Agrobacterium tumefaciens* cell. These cells are used for infecting the preferred plant host cells described below.

In another preferred embodiment, the cell of the invention may be a eukaryotic cell, preferably, a plant cell, and most preferably, a plant root cell selected from the group consisting of *Agrobacterium rihzogenes* transformed plant root cell, celery cell, ginger cell, horseradish cell and carrot cell.

In a preferred embodiment, the plant root cell is a carrot cell. It should be noted that the transformed carrot cells of the invention are grown in suspension. As mentioned above and described in the Examples, these cells were transformed with the *Agrobacterium tumefaciens* cells of the invention.

The expression vectors or recombinant nucleic acid molecules used for transfecting or transforming the host cells of the invention may be further modified according to methods known to those skilled in the art to add, remove, or otherwise modify peptide signal sequences to alter signal peptide cleavage or to increase or change the targeting of the expressed lysosomal enzyme through the plant endomembrane system. For example, but not by way of limitation, the expression construct can be specifically engineered to target the lysosomal enzyme for secretion, or vacuolar localization, or retention in the endoplasmic reticulum (ER).

In one embodiment, the expression vector or recombinant nucleic acid molecule can be engineered to incorporate a nucleotide sequence that encodes a signal targeting the lysosomal enzyme to the plant vacuole. For example, and not by way of limitation, the recombinant nucleic acid molecule comprised within the host cell of the invention, comprises a first nucleic acid sequence encoding a lysosomal enzyme that is in operable linkage with a second nucleic acid sequence encoding a vacuolar targeting signal peptide derived from the basic tobacco chitinase A gene. This vacuolar signal peptide has the amino acid sequence as denoted by SEQ ID NO: 2. The first nucleic acid sequence may be optionally further linked in an operable linkage with a third nucleic acid sequence encoding an ER (endoplasmic reticulum) targeting signal peptide as denoted by SEQ ID NO: 1. In one embodiment, the recombinant nucleic acid molecule comprised within the host cell of the invention further comprises a promoter that is functional in plant cells. This promoter should be operably linked to the recombinant molecule of the invention.

The term "operably linked" is used herein for indicating that a first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Optionally and preferably, operably linked DNA sequences are contiguous (e.g. physically linked) and, where necessary to join two protein-coding regions, in the same reading frame. Thus, a DNA sequence and a regulatory sequence(s) are connected in such a way as to permit gene expression when the appropriate molecules (e.g., transcriptional activator proteins) are bound to the regulatory sequence(s).

In another embodiment, this recombinant nucleic acid molecule may optionally further comprise an operably linked terminator which is preferably functional in plant cells. The recombinant nucleic acid molecule of the invention may optionally further comprise additional control, promoting and regulatory elements and/or selectable markers. It should be noted that these regulatory elements are operably linked to the recombinant molecule.

Regulatory elements that may be used in the expression constructs include promoters which may be either heterologous or homologous to the plant cell. The promoter may be a plant promoter or a non-plant promoter which is capable of driving high levels transcription of a linked sequence in plant cells and plants. Non-limiting examples of plant promoters that may be used effectively in practicing the invention include cauliflower mosaic virus (CaMV) $^{35}$S, rbcS, the promoter for the chlorophyll a/b binding protein, AdhI, NOS and HMG2, or modifications or derivatives thereof. The promoter may be either constitutive or inducible. For example, and not by way of limitation, an inducible promoter can be a promoter that promotes expression or increased expression of the lysosomal enzyme nucleotide sequence after mechanical gene activation (MGA) of the plant, plant tissue or plant cell.

The expression vectors used for transfecting or transforming the host cells of the invention can be additionally modified according to methods known to those skilled in the art to enhance or optimize heterologous gene expression in plants and plant cells. Such modifications include but are not limited to mutating DNA regulatory elements to increase promoter strength or to alter the protein of interest.

In a preferred embodiment, the high mannose protein of interest produced by the host cell of the invention may be a high mannose glycoprotein having at least one exposed mannose residue (at least one terminal mannose residue).

Such high mannose protein may be according to another preferred embodiment, a lysosomal enzyme selected from the group consisting of glucocerebrosidase (GCD), acid sphingomyelinase, hexosaminidase, α-N-acetylgalactosaminidise, acid lipase, α-galactosidase, glucocerebrosidase, α-L-iduronidase, iduronate sulfatase, α-mannosidase and sialidase The term "lysosomal enzyme", as used herein with respect to any such enzyme and product produced in a plant expression system described by the invention, refers to a recombinant peptide expressed in a transgenic plant cell from a nucleotide sequence encoding a human or animal lysosomal enzyme, a modified human or animal lysosomal enzyme, or a fragment, derivative or modification of such enzyme. Useful modified human or animal lysosomal enzymes include but are not limited to human or animal lysosomal enzymes having one or several naturally occurring or artificially introduced amino acid additions, deletions and/or substitutions.

Soluble lysosomal enzymes share initial steps of biosynthesis with secretory proteins, i.e., synthesis on the ribosome, binding of the N-terminal signal peptide to the surface of the rough endoplasmic reticulum (ER), transport into the lumen of the ER where the signal peptide is cleaved, and addition of oligosaccharides to specific asparagine residues (N-linked), followed by further modifications of the nascent protein in the Golgi apparatus [von Figura and Hasilik, Annu. Rev. Biochem. 55:167-193 (1986)]. The N-linked oligosaccharides can be complex, diverse and heterogeneous, and may contain high-mannose residues. The proteins undergo further processing in a post-ER, pre-Golgi compartment and in the cis-Golgi to form either an N-linked mannose 6-phosphate (M-6-P) oligosaccharide-dependent or N-linked M-6-P oligosaccharide-independent recognition signal for lysosomal localized enzymes [Kornfeld & Mellman, Ann. Rev. Cell Biol., 5:483-525 (1989); Kaplan et al., Proc. Natl. Acad. Sci. USA 74:2026 (1977)]. The presence of the M-6-P recognition signal results in the binding of the enzyme to M-6-P receptors (MPR). These bound enzymes remain in the cell, are eventually packaged into lysosomes, and are thus segregated from proteins targeted for secretion or to the plasma membrane.

In a preferred embodiment, the lysosomal enzyme may be the human glucocerebrosidase (GCD).

Still further, in a particular embodiment, this preferred host cell is transformed or transfected by a recombinant nucleic acid molecule which further comprises an $^{35}$S promoter from Cauliflower Mosaic Virus, preferably, having the nucleic acid sequence as denoted by SEQ ID NO: 9, an octopine synthase terminator of *Agrobacterium tumefaciens*, preferably, having the nucleic acid sequence as denoted by SEQ ID NO: 12 and TMV (Tobacco Mosaic Virus) omega translational enhancer element. According to a preferred embodiment, this recombinant nucleic acid molecule comprises the nucleic acid sequence substantially as denoted by SEQ ID NO: 13 and encodes a high mannose GCD having the amino acid sequence substantially as denoted by SEQ ID NOs: 14 or 15.

It should be appreciated that the present invention further provides for an expression vector comprising a nucleic acid molecule encoding a biologically active high mannose lysosomal enzyme.

In one preferred embodiment of the aspect, the expression vector of the invention comprises a nucleic acid molecule encoding a biologically active high mannose human glucocerebrosidase (GCD). Preferably, this preferred expression vector comprises a recombinant nucleic acid molecule which having the nucleic acid sequence substantially as denoted by SEQ ID NO: 13. According to a specific embodiment, a preferred expression vector utilizes the pGREEN II plasmid as described by the following Example 1.

It should be further noted, that the invention provides for an expression cassette comprised within the expression vector described above.

In a second aspect, the present invention relates to a recombinant high mannose protein produced by the host cell of the invention.

In a preferred embodiment, this high mannose protein may be a biologically active high mannose lysosomal enzyme selected from the group consisting of glucocerebrosidase (GCD), acid sphingomyelinase, hexosaminidase, α-N-acetylgalactosaminidise, acid lipase, α-galactosidase, glucocerebrosidase, α-L-iduronidase, iduronate sulfatase, α-mannosidase and sialidase. Most preferably, this lysosomal enzyme may be human glucocerebrosidase (GCD).

The term "biologically active" is used herein with respect to any recombinant lysosomal enzyme produced in a plant expression system to mean that the recombinant lysosomal enzyme is able to hydrolyze either the natural substrate, or an analogue or synthetic substrate of the corresponding human or animal lysosomal enzyme, at detectable levels.

Still further, the invention provides for a recombinant biologically active high mannose lysosomal enzyme having at least one oligosaccharide chain comprising an exposed mannose residue.

According to a preferred embodiment, the recombinant lysosomal enzyme of the invention can bind to a mannose receptor on a target cell in a target site. Preferably, this site may be within a subject suffering from a lysosomal storage disease.

Optionally and more preferably, the recombinant lysosomal enzyme has increased affinity for the target cell, in comparison with the corresponding affinity of a naturally occurring lysosomal enzyme for the target cell. In a specific embodiment, the target cell at the target site may be a Kupffer cell in the liver of the subject.

In a preferred embodiment, the recombinant lysosomal enzyme may be selected from the group consisting of glucocerebrosidase (GCD), acid sphingomyelinase, hexosaminidase, α-N-acetylgalactosaminidise, acid lipase, α-galactosidase, glucocerebrosidase, α-L-iduronidase, iduronate sulfatase, α-mannosidase or sialidase.

Most preferably, this recombinant lysosomal enzyme is glucocerebrosidase (GCD).

In a third aspect, the invention relates to a method of producing a high mannose protein. Accordingly, the method of the invention comprises the steps of: (a) preparing a culture of recombinant host cells transformed or transfected with a recombinant nucleic acid molecules encoding for a recombinant protein of interest or with an expression vector comprising the recombinant nucleic acid molecules; (b) culturing the host cell culture prepared by step (a) in suspension under conditions permitting the expression of the high mannose protein, wherein the host cells produce the protein in a highly mannosylated form; (c) harvesting the cells from the culture provided in (a) and recovering the protein from the cells; and (d) purifying the protein of step (c) by a suitable protein purification method.

Optionally and preferably, the recombinant protein may be produced by plant cells according to the present invention by culturing in a device described with regard to U.S. Pat. No. 6,391,638, issued on May 21, 2002 and hereby incorporated by reference as if fully set forth herein. Conditions for culturing plant cells in suspension with this device are described with regard to the US patent application entitled "CELL/TISSUE CULTURING DEVICE, SYSTEM AND METHOD" by one of the present inventors and owned in common with the present application, which is hereby incorporated by reference as if fully set forth herein and which was filed on the same day as the present application.

A particular and non limiting example for recovering and purification of a high mannose protein of interest produced by the method of the invention may be found in the following Examples. The Examples show that a recombinant h-GCD produced by the invention was unexpectedly bound to internal membrane of the transformed carrot cells of the invention and not secreted to the medium. The soluble rh-GCD may be separated from cell debris and other insoluble component according to means known in the art such as filtration or precipitation. For Example, following a freeze-thaw cycle, the cells undergo breakage and release of intracellular soluble proteins, whereas the h-GCD remains bound to insoluble membrane debris. This soluble and insoluble membrane debris mixture was next centrifuged and the soluble fraction was removed thus simplifying the purification. The membrane bound h-GCD can then be dissolved by mechanical disruption in the presence of a mild detergent, protease inhibitors and neutralizing oxidation reagent. The soluble enzyme may be further purified using chromatography techniques, such as cation exchange and hydrophobic interaction chromatography columns. During rh-GCD production in the bioreactor and the purification process the h-GCD identity, yield, purity and enzyme activity can be determined by one or more biochemical assays. Including but not limited to detecting hydrolysis of the enzyme's substrate or a substrate analogue, SDS-polyacrylamide gel electrophoresis analysis and immunological analyses such as ELISA and Western blot.

According to a preferred embodiment, the host cell used by this method comprises the host cell of the invention.

In another preferred embodiment, the high mannose protein produced by the method of the invention may be a biologically active high mannose lysosomal enzyme having at least one oligosaccharide chain comprising an exposed mannose residue.

This recombinant enzyme can bind to a mannose receptor on a target cell in a target site. More particularly, the recombinant enzyme produced by the method of the invention has increased affinity for the target cell, in comparison with the corresponding affinity of a naturally occurring lysosomal enzyme to the target cell. Accordingly, the target cell at the target site may be Kupffer cell in the liver of the subject.

In a specific embodiment, this lysosomal enzyme may be selected from the group consisting of glucocerebrosidase (GCD), acid sphingomyelinase, hexosaminidase, α-N-acetylgalactosaminidise, acid lipase, α-galactosidase, glucocerebrosidase, α-L-iduronidase, iduronate sulfatase, α-mannosidase and sialidase. Most preferably, this lysosomal enzyme may be glucocerebrosidase (GCD).

In another preferred embodiment, the host cell used by the method of the invention may be a plant root cell selected from the group consisting of *Agrobacterium rihzogenes* transformed root cell, celery cell, ginger cell, horseradish cell and carrot cell.

Most preferably, the plant root cell is a carrot cell. It should be particularly noted that the transformed host carrot cells are grown in suspension.

In a further aspect, the present invention relates to a method for treating a subject, preferably a mammalian subject, having lysosomal storage disease by using exogenous recombinant lysosomal enzyme.

Disclosed and described, it is to be understood that this invention is not limited to the particular examples, process steps, and materials disclosed herein as such process steps and materials may vary somewhat. It is also to be understood that the terminology used herein is used for the purpose of describing particular embodiments only and not intended to be limiting since the scope of the present invention will be limited only by the appended claims and equivalents thereof.

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps.

It must be noted that, as used in this specification and the appended claims, the singular forms "a", "an" and "the" include plural referents unless the content clearly dictates otherwise.

The following examples are representative of techniques employed by the inventors in carrying out aspects of the present invention. It should be appreciated that while these techniques are exemplary of preferred embodiments for the practice of the invention, those of skill in the art, in light of the present disclosure, will recognize that numerous modifications can be made without departing from the spirit and intended scope of the invention.

EXAMPLES

Experimental Procedures

Plasmid Vectors

CE-T—Was constructed from plasmid CE obtained from Prof. Galili [U.S. Pat. No. 5,367,110 Nov. 22, (1994)].
Plasmid CE was digested with SalI.
The SalI cohesive end was made blunt-ended using the large fragment of DNA polymerase I. Then the plasmid was digested with PstI and ligated to a DNA fragment coding for the ER targeting signal from the basic endochitinase gene [*Arabidopsis thaliana*] ATGAAGAC-TAATCTTTTTCTCTTTCTCATCTTTTCA CTTCTCCTATCATTATCCTCGGCCGAATTC, and vacuolar targeting signal from Tobacco chitinase A: GATCTTTTAGTCGATACTATG digested with SmaI and PstI.

pGREENII—obtained from Dr. P. Mullineaux [Roger P. Hellens et al., (2000)
Plant Mol. Bio. 42:819-832]. Expression from the pGREEN II vector is controlled by the 35S promoter from Cauliflower Mosaic Virus, the TMV (Tobacco Mosaic Virus) omega translational enhancer element and the octopine synthase terminator sequence from *Agrobacterium tumefaciens*.

cDNA hGCD—obtained from ATCC (Accession No. 65696), GC-2.2 [GCS-2 kb; lambda-EZZ-gamma3 *Homo sapiens*] containing glucosidase beta acid [glucocerebrosidase]. Insert lengths (kb): 2.20; Tissue: fibroblast WI-38 cell.

Construction of Expression Plasmid

Figure 1B:
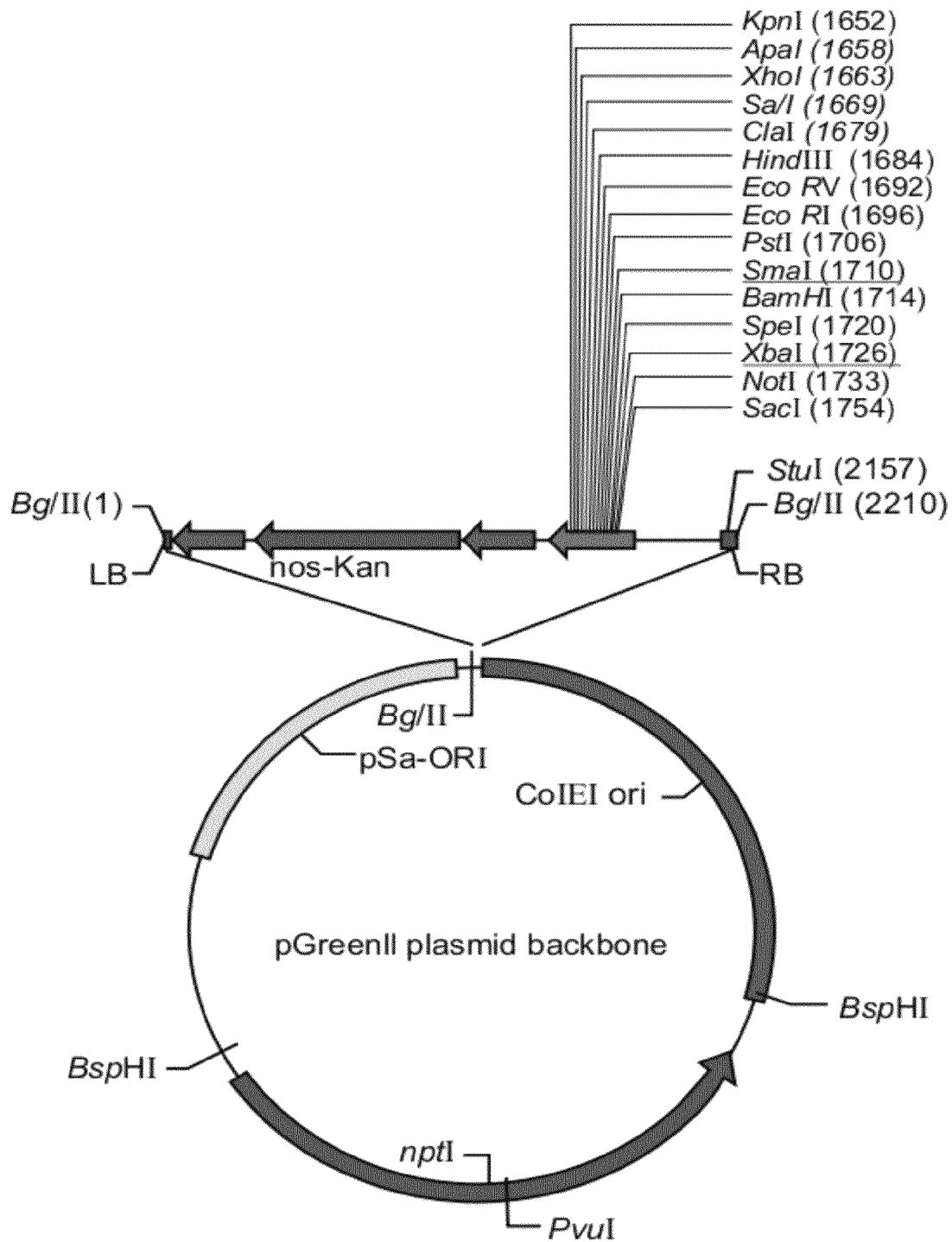

The cDNA coding for hGCD (ATTC clone number 65696) was amplified using the forward: 5' CA GAATTCGCCCGCCCCTGCA 3' and the reverse: 5' CTC AGATCTTGGCGATGCCACA 3' primers. The purified PCR DNA product was digested with endonucleases EcoRI and BglII (see recognition sequences underlined in the primers) and ligated into an intermediate vector having an expression cassette E-T digested with the same enzymes. The expression cassette was cut and eluted from the intermediate vector and ligated into the binary vector pGREENII using restriction enzymes SmaI and XbaI, forming the final expression vector. Kanamycine resistance is conferred by the NPTII gene driven by the nos promoter obtained together with the pGREEN vector (FIG. 1B). The resulting expression cassette is presented by FIG. 1A.

The resulting plasmid was sequenced to ensure correct in-frame fusion of the signals using the following sequencing primers: 5' 35S promoter: 5' CTCAGAAGACCAGAGGGC 3', and the 3' terminator: 5' CAAAGCGGCCATCGTGC 3'.

Establishment of Carrot Callus and Cell Suspension Cultures

Establishment of carrot callus and cell suspension cultures we preformed as described previously by Tones K. C. (Tissue culture techniques for horticular crops, p.p. 111, 169).

Transformation of Carrot Cells and Isolation of Transformed Cells.

Transformation of carrot cells was preformed using *Agrobacterium* transformation by an adaptation of a method described previously [Wurtele, E. S. and Bulka, K. Plant Sci. 61:253-262 (1989)]. Cells growing in liquid media were used throughout the process instead of calli. Incubation and growth times were adapted for transformation of cells in liquid culture. Briefly, *Agrobacteria* were transformed with the pGREEN II vector by electroporation [den Dulk-Ra, A. and Hooykaas, P. J. (1995) Methods Mol. Biol. 55:63-72] and then selected using 30 mg/ml paromomycine antibiotic. Carrot cells were transformed with *Agrobacteria* and selected using 60 mg/ml of paromomycine antibiotics in liquid media.

Screening of Transformed Carrot Cells for Isolation of Calli Expressing High Levels of GCD 14 days following transformation, cells from culture were plated on solid media at dilution of 3% packed cell volume for the formation of calli from individual clusters of cells. When individual calli reached 1-2 cm in diameter, the cells were homogenized in SDS sample buffer and the resulting protein extracts were separated on SDS-PAGE [Laemmli U., (1970) Nature 227:680-685] and transferred to nitrocellulose membrane (hybond C nitrocellulose, 0.45 micron. Catalog No: RPN203C From Amersham Life Science). Western blot for detection of GCD was performed using polyclonal anti hGCD antibodies (described herein below). Calli expressing significant levels of GCD were expanded and transferred to growth in liquid media for scale up, protein purification and analysis.

Preparation of Polyclonal Antibodies 75 micrograms recombinant GCD (Cerezyme™) were suspended in 3 ml complete Freund's adjuvant and injected to each of two rabbits. Each rabbit was given a booster injection after two weeks. The rabbits were bled about 10 days after the booster injection and again at one week intervals until the antibody titer began to drop. After removal of the clot the serum was divided into aliquots and stored at $-20°$ C.

Upscale Culture Growth in a Bioreactor

An about 1cm (in diameter) callus of genetically modified carrot cells containing the rh-GCD gene was plated onto Murashige and Skoog (MS) 9 cm diameter agar medium plate containing 4.4 gr/l MSD medium (Duchefa), 9.9 mg/l thiamin HCl (Duchefa), 0.5 mg folic acid (Sigma) 0.5 mg/l biotin (Duchefa), 0.8 g/l Casein hydrolisate (Ducifa), sugar 30 g/l and hormones 2-4 D (Sigma). The callus was grown for 14 days at $25°$ C.

Suspension cell culture was prepared by sub-culturing the transformed callus in a MSD liquid medium (Murashige & Skoog (1962) containing 0.2 mg/l 2,4-dichloroacetic acid), as is well known in the art. The suspension cells were cultivated in 250 ml Erlenmeyer flask (working volume starts with 25 ml and after 7 days increases to 50 ml) at $25°$ C. with shaking speed of 60 rpm. Subsequently, cell culture volume was increased to 1 L Erlenmeyer by addition of working volume up to 300 ml under the same conditions. Inoculum of the small bio-reactor (10 L) [see WO98/13469] containing 4 L MSD medium, was obtained by addition of 400 ml suspension cells derived from two 1 L Erlenmeyer that were cultivated for seven days. After week of cultivation at $25°$ C. with 1 Lpm airflow, MDS medium was added up to 10 L and the cultivation continued under the same conditions. After additional five days of cultivation, most of the cells were harvested and collected by passing the cell media through 80μ net. The extra medium was squeezed out and the packed cell cake was store at $-70°$ C.

Further details of the bioreactor device may be found with regard to U.S. Pat. No. 6,391,638, issued on May 21, 2002 and previously incorporated by reference.

Protein Purification

In order to separate the medium from the insoluble GCD, frozen cell cake containing about 100 g wet weight cells was thawed, followed by centrifugation of the thawed cells at 17000×g for 20 min at $4°$ C. The insoluble materials and intact cells were washed by re-suspension in 100 ml washing buffer (20 mM sodium phosphate pH 7.2, mM EDTA), and then precipitated by centrifugation at 17000 g for 20 min at $4°$ C. The rh-GCD (recombinant human GCD) was extracted and solubilized by homogenization of the pellet in 200 ml extraction buffer (20 mM sodium phosphate pH 7.2, 20 mM EDTA, 1 mM PMSF, 20 mM ascorbic acid, 3.8 g polyvinylpolypyrrolidone (PVPP), 1 mM DTT and 1% Triton-x-100). The homogenate was then shaken for 30 min at room temperature and clarified by centrifugation at 17000×g for 20 min at $4°$ C. The pellet was discarded and the pH of the supernatant was adjusted to pH 5.5 by addition of concentrated citric acid. Turbidity generated after pH adjustment was clarified by centrifugation under the same conditions described above.

Further purification was performed by chromatography columns procedure as follows: 200 ml of clarified medium were loaded on 20 ml strong cation exchange resin (Macro-Prep high-S support, Bio-Rad) equilibrated in 25 mM sodium citrate buffer pH 5.5, packed in a XK column (2.6×20 cm). The column was integrated with an AKTA (prime system (Amersham Pharmacia Biotech) that allowed to monitor the conductivity, pH and absorbency at 280 nm. The sample was loaded at 20 ml/min, afterwards the column was washed with equilibration buffer (25 mM sodium citrate buffer pH 5.5) at flow rate of 12 ml/min until UV absorbency reached the base line. Pre-elution of the rh-GCD was performed with equilibration buffer containing 200 mM NaCl and the elution was obtained with equilibration buffer containing 600 mM NaCl. Fractions collected during the run were monitored by enzyme activity assay, and tubes exhibiting enzymatic activity (in the elution peak) were pooled. Pooled samples were diluted (1:5) in water containing 5% ethanol and pH adjusted to 6.0 with NaOH. Sample containing the rh-GCD was applied on the second XK column (1.6×20 cm) packed with 10 ml of the same resin as in the previous column. The resin in this column was equilibrate with 20 mM citrate buffer pH 6.0 containing 5% ethanol. Following the sample load the column was washed with the equilibration buffer and the GCD was eluted from the column by elution buffer (20 mM citrate buffer pH 6.0, 5% ethanol and 1M NaCl). The fractions of the absorbent peak in the elution step were pooled and applied on a third column.

The final purification step was performed on a XK column (1.6×20 cm) packed with 8 ml hydrophobic interaction resin (TSK gel, Toyopearl Phenyl-650C, Tosoh Corp.). The resin was equilibrated in 10 mM citrate buffer pH 6.0 containing 5% ethanol. The GCD elution pool from the previous column was loaded at 6 ml/min followed by washing with equilibration buffer until the UV absorbent reach the baseline. The pure GCD was eluted by 10 mM citric buffer containing 50% ethanol, pooled and stored at $-20°$ C.

Determination of Protein Concentration

Protein concentrations in cell extracts and fractions were assayed by the method of Lowry/Bradford (Bio Rad protein assay) [Bradford, M., Anal. Biochem. (1976) 72:248] using a bovine serum albumin standard (fraction V Sigma). Alternatively, concentration of homogenous protein samples was determined by absorption at 280 nm, 1 mg/ml=1.4 $O.D._{280}$. Purity was determined by 280/260 nm ratio.

GCD Enzyme Activity Assay

Enzymatic activity of GCD was determined using p-nitrophenyl-β-D-glucopyranoside (Sigma) as a substrate. Assay buffer contained 60 mM phosphate-citrate buffer pH=6, 4 mM β-mercaptoethanol, 1.3 mM EDTA, 0.15% Triton X-100, 0.125% sodium taurocholate. Assay was preformed in 96 well ELISA plates, 0-50 microliter of sample were incubated with 250 microliter assay buffer and substrate was added to final concentration of 4 mM. The reaction was incubated at 37° C. for 60 min. Product (p-nitrophenyl; pNP) formation was detected by absorbance at 405 nm. Absorbance at 405 nm was monitored at t=0 and at the end point. After 60 min, 6 microliter of 5N NaOH were added to each well and absorbance at 405 nm was monitored again. Reference standard curve assayed in parallel, was used to quantitate concentrations of GCD in the tested samples [Friedman et al., (1999) Blood, 93(9):2807-16].

Kinetic Studies:

For kinetic studies, GCD activity was assayed as described by hereinabove with some modifications, using a fluorescent short-acyl-chain analogue of glucosylceramide, N-[6-[(7-nitrobenzo-2-oxa-1,3-diazol-4-yl)amino] hexanoyl]-D erythro-glucosylsphingosine (C6-NBD-D-erythro-GlcCer). C6-NBD-GlcCer was synthesized by N-acylation of glucosylsphingosine using succinimidyl 6-7-nitrobenzo-2-oxa-1,3-diazol-4-yl) aminohexanoate as described by Schwarzmann and Sandhoff (1987). The assay was performed using 0.2 μg of either Cerezyme® or plant GCD of the invention in a final volume of 200 μl MES buffer (50 mM, pH 5.5). Concentrations of C6-NBD-GlcCer ranged from 0.25 to 100 μM. Reactions were allowed to proceed for 5 min at 37° C., and were stopped by addition of 1.5 ml of chloroform/methanol (1:2, v/v) prior to extraction and analysis of the fluorescent lipids.

Biochemical Analyses:

In Gel Proteolysis and Mass Spectrometry Analysis

The stained protein bands in the gel were cut with a clean razor blade and the proteins in the gel were reduced with 10 mM DTT and modified with 100 mM iodoacetamide in 10 mM ammonium bicarbonate. The gel pieces were treated with 50% acetonitrile in 10 mM ammonium bicarbonate to remove the stain from the proteins following by drying the gel pieces. The dried gel pieces were rehydrated with 10% acetonitrile in 10 mM ammonium bicarbonate containing about 0.1 μg trypsin per sample. The gel pieces were incubated overnight at 37° C. and the resulting peptides were recovered with 60% acetonitrile with 0.1% trifluoroacetate.

The tryptic peptides were resolved by reverse-phase chromatography on 0.1×300-mm fused silica capillaries (J&W, 100 micrometer ID) home-filled with porous R2 (Persepective). The peptides were eluted using a 80-min linear gradient of 5 to 95% acetonitrile with 0.1% acetic acid in water at flow rate of about 1 μl/min. The liquid from the column was electrosprayed into an ion-trap mass spectrometer (LCQ, Finnegan, San Jose, Calif.). Mass spectrometry was performed in the positive ion mode using repetitively full MS scan followed by collision induces dissociation (CID) of the most dominant ion selected from the first MS scan. The mass spectrometry data was compared to simulated proteolysis and CID of the proteins in the NR—NCBI database using the Sequest software [J. Eng and J. Yates, University of Washington and Finnegan, San Jose].

The amino terminal of the protein was sequenced on Peptide Sequencer 494A (Perkin Elmer) according to manufacture instructions.

GCD Uptake of Peritoneal Macrophages

Targeting and uptake of GCD to macrophages is known to be mediated by the Mannose/N-acetylglucosmine receptor and can be determined using thioglycolate-elicited peritoneal macrophages obtained from mice, as described by Stahl P. and Gordon S. [J. Cell Biol. (1982) 93(1):49-56]. Briefly, mice (female, strain C57-B6) were injected intraperitoneally with 2.5 ml of 2.4% Bacto-thioglycolate medium w/o dextrose (Difco Cat. No. 0363-17-2). After 4-5 days, treated mice were sacrificed by cervical dislocation and the peritoneal cavity rinsed with phosphate buffered saline. Cells were pelleted by centrifugation (1000×g 10 min) and were resuspended in DMEM (Beit Haemek, Israel) containing 10% fetal calf serum. Cells were then plated at $1-2×10^5$ cell/well in 96-well tissue culture plates and incubated at 37° C. After 90 minutes, non-adherent cells were washed out three times using PBS, and the adherent macrophages were incubated for 90 min at 37° C., in culture medium containing specified quantities of rhGCD, ranging from 0 to 40 micrograms in 200 microliter final volume, in the absence and presence of yeast mannan (2-10, 5 mg/ml). After incubation, medium containing excess rGCD was removed, and cells were washed three times with PBS and then lysed with lysis buffer (10 mM Tris pH=7.3, 1 mM $MgCl_2$, 0.5% NP-40 and protease inhibitors). The activity of rGCD taken up by the cells was determined by subjecting the cell lysates to in vitro glycosidase assay as described above.

Example 1

Construction of Expression Plasmid

This Example describes the construction of an exemplary expression plasmid, used with regard to the Examples below, in more detail.

The cDNA coding for hGCD (ATTC clone number 65696) was amplified using the forward: 5' CA<u>GAATTC</u>GCCCGCCCCTGCA 3' (also denoted by SEQ ID NO: 3) and the reverse: 5' CTC<u>AGATCT</u>TGGCGATGCCACA 3' (also denoted by SEQ ID NO: 4) primers.

The purified PCR DNA product was digested with endonucleases EcoRI and BglII (see recognition sequences underlined in the primers) and ligated into an intermediate vector having an expression cassette CE-T digested with the same enzymes. CE-T includes ER targeting signal MKTNLFLF-LIFSLLLSLSSAEF (also denoted by SEQ ID NO: 1) from the basic endochitinase gene [*Arabidopsis thaliana*], and vacuolar targeting signal from Tobacco chitinase A: DLLVDTM* (also denoted by SEQ ID NO: 2).

The expression cassette was cut and eluted from the intermediate vector and ligated into the binary vector pGREENII using restriction enzymes SmaI and XbaI, forming the final expression vector. Kanamycine resistance is conferred by the NPTII gene driven by the nos promoter together with the pGREEN vector (FIG. 1B). The resulting expression cassette is presented by FIG. 1A.

The resulting plasmid was sequenced to ensure correct in-frame fusion of the signals using the following sequencing primers:

Primer from the 5' 35S promoter: 5' CTCAGAAGACCA-GAGGGC 3' (also denoted by SEQ ID NO: 5), and the 3' terminator: 5' CAAAGCGGCCATCGTGC 3' (also denoted by SEQ ID NO: 6). The verified cloned hGCD coding sequence is denoted by SEQ ID NO: 7.

Example 2

Transformation OF CARROT CELLS AND SCREENING FOR Transformed Cells Expressing rhGCD This Example describes an exemplary method for transforming carrot cells according to the present invention, as used in the Examples below.

Figure 2:
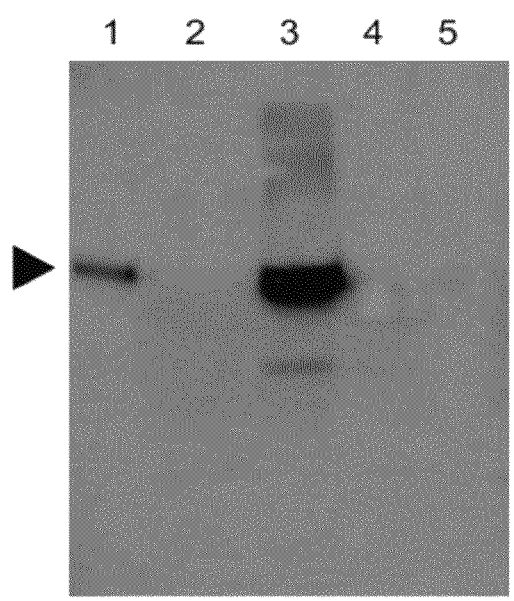
FIG. 2 shows Western blot analysis of hGCD transformed cell extracts using anti hGCD specific antibody. 1 gram of calli tissue was homogenized, and 15 micrograms of the soluble cell extract were analyzed on PAGE. Standard Cerezyme (lane 1) was used as a positive control, untransformed callus was used as negative control (lane 2), various selected calli extracts are shown in lanes 3-8.

Transformation of carrot cells was performed by *Agrobacterium* transformation as described previously by [Wurtele and Bulka (1989) ibid.]. Genetically modified carrot cells were plated onto Murashige and Skoog (MS) agar medium with antibiotics for selection of transformants. As shown by FIG. 2, extracts prepared from arising calli were tested for expression of GCD by Western blot analysis using anti hGCD antibody, and were compared to Cerezyme standard (positive control) and extracts of non-transformed cells (negative control). Of the various calli tested, one callus (number 22) was selected for scale-up growth and protein purification.

The Western blot was performed as follows.

For this assay, proteins from the obtained sample were separated in SDS polyacrylamide gel electrophoresis and transferred to nitrocellulose. For this purpose, SDS polyacrylamide gels were prepared as follows. The SDS gels consist of a stacking gel and a resolving gel (in accordance with Laemmli, UK 1970, Cleavage of structural proteins during assembly of the head of bacteriophage T4, Nature 227, 680-685). The composition of the resolving gels was as follows: 12% acrylamide (Bio-Rad), 4 microliters of TEMED (N,N,N',N'-tetramethylethylenediamine; Sigma catalog number T9281) per 10 ml of gel solution, 0.1% SDS, 375 mM Tris-HCl, pH 8.8 and ammonium persulfate (APS), 0.1%. TEMED and ammonium persulfate were used in this context as free radical starters for the polymerization. About 20 minutes after the initiation of polymerization, the stacking gel (3% acrylamide, 0.1% SDS, 126 mM Tris-HCl, pH 6.8, 0.1% APS and 5 microliters of TEMED per 5 ml of stacking gel solution) was poured above the resolving gel, and a 12 or 18 space comb was inserted to create the wells for samples.

The anode and cathode chambers were filled with identical buffer solution: Tris glycine buffer containing SDS (Biorad, catalog number 161-0772), pH 8.3. The antigen-containing material was treated with 0.5 volume of sample loading buffer (30 ml glycerol (Sigma catalog number G9012), 9% SDS, 15 ml mercaptoethanol (Sigma catalog number M6250), 187.5 mM Tris-HCl, pH 6.8, 500 microliters bromophenol blue, all volumes per 100 ml sample buffer), and the mixture was then heated at 100° C. for 5 minutes and loaded onto the stacking gel.

The electrophoresis was performed at room temperature for a suitable time period, for example 45-60 minutes using a constant current strength of 50-70 volts followed by 45-60 min at 180-200 Volt for gels of 13 by 9 cm in size. The antigens were then transferred to nitrocellulose (Schleicher and Schuell, Das sel).

Protein transfer was performed substantially as described herein. The gel was located, together with the adjacent nitrocellulose, between Whatmann 3 MM filter paper, conductive, 0.5 cm-thick foamed material and wire electrodes which conduct the current by way of platinum electrodes. The filter paper, the foamed material and the nitrocellulose were soaked thoroughly with transfer buffer (TG buffer from Biorad, catalog number 161-0771, diluted 10 times with methanol and water buffer (20% methanol)). The transfer was performed at 100 volts for 90 minutes at 4° C.

After the transfer, free binding sites on the nitrocellulose were saturated, at 4° C. over-night with blocking buffer containing 1% dry milk (Dairy America), and 0.1% Tween 20 (Sigma Cat P1379) diluted with phosphate buffer (Riedel deHaen, catalog number 30435). The blot strips were incubated with an antibody (dilution, 1:6500 in phosphate buffer containing 1% dry milk and 0.1% Tween 20 as above, pH 7.5) at 37° C. for 1 hour.

After incubation with the antibody, the blot was washed three times for in each case 10 minutes with PBS (phosphate buffered sodium phosphate buffer (Riedel deHaen, catalog number 30435)). The blot strips were then incubated, at room temperature for 1 h, with a suitable secondary antibody (Goat anti rabbit (whole molecule) HRP (Sigma cat #A-4914)), dilution 1:3000 in buffer containing 1% dry milk Dairy America), and 0.1% Tween 20 (Sigma Cat P1379) diluted with phosphate buffer (Riedel deHaen, catalog number 30435)). After having been washed several times with PBS, the blot strips were stained with ECL developer reagents (Amersham RPN 2209).

After immersing the blots in the ECL reagents the blots were exposed to X-ray film FUJI Super RX 18×24, and developed with FUJI-ANATOMIX developer and fixer (FUJI-X fix cat #FIXRTU 1 out of 2). The bands featuring proteins that were bound by the antibody became visible after this treatment.

Upscale Culture Growth in Bioreactors

Suspension cultures of callus 22 were obtained by sub-culturing of transformed callus in a liquid medium. Cells were cultivated in shaking Erlenmeyer flasks, until total volume was sufficient for inoculating the bioreactor (as described in Experimental procedures). The genetically modified transgenic carrot cells can be cultivated over months, and cell harvest can be obtained in cycling of 5 to 7 days (data not shown). At the seventh cultivation day, when the amount of rh-GCD production in carrot cell is at the peak, cells were harvested by passing of culture through 100 mesh nets. It should be noted that cells may be harvested by means known in the art such as filtration or centrifugation. The packed cell cake, which provides the material for purification of h-GCD to homogeneity, can be stored at freezing temperature.

Example 3

Purification of Recombinant Active hGCD Protein from Transformed Carrot Cells Recombinant h-GCD expressed in transformed carrot cells was found to be bound to internal membranes of the cells and not secreted to the medium. Mechanically cell disruption leaves the rGCD bound to insoluble membrane debris (data not shown). rGCD was then dissolved using mild detergents, and separated from cell debris and other insoluble components. The soluble enzyme was further purified using chromatography techniques, including cation exchange and hydrophobic interaction chromatography columns as described in Experimental procedures.

In order to separate the medium from the insoluble GCD, frozen cell cake containing about 100 g wet weight cells was thawed, followed by centrifugation at 17000×g for 20 min at 4° C. The insoluble materials and intact cells were washed by re-suspension in 100 ml washing buffer (20 mM sodium phosphate pH 7.2, 20 mM EDTA), and precipitated by centrifugation at 17000 g for 20 min at 4° C. The rGCD was extracted and solubilized by homogenization of the pellet in 200 ml extraction buffer (20 mM sodium phosphate pH 7.2, 20 mM EDTA, 1 mM PMSF, 20 mM ascorbic acid, 3.8 g polyvinylpolypyrrolidone (PVPP), 1 mM DTT, 1% Triton-x-100 (Sigma)). The homogenate was shaken for 30 min at room temperature and clarified by centrifugation at 17000 g for 20 min at 4° C. The pellet was discarded and the pH of the supernatant was adjusted to pH 5.5 by addition of concentrated citric acid. Turbidity generated after pH adjustment was clarified by centrifugation under the same conditions described above.

Further purification was performed by chromatography columns as follows: in a first stage, 200 ml of clarified extract were loaded on 20 ml strong cation exchange resin (Macro-Prep high-S support, Bio-Rad) equilibrated in 25 mM sodium citrate buffer pH 5.5, packed in a XK column (2.6×20 cm). The column was integrated with an AKTA prime system (Amersham Pharmacia Biotech) that allowed to monitor the conductivity, pH and absorbency at 280 nm. The sample was loaded at 20 ml/min, afterwards the column was washed with equilibration buffer (25 mM sodium citrate buffer pH 5.5) at flow rate of 12 ml/min until UV absorbency reached the base line. Pre-elution of the rh-GCD was performed with equilibration buffer containing 200 mM NaCl and the elution was obtained with equilibration buffer containing 600 mM NaCl. Fractions collected during the run were monitored by enzyme activity assay, and tubes exhibiting enzymatic activity (in the elution peak) were pooled. Pooled samples were diluted (1:5) in water containing 5% ethanol and pH adjusted to 6.0 with NaOH.

Figure 3A:
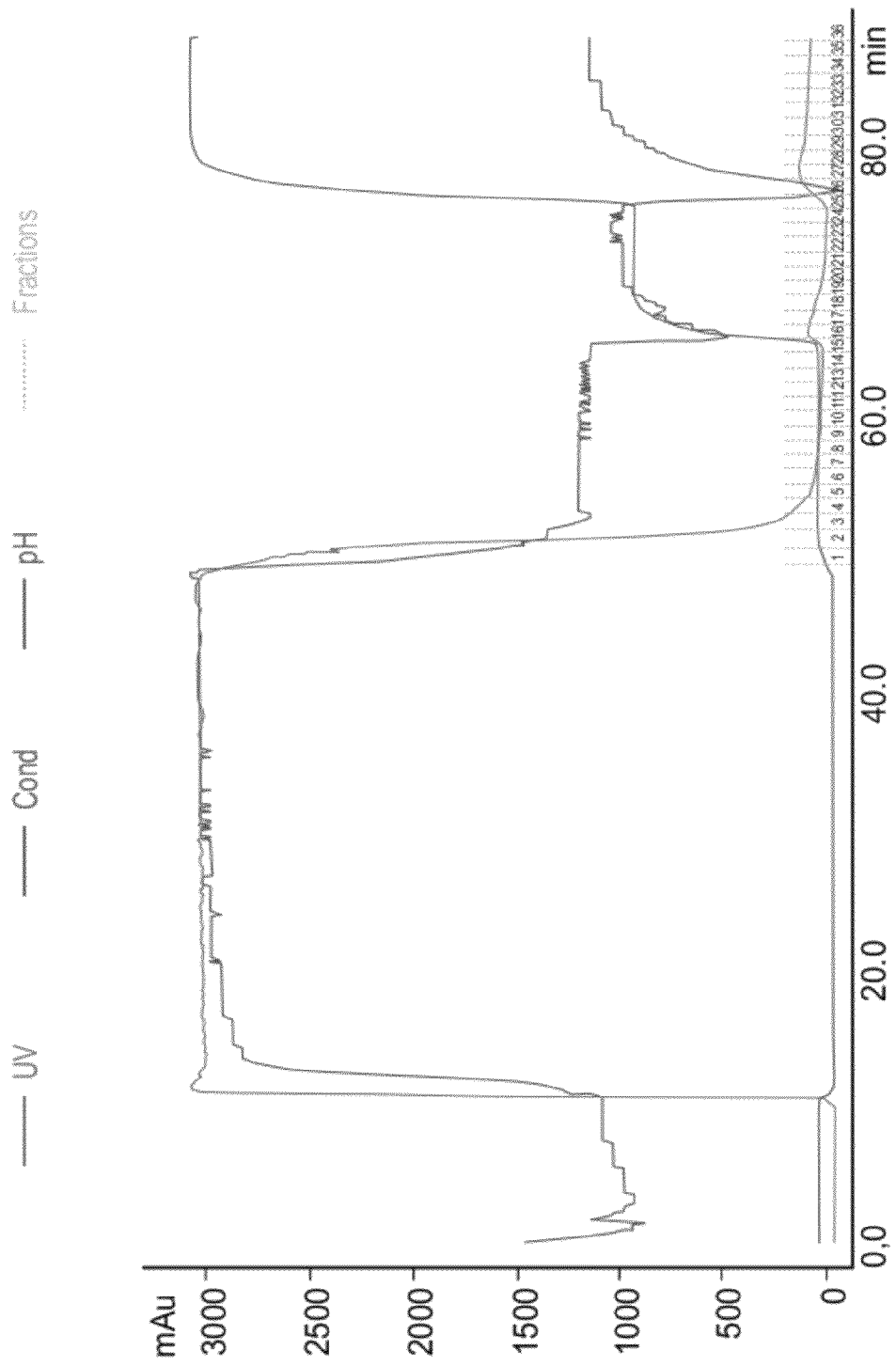
FIG. 3A-3C shows the first step of purification of rhGCD on a strong cation exchange resin (Macro-Prep high-S support, Bio-Rad), packed in a XK column (2.6×20 cm). The column was integrated with an AKTA prime system (Amersham Pharmacia Biotech) that allows conductivity monitoring, pH and absorbency at 280 nm. Elution of the rh-GCD was obtained with equilibration buffer containing 600 mM NaCl.
Figure 3B:
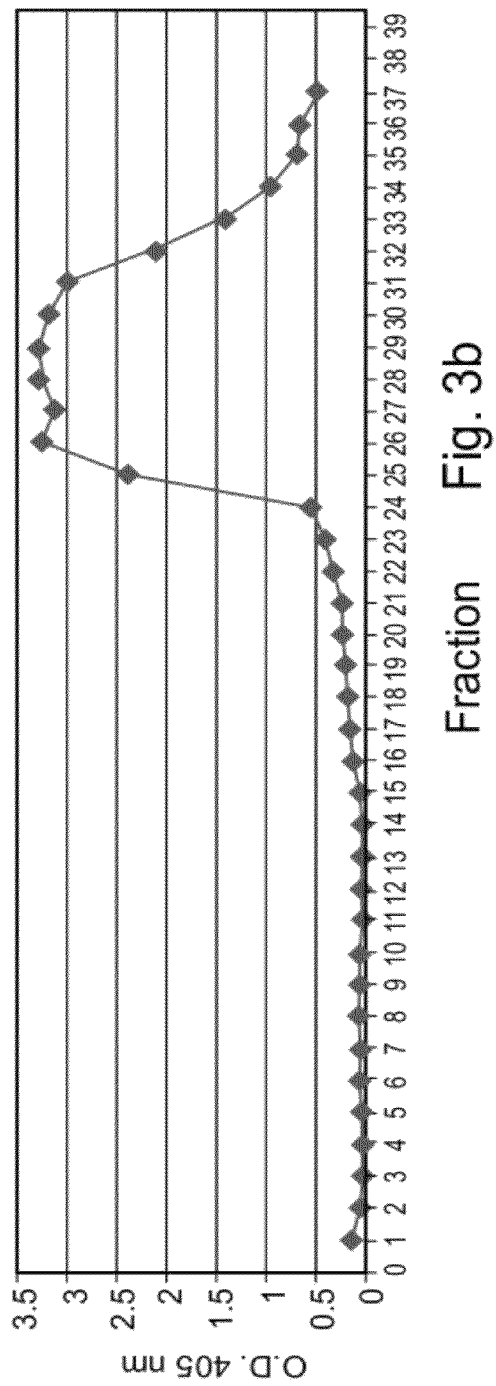
Figure 3C:
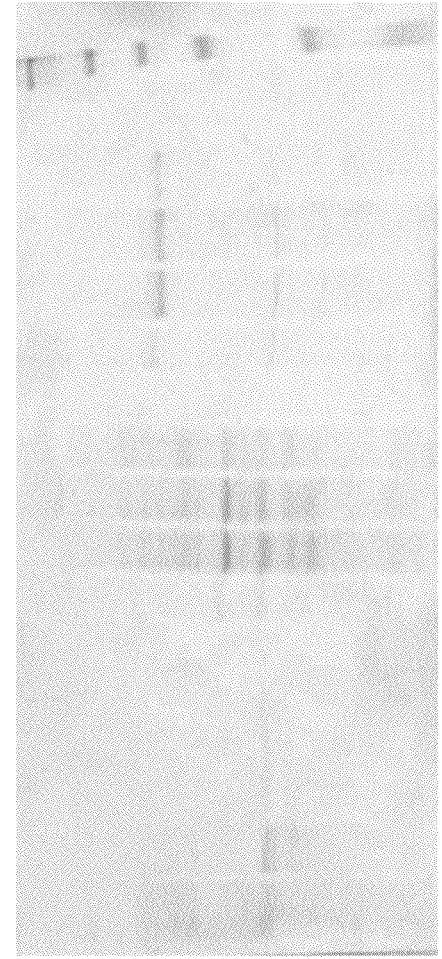

FIG. 3A represents a standard run of this purification stage. The fractions collected during the run were monitored by enzyme activity assay, as shown by FIG. 3B, and FIG. 3C shows coomassie-blue stain of elution fractions assayed for activity.

Figure 3D:
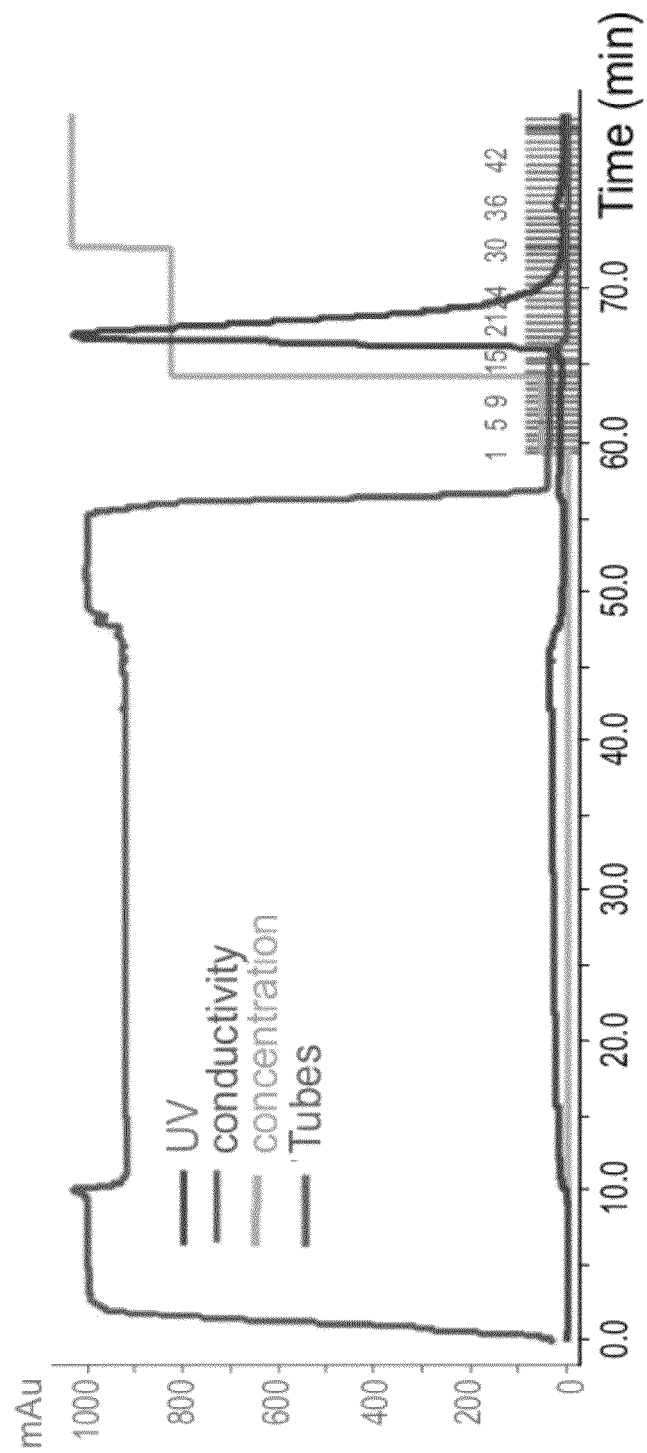
FIGS. 3D-3F show corresponding graphs as for FIGS. 3A-3C but for the second column.
Figure 3E:
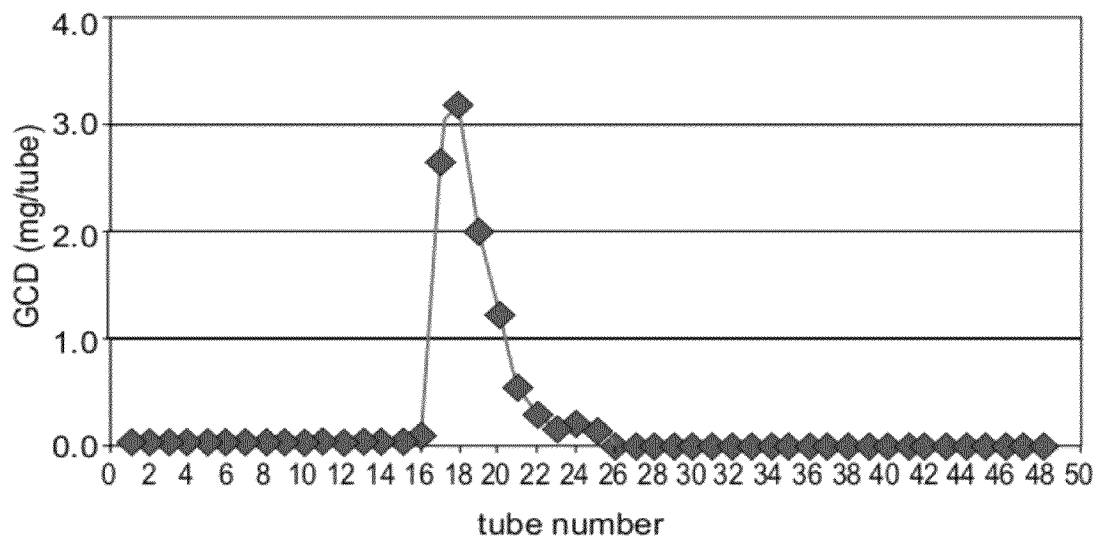
Figure 3F:
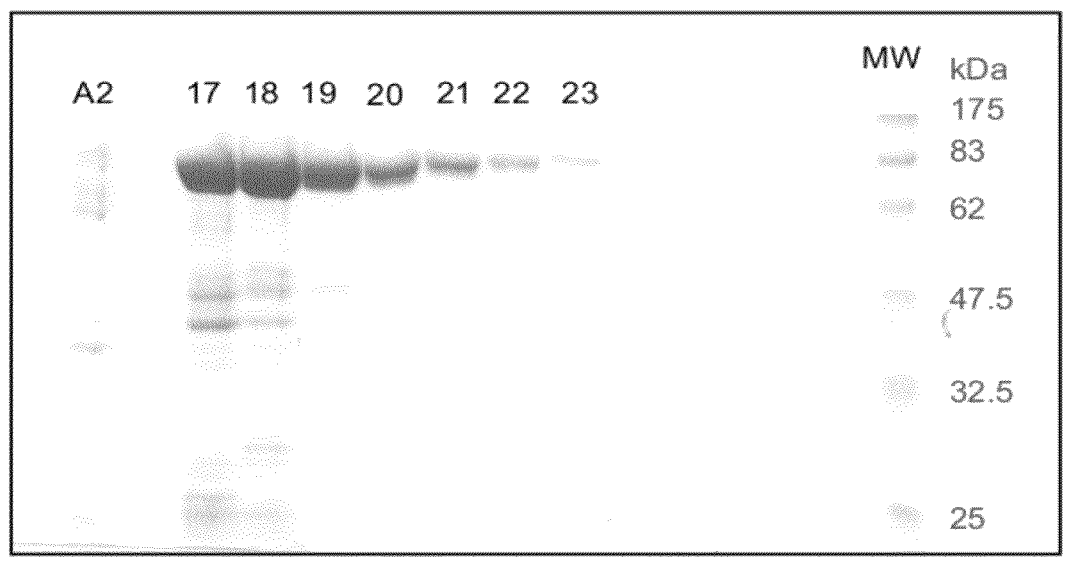

Elution fractions containing the rGCD was applied on a second XK column (1.6×20 cm) packed with 10 ml of the same resin as in the previous column, for a second purification stage. The resin in this column was equilibrated with 20 mM citrate buffer pH 6.0 containing 5% ethanol. Following the sample load the column was washed with the equilibration buffer and the rGCD was eluted from the column by elution buffer (20 mM citrate buffer pH 6.0, 5% ethanol and 1M NaCl). FIG. 3D represents a standard run of this purification stage. The fractions collected during the run were monitored by enzyme activity assay, as shown by FIG. 3E, and FIG. 3F shows a coomassie-blue stain of elution fractions assayed for activity.

The fractions of the absorbent peak in the elution step were pooled and applied on a third column, for a third purification stage. The third purification stage was performed on a XK column (1.6×20 cm) packed with 8 ml hydrophobic interaction resin (TSK gel, Toyopearl Phenyl-650C, Tosoh Corp.). The resin was equilibrated in 10 mM citrate buffer pH 6.0 containing 5% ethanol. The GCD elution pool from the previous column was loaded at 6 ml/min followed by washing with equilibration buffer until the UV absorbance reached the baseline. The pure GCD was eluted by 10 mM citric buffer containing 50% ethanol, pooled and stored at −20° C.

Figure 4A:
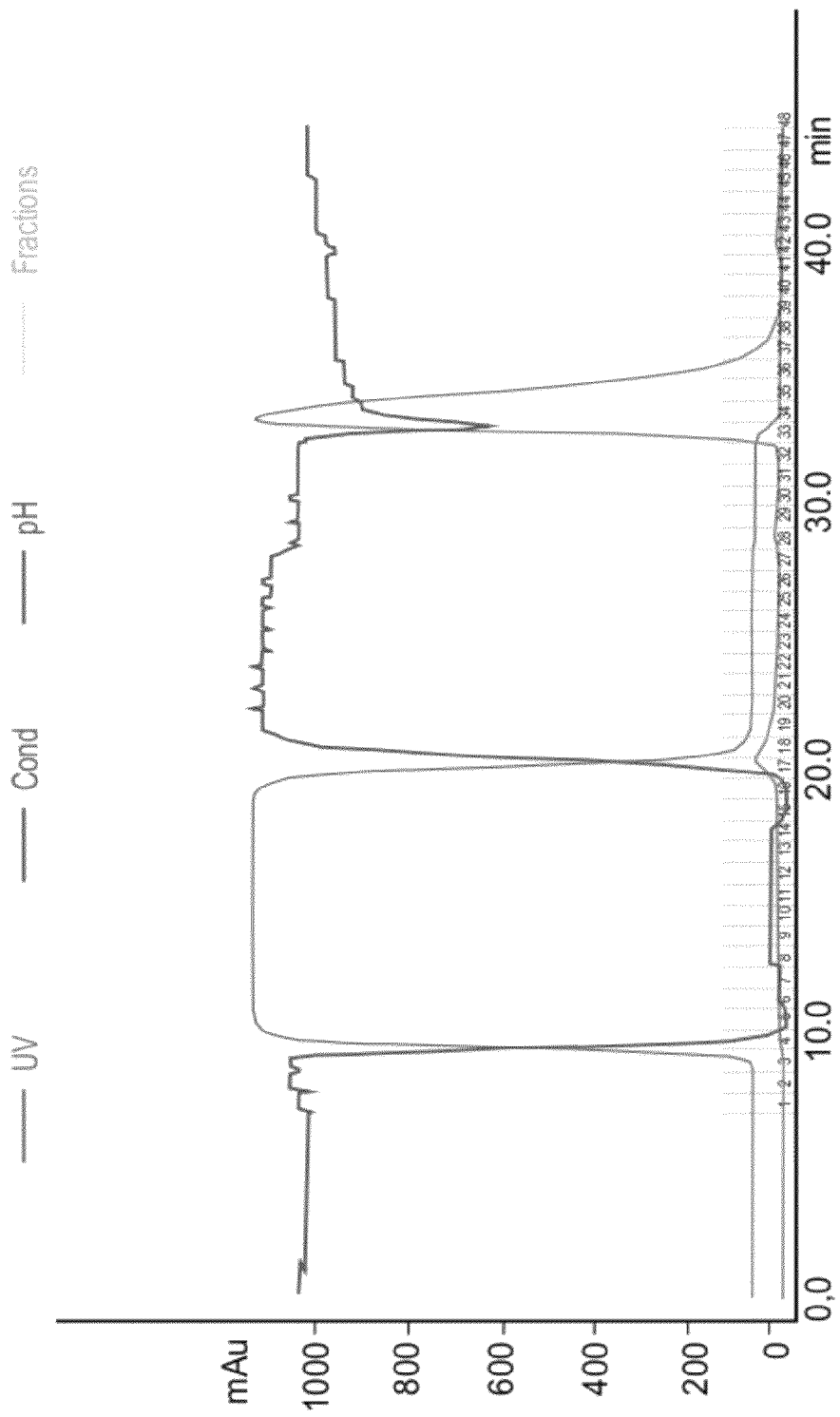
FIG. 4A-C: shows the final purification step of the recombinant hGCD on a hydrophobic interaction resin (TSK gel, Toyopearl Phenyl-650C, Tosoh Corp.), packed in a XK column (2.6×20 cm). The column was integrated with an AKTA prime system (Amersham Pharmacia Biotech) that allows conductivity monitoring, pH and absorbency at 280 nm. The GCD elution pool from the previous column was loaded at 6 ml/min followed by washing with equilibration buffer until the UV absorbance reach the baseline. The pure GCD was eluted by 10 mM citric buffer containing 50% ethanol.
Figure 4B:
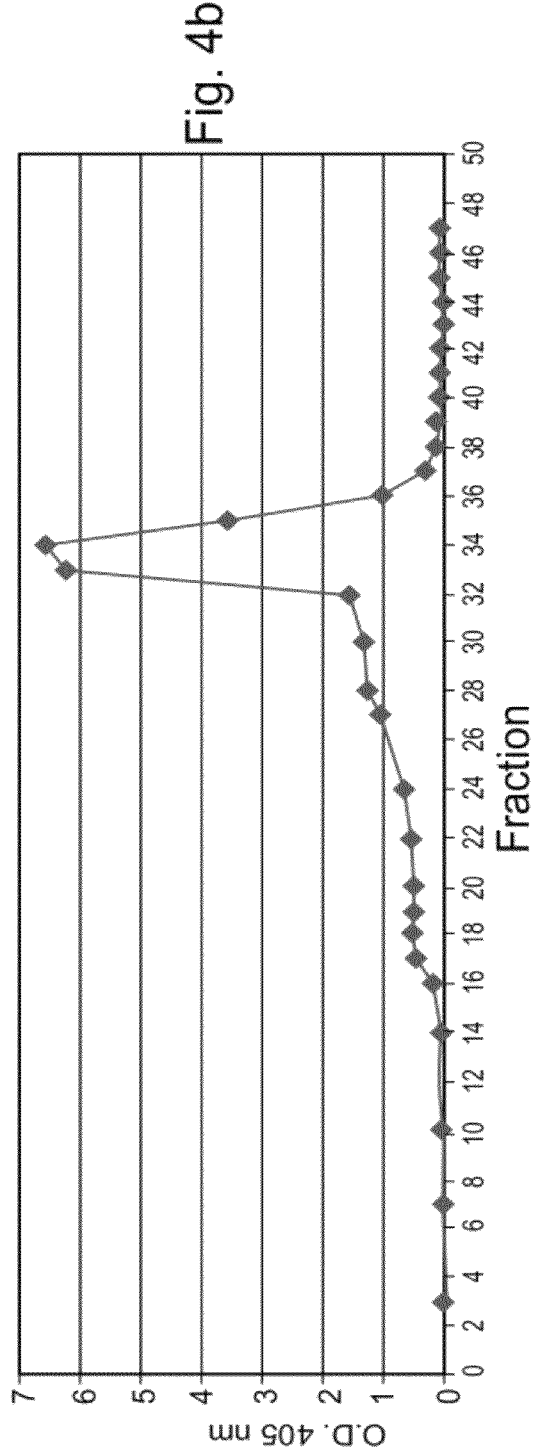
Figure 4C:
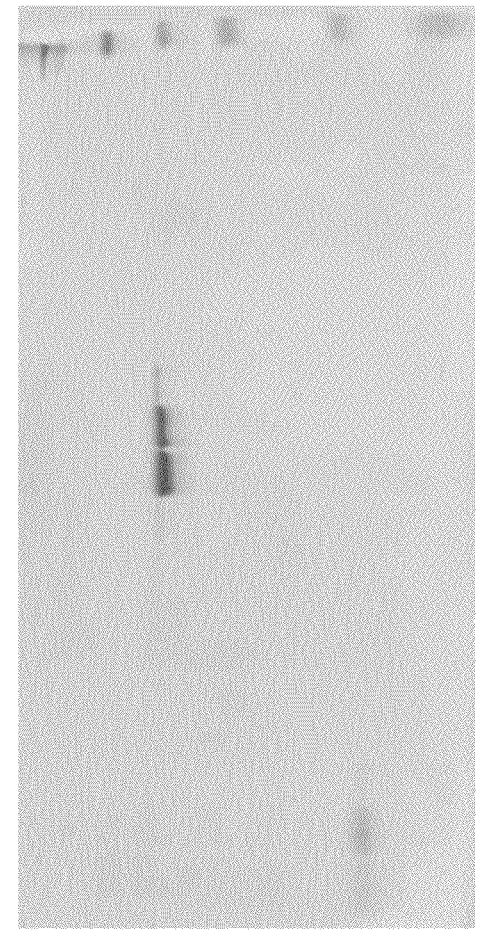

FIG. 4A represents a standard run of this purification stage. The fractions collected during the run were monitored by enzyme activity assay (FIG. 4B), and FIG. 4C shows coomassie-blue stain of elution fractions assayed for activity.

In a batch purification of cells that were processed, rGCD protein was purified to a level greater than 95%; if only the first and third stages are performed, purity is achieved at a level of about 80% (results not shown).

Biochemical Analysis

To validate the identity of purified rhGCD, Mass-Spec Mass-Spec (MSMS) analysis was preformed. Results obtained showed 49% coverage of protein sequence that matched the predicted amino acid sequence, based on the DNA of the expression cassette, including the leader peptide and targeting sequences.

Figure 9A:
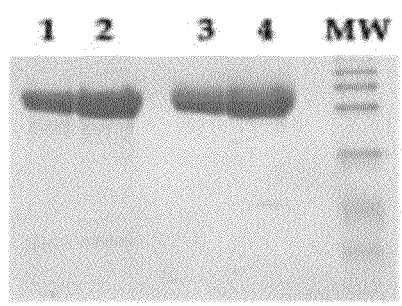
FIGS. 9a-9b show the antigenic and electrophoretic identity of purified recombinant human GCD of the present invention and a commercial human GCD (Cerezyme®) recombinantly produced in mammalian CHO cells.

Characterization and Sequencing of prGCD:

To further characterize the plant produced human recombinant GCD of the invention, the rhGCD was solubilized using Triton X-100, in the presence of an antioxidant, and purified to homogeneity by cation exchange and hydrophobic chromatography (FIG. 9a). Amino-acid sequencing of the plant produced human recombinant GCD of the invention demonstrated that the rhGCD sequence (SEQ ID NO: 15) corresponds to that of the human GCD (Swiss Prot P04062, protein ID AAA35873), and includes two additional amino acids (EF) at the N-terminus (designated −2 and −1 accordingly), derived from the linker used for fusion of the signal peptide, and an additional 7 amino acids at the C-terminus (designated 497-503) derived from the vacuolar targeting signal.

Figure 9B:
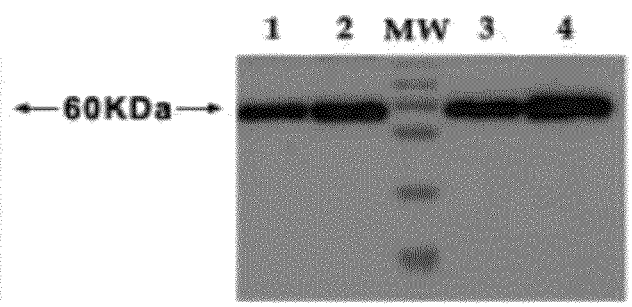

Immunodetection of the purified plant produced human recombinant GCD of the invention with anti-GCD polyclonal antibody was performed by Western blotting of the SDS-PAGE separated protein, along with Cerezyme® protein (FIG. 9b), confirming antigenic identity of the plant produced and CHO-produced proteins.

Figure 12:
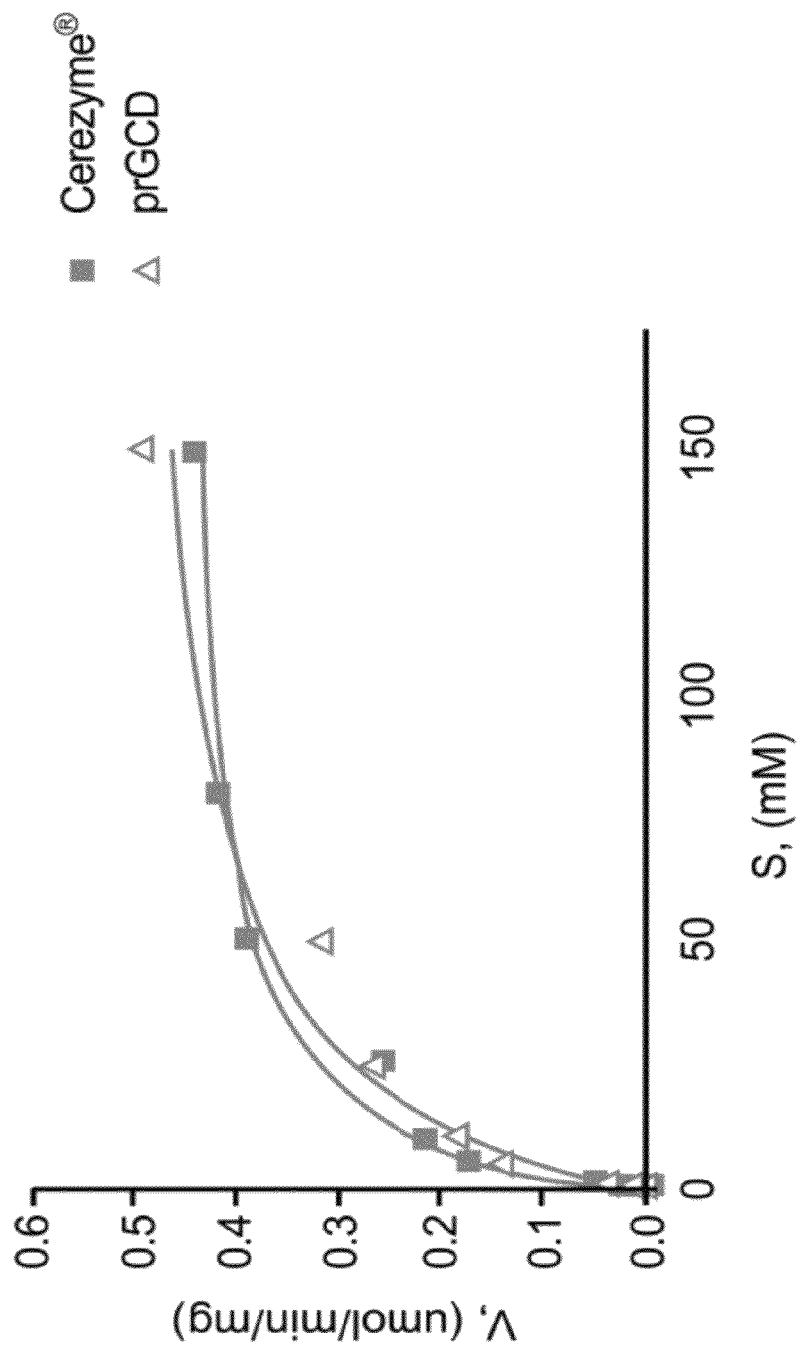
FIG. 12 is a kinetic analysis showing the identical catalytic kinetics characteristic of both recombinant human GCD of the invention (open triangles) and the mammalian-cell (CHO) prepared enzyme (Cerezyme®) (closed squares). Recombinant human GCD of the invention and Cerezyme® (0.2 µg) were assayed using C6-NBDGlcCer (5 min, 37° C.) in MES buffer (50 mM, pH 5.5). Michaelis-Menten kinetics was analyzed using GraphPad Prism software. Data are means of two independent experiments.

Enzymatic Activity of Recombinant Hgcd:

The activity of plant produced human recombinant GCD of the present invention was compared to that of Cerezyme®, using a fluorescent GlcCer analogue. FIG. 12 shows that similar specific activities were obtained, with $V_{max}$ values of 0.47±0.08 Kmol C6-NBD-ceramide formed/min/mg protein for prGCD and 0.43±0.06 for Cerezyme®, and similar Km values (20.7±0.7 KM for the GCD of the invention and 15.2±4.8 KM for Cerezyme®). Thus, these kinetic studies show that the activity of the plant produced human recombinant GCD of the present invention is similar to that of the CHO expressed enzyme.

Uptake and Activity of Recombinant Hgcd in Peritoneal Macrophages

Figure 5A:
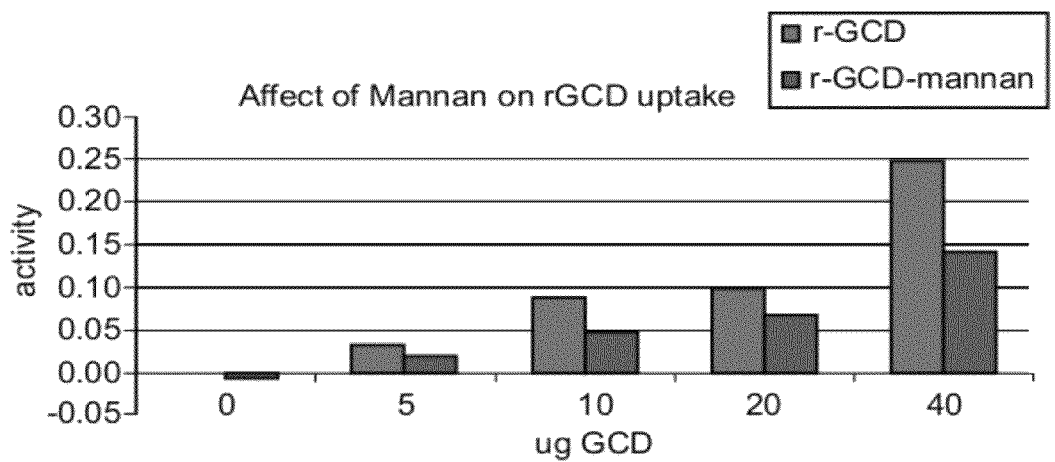

To determine whether the rhGCD produced in carrot has been correctly glycosylated and can undergo uptake by target cells, and thus be useful for treatment of Gaucher's disease, the ability of the rhGCD to bind to and be taken up by macrophages was next assayed. Targeting of rhGCD to macrophages is mediated by the Mannose/N-acetylglucosamine (Man/GlcNAc) receptor and can be determined using thioglycolate-elicited peritoneal macrophages. As shown by FIG. 5, rGCD undergoes uptake by cells at a high level. FIG. 5A shows uptake by cells of rGCD according to the present invention with regard to mannan concentration.

FIG. 5A shows uptake at comparable levels with Cerezyme™ (this preparation was prepared to 80% purity with only the first and third stages of the purification process described above).

Figure 5B:
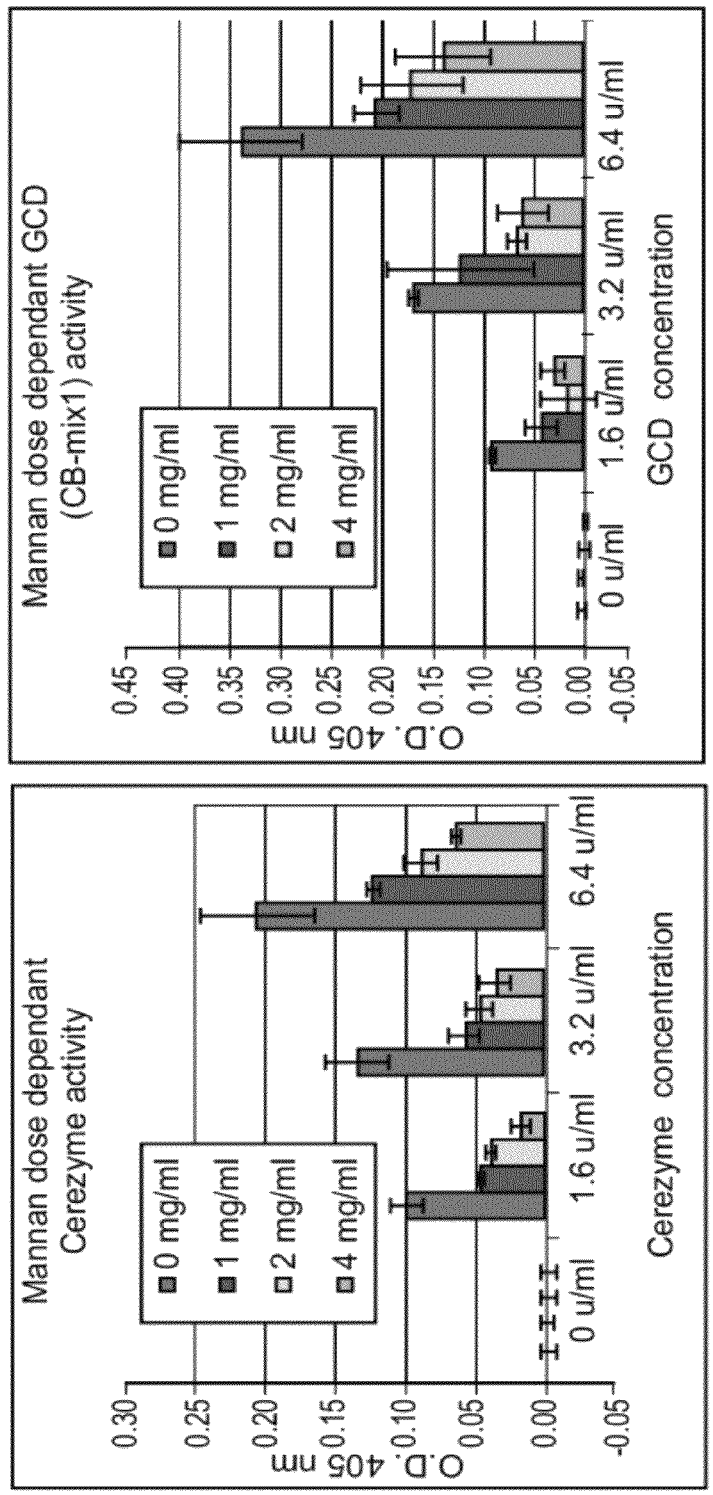

FIGS. 5B and 5C show that rGCD uptake is at a higher level than Cerezyme™ as this preparation was prepared to greater than 95% purity with all three stages of the purification process described above.

With regard to FIG. 5C, clearly the percent of specific activity from total activity, inhibited by 4 mg/ml mannan, is higher for the GCD of the present invention (rGCD or recombinant human GCD) than for the currently available product in the market as follows: GCD (CB-mix1, which is the rGCD of the present invention)—75% Cerezyme—65%. Furthermore, as shown by the figures, addition of mannan clearly inhibited binding of rGCD by the cells. At concentration of 2 mg/ml of mannan, the binding of rGCD was inhibited by 50%.

These results show that even without remodeling of glycan structures, rhGCD expressed and purified from transformed carrot cells can undergo uptake to target macrophage cells specifically through Man/GlcNAc receptors. Moreover, this recombinant rhGCD is enzymatically active.

FIG. 5D shows that the rhGCD is also recognized by an anti-GCD antibody in a Western blot; rGCD refers to the protein according to the present invention, while GCD standard (shown at 5, 10 and 25 ng per lane) is commercially purchased GCD (Cerezyme®).

Example 4

Toxicology Testing

The material obtained according to the above purification procedure was tested according to standard toxicology testing protocols (Guidance for Industry on Single Dose Acute Toxicity Testing for Pharmaceuticals, Center for Drug Evaluation and Research (CDER) PT 1 (61 FR 43934, Aug. 26, 1996) and by ICH M3(M) Non-clinical Safety Studies for the Conduct of Human Clinical Trials for Pharmaceuticals CPMP/ICH/286/95 modification, Nov. 16, 2000).

Mice were injected as follows: An initial dose of 1.8 mg/kg (clinical dose) was followed by doses of 9 and 18 mg/kg. Testing groups included six mice (ICR CD-1; 3 males and 3 females) for receiving rGCD (in a liquid carrier featuring 25 mM citrate buffer, 150 mM NaCl, 0.01% Tween 80, 5% ethanol) according to the present invention, and another six mice for being treated with the carrier alone as a control group. The mice were then observed for 14 days and were euthanized.

In another study, vehicle solution alone, or doses of prGCD in multiples of 1, 5, or 10 times the standard clinical dose (60 units/kg) were given to ICR(CD-1®) mice. The animals (6 per group, 3 males and 3 females), received the drug intravenously in a 10 ml/kg volume.

Both toxicity studies revealed no obvious treatment-related adverse reactions, no gross pathological findings, no changes in body weight and no mortality incidences observed even at the highest dose administered. Furthermore, blood samples taken from animals in the high-dose group, which had been administered with 10-fold the clinical dose, were tested for hematology and clinical chemistry. All hematology and clinical chemistry values were in normal ranges. In addition, the animals treated with the high dose were subjected to histopathological examination of the liver, spleen and kidney, and there were no macro or micro histopathological findings.

Example 5

Glycosylation Analysis

Analysis of glycan structures present on rGCD produced as described with regard to the previous Examples was performed. As described in greater detail below, results indicate that the majority of glycans contain terminal mannose residues as well as high mannose structures. Advantageously, this high mannose product was found to be biologically active, and therefore no further steps were needed for its activation.

The following methods were used to determine the glycosylation structure of the recombinant hGCD produced according to the Examples given above. Briefly, the monosaccharide linkages for both N- and O-glycans were determined by using a hydrolysis and GC-MS strategy. This method estimates the linkage type of the carbohydrates to the peptide and the general monosaccharide composition of a glycoprotein. Based on prior knowledge and also the ratios between various monosaccharides, this method may suggest the types of glycans on the glycoprotein. This information is important to estimate the possible glycan structures present on the protein.

Another method featured oligosaccharide analysis of the N-glycan population. FAB-MS and MALDI-TOF MS were performed, following digestion of aliquots of the samples with trypsin and peptide N-glycosidase F (PNGaseF) and permethylation of the glycans. This method is used to detach and isolate N-linked carbohydrates from the enzymatically digested glycoprotein. The masses of the glycan populations in the isolated glycan mix are determined and their masses are compared with those of known structures from databases and in light of the monosaccharide composition analysis. The proposed structures are based also on the glycosylation patterns of the source organism.

Another method included analyzing the O-glycan population following reductive elimination of the tryptic and PNGase F treated glycopeptides, desalting and permethylation. O-glycans are not released by PNGase F, therefore, glycans remaining linked to peptides are most likely O-linked glycans. These glycans are then released by reductive elimination and their mass analyzed.

Monosaccharide composition analysis (summarized below) revealed a characteristic distribution of hexoses, hexosamines and pentoses characteristic of plant glycosylation. The ratios between GlcNac and Mannose, suggest that characteristic N-linked structures are the predominant glycan population.

Mass Spectrometric analysis of the N-glycans from hGCD produced as described above indicates that the predominant N-glycan population has the monosaccharide composition Pent.deoxyHex.Hex3.HexNAc2.

Materials and Methods

Analysis was performed using a combination of Gas Chromatography-Mass Spectrometry (GC-MS), Fast Atom Bombardment-Mass Spectrometry (FAB-MS) and Delayed Extraction-Matrix Assisted Laser Desorption Ionisation-Time of Flight Mass-Spectrometry (DE-MALDI-TOF MS).

For oligosaccharide analysis, the N-glycan population was analysed by FAB-MS and MALDI-TOF MS following digestion of aliquots of the samples with trypsin and peptide N-glycosidase F (PNGaseF) and permethylation of the glycans. The O-glycan population was analysed following reductive elimination of the tryptic and PNGase F treated glycopeptides, desalting and permethylation.

The monosaccharide linkages for both N- and O-glycans were determined using a hydrolysis, derivatisation GC-MS strategy.

Experimental Description

Sample

The sample vials were received were given the unique sample numbers as follows (Table 1):

TABLE 1

| Product | reference number |
| --- | --- |
| Glucocerebrosidase. Four tubes containing | 62995 |
| 1 ml of sample each at a stated | 62996 |
| concentration of 0.8 mg/ml in 25 mM | 62997 |
| Citrate Buffer pH6.0, 0.01% Tween 80 | 62998 |

The samples were stored between −10 and −30° C. until required.

Protein Chemistry

Dialysis of Intact Samples

One vial (containing 1 ml of protein at a stated concentration of 0.8 mg/ml) was injected into a Slide-A-Lyzer dialysis cassette (10 kDa molecular weight cutoff) and dialysed at 4° C. over a period of 24 hours against water, the water being changed 3 times. Following dialysis the sample was removed form the cassette and lyophilised.

Trypsin Digestion of the Intact Samples for Oligosaccharide Screening

The dialysed, lyophilised sample was resuspended in 50 mM ammonium bicarbonate buffer adjusted to pH 8.4 with 10% aq. ammonia and digested with TPCK treated trypsin for 4 hours at 37° C. according to SOPs B001 and B003. The reaction was terminated by placing in a heating block at 95° C. for 2 minutes followed by lyophilisation.

Carbohydrate Chemistry

Peptide N-Glycosidase A Digestion

The tryptically cleaved peptide/glycopeptide mixtures from the glycoprotein sample was treated with the enzyme peptide N-glycosidase A (PNGaseA) in ammonium acetate buffer, pH 5.5 at 37° C. for 15 hours. The reaction was stopped by freeze-drying. The resulting products were purified using a $C_{18}$ Sep-Pak cartridge.

Reductive Elimination

The Sep-Pak fraction containing potential O-linked glycopeptides was dissolved in a solution of 10 mg/ml sodium borohydride in 0.05M sodium hydroxide and incubated at 45° C. for 16 hours. The reaction was terminated by the addition of glacial acetic acid.

Desalting of Reductively Eliminated Material

Desalting using Dowex beads was performed according to SOP B022. The sample was loaded onto the column and eluted using 4 ml of 5% aq. acetic acid. The collected fraction was lyophilised.

Permethylation of Released Carbohydrates

N-linked carbohydrates eluting in the 5% aq. acetic acid Sep-Pak fraction and potential O-linked glycans released by reductive elimination, were permethylated using the sodium hydroxide (NaOH)/methyl iodide (MeI) procedure (SOP B018). A portion of the permethylated N-linked glycan mixture was analysed by FAB-MS and MALDI-TOF MS and the remainder was subjected to linkage analysis.

Linkage Analysis of the N-Linked Carbohydrate

Derivatisation

The permethylated glycan sample mixtures obtained following tryptic and PNGase A digestion or reductive elimination were hydrolysed (2M TFA, 2 hours at 120° C.) and reduced (sodium borodeuteride ($NaBD_4$) in 2M $NH_4OH$, 2 hours at room temperature, SOP B025). The borate produced on the decomposition of the borodeuteride was removed by 3 additions of a mixture of methanol in glacial acetic acid (90:10) followed by lyophilisation. The samples were then acetylated using acetic anhydride (1 hour at 100° C.). The acetylated samples were purified by extraction into chloroform. The partially methylated alditol acetates were then examined by gas chromatography/mass spectrometry (GC/MS). Standard mixtures of partially methylated alditol acetates and a blank were also run under the same conditions.

Gas Liquid Chromatography/Mass Spectrometry (GC/MS)

An aliquot (1 μl) of the derivatised carbohydrate samples dissolved in hexane, were analysed by GC/MS using a Perkin Elmer Turbomass Gold mass spectrometer with an Autosystem XL gas chromatograph and a Dell data system under the following conditions:

Gas Chromatography
Column: DB5
Injection: On-column
Injector Temperature: 40° C.
Programme: 1 minute at 40° C. then 70° C./minute to 100° C., held at 100° C. for 1 minute, then 8° C./minute to 290° C., finally held at 290° C. for 5 minutes.
Carrier Gas: Helium
Mass Spectrometry
Ionisation Voltage: 70 eV
Acquisition: Mode Scanning
Mass Range: 35-450 Daltons
MS Resolution: Unit Sugar Analysis of Intact Glucocerebrosidase Derivatisation An aliquot equivalent to 500 μg of glucocerebrosidase was lyophilised with 10 μg of Arabitol as internal standard. This was then methanolysed overnight at 80° C. and dried under nitrogen. Released monosaccharides were re-N-acetylated using a solution of methanol, pyridine and acetic anhydride, dried under nitrogen again and converted to their trimethylsilyl (TMS) derivatives according to SOP B023. The TMS derivatives were reduced in volume under nitrogen, dissolved in 2 ml of hexane and sonicated for 3 minutes. The samples were then allowed to equilibrate at 4° C. overnight. A blank containing 10 μg of Arabitol and a standard monosaccharide mixture containing 10 μg each of Fucose, Xylose, Mannose, Galactose, Glucose, N-acetylgalactosamine, N-acetylglucosamine, N-acetylneuraminic acid and Arabitol were prepared in parallel. The TMS derivatives were then examined by gas chromatography/mass spectrometry (GC/MS).

Gas Liquid Chromatography/Mass Spectrometry (GC/MS)

An aliquot (1 μl) of the derivatised carbohydrate sample dissolved in hexane, was analysed by GC/MS using a Perkin Elmer Turbomass Gold mass spectrometer with an Autosystem XL gas chromatograph and a Dell data system under the following conditions:

Gas Chromatography
Column: DB5
Injection: On-column
Injector Temperature: 40° C.
Programme: 1 minute at 90° C. then 25° C./minute to 140° C., 5° C./minute to 220° C., finally 10° C./minute to 300° C. and held at 300° C. for 5 minutes.
Carrier Gas: Helium
Mass Spectrometry
Ionisation Voltage: 70 eV
Acquisition Mode Scanning
Mass Range: 50-620 Daltons
MS Resolution: Unit Delayed Extraction Matrix Assisted Laser Desorption Ionisation Mass Spectrometry (DE-MALDI-MS) and Fast Atom Bombardment-Mass Spectrometry (FAB-MS)

MALDI-TOF mass spectrometry was performed using a Voyager STR Biospectrometry Research Station Laser-Desorption Mass Spectrometer coupled with Delayed Extraction (DE).

Dried permethylated glycans were redissolved in methanol:water (80:20) and analysed using a matrix of 2,5-dihydroxybenzoic acid. Bradykinin, Angiotensin and ACTH were used as external calibrants.

Positive Ion Fast Atom Bombardment mass spectrometric analyses were carried out on M-Scan's VG AutoSpecE mass spectrometer operating at Vacc=8 kV for 4500 mass range at full sensitivity with a resolution of approximately 2500. A Caesium Ion Gun was used to generate spectra operating at 30 kV. Spectra were recorded on a VAX data system 3100 M76 using Opus software.

Dried permethylated glycans were dissolved in methanol and loaded onto a target previously smeared with 2-4 µl of thioglycerol as matrix prior to insertion into the source.

In a second set of glycosylation analysis, similar methods were used to determine the glycosylation patterns, and to identify the major glycosylated products produced by the carrot cell suspension culture of the present invention:

Glycosylation patterns were analyzed by the Glycobiology Center of the National Institute for Biotechnology (Ben Gurion University, Beer Sheba, Israel) to determine glycan structure and relative amounts using sequential digestion with various exoglycosidases. The plant GCD samples of the invention were run on SDS-PAGE and a 61 KDa band was cut out and incubated with either PNGase A, or with trypsin followed by PNGase A to release the N-linked glycans. The glycans were fluorescently labeled with anthranilamide (2AB) and run on normal phase HPLC.

Sequencing of the labeled glycan pool was achieved by sequential digestion with various exoglycosidases followed by HPLC analysis. Retention times of individual glycans were compared to those of a standard partial hydrolysate of dextran giving a ladder of glucose units (GU). Unlabeled glycans were further purified and analyzed by MALDI mass spectrometry. Exoglycosidases used: Bovine kidney _-fucosidase (digests _1-6 and _1-3 core fucose, Prozyme), Jack bean mannosidase (removes _1-2, 6>3 mannose, Prozyme), *Xanthomonas* beta-1,2-xylosidase (removes _1-2 xylose only after removal of _-linked mannose, Calbiochem).

Bovine testes-galactosidase (hydrolyses non-reducing terminal galactose _1-3 and _1-4 linkages, Prozyme), *Streptococcus pneumoniae* hexosaminidase (digest _1-2,3,4,6 GalNAc and GlcNAc, Prozyme). Glycosylation was further analyzed by M-Scan (Berkshire, England) using gas chromatography mass spectrometry (GC-MS), fast atom bombardment-mass spectrometry (FAB-MS), and delayed extraction-matrix assisted laser desorption ionization—time of flight mass-spectrometry (DE-MALDI-TOF MS). For oligosaccharide determination, the N-glycan population was analyzed by FAB-MS and MALDI-TOF MS, following digestion of samples with trypsin and PNGase A, and permethylation of the glycans. O-glycans were analyzed following reductive elimination of the tryptic and PNGase A-treated glycopeptides, desalting and permethylation.

The similarity of the N-glycans in different batches of prGCD was analyzed by high performance anion exchange chromatography with pulsed amperometric detection (HPAEC-PAD, a Dionex method) following digestion with trypsin and PNGase A, to obtain chromatographic profiles for oligosaccharides released from glycoproteins for the purpose of demonstrating consistency from batch to batch of prGCD. This procedure permits chromatographic comparison of oligosaccharide patterns in a qualitative and quantitative manner.

Results and Discussion

TMS Sugar Analysis of Glucocerebrosidase

N-Linked Oligosaccharide Screening

The intact glycoprotein was subjected to dialysis followed by trypsin digestion and the lyophilised products were digested using PNGase A and then purified using a $C_{18}$ Sep-Pak. The 5% aq. acetic acid (N-linked oligosaccharide containing) fraction was permethylated and FAB mass spectra were obtained using a portion of the derivatised oligosaccharide in a low mass range for fragment ions and DE-MALDI-TOF mass spectra were obtained using a portion of the derivatised oligosaccharides in a high mass range for molecular ions.

Analysis of N-Glycans from Glucocerebrosidase

Table 1 lists the predominant fragment ions present in the FAB spectra and molecular ions present in the MALDI spectra. The molecular ion region (shown in Appendix III) contains a predominant signal at m/z 1505.8 (consistent with an $[M+Na]^+$ quasimolecular ion for a structure having the composition $Pent.deoxyHex.Hex_3.HexNAc_2$). A range of less intense quasimolecular ions were also detected consistent with complex and high mannose structures. The high mannose structures detected range in size from $Hex_5.HexNAc_2$ at m/z 1579.8 to $Hex_8.HexNAc_2$ at m/z 2193.0. The complex signals are produced from less extensively processed N-glycans such as m/z 1331.7 (consistent with an $[M+Na]^+$ quasimolecular ion for a structure having the composition $Pent.Hex_3.HexNAc_2$) or from larger N-glycans for example m/z 1751.0 (consistent with an $[M+Na]^+$ quasimolecular ion for a structure having the composition $Pent.deoxyHex.Hex_3.HexNAc_3$), m/z 2375.4 (consistent with an $[M+Na]^+$ quasimolecular ion for a structure having the composition $Pent.deoxyHex_2.Hex_4.HexNAc_4$) and m/z 2753.6 (consistent with an $[M+Na]^+$ quasimolecular ion for a structure having the composition $Pent.deoxyHex_3.Hex_5.HexNAc_4$).

The FAB mass spectrum provides information regarding antennae structures by virtual of fragment ions in the low mass region of the spectrum (data not shown).

Signals were detected identifying hexose (at m/z 219) and HexNAc (at m/z 260) as non-reducing terminal monosaccharides in the N-glycans.

TABLE 2

Masses observed in the permethylated spectra of Glucocerebrosidase (reference number 62996) following Tryptic and Peptide N-glycosidase A digestion

| Signals observed (m/z) | Possible Assignment |
|---|---|
| Low Mass | |
| 219 | $Hex^+$ |
| 228 | $HexNAc^+$ (−methanol) |
| 260 | $HexNAc^+$ |
| High Mass | |
| 1032.4 | $Pent•Hex_3•HexNAc^+$ |
| 1171.5 | $Hex_3•HexNAc_2OMe + Na^+$ |
| 1299.6 | Elimination of fucose from m/z 1505.8 |
| 1331.6 | $Pent•Hex_3•HexNAc_2OMe + Na^+$ |
| 1345.6 | $deoxyHex•Hex_3•HexNAc_2OMe + Na^+$ |
| 1505.7 | $Pent•deoxyHex•Hex_3•HexNAc_2OMe + Na^+$ |
| 1579.8 | $Hex_5•HexNAc_2OMe + Na^+$ |
| 1709.9 | $Pent•deoxyHex•Hex_4•HexNAc_2OMe + Na^+$ |
| 1750.9 | $Pent•deoxyHex•Hex_3•HexNAc_3OMe + Na^+$ |
| 1783.9 | $Hex_6•HexNAc_2OMe + Na^+$ |
| 1989.0 | $Hex_7•HexNAc_2OMe + Na^+$ |
| 1997.0 | $Pent•deoxyHex•Hex_3•HexNAc_4OMe + Na^+$ |
| 2027.0 | Not assigned |
| 2099.0 | Not assigned |
| 2130.0 | $Pent•deoxyHex_2•Hex_4•HexNAc_3OMe + Na^+$ |
| 2193.1 | $Hex_8•HexNAc_2OMe + Na^+$ |
| 2375.2 | $Pent•deoxyHex_2•Hex_4•HexNAc_4OMe + Na^+$ |
| 2753.4 | $Pent•deoxyHex_3•Hex_5•HexNAc_4OMe + Na^+$ |

All masses in column one are monoisotopic unless otherwise stated. The mass numbers may not relate directly to the raw data as the software often assigns mass numbers to $^{13}C$ isotope peaks particularly for masses above 1700 Da.

Linkage analysis of N-glycans from Glucocerebrosidase

Linkage analysis was performed on the N-linked carbohydrates released following PNGase A digestion, Sep-Pak purification and permethylation.

A complex chromatogram was obtained with some impurity peaks originating from the derivatising reagents. Comparison of the retention time and the spectra with standard mixtures allowed provisional assignments of the sugar containing peaks listed in Table 3.

TABLE 3

Retention times of the variously linked monosaccharides detected as their partially methylated alditol acetates in the GC-MS analysis of Glucocerebrosidase (reference number 62996) following Tryptic and Peptide N-glycosidase A digestion

| Compounds Observed | Retention time (mins) Glucocerebrosidase (62996) |
|---|---|
| Terminal Xylose | 10.41 |
| Terminal Fucose | 10.84 |
| Terminal Mannose | 12.29 (major) |
| Terminal Galactose | 12.55 |
| 2-linked Mannose | 13.40 |
| 4-linked Glucose | 13.58 |
| 2,6-linked Mannose | 14.91 |
| 3,6-linked Mannose | 15.08 |
| 2,3,6-linked Mannose | 15.87 |
| 4-linked GlcNAc | 16.73 |
| 3,4-linked GlcNAc | 17.59 |

4.3 O-Linked Oligosaccharide Screening

Reductive elimination was carried out on the 60% 2-propanol fraction (potential O-linked glycopeptide fraction) from the Sep-Pak purification of Glucocerebrosidase following trypsin and PNGase A digestions. The sample was desalted following termination of the reaction and, after borate removal, was permethylated. FAB mass spectra were obtained using a portion of the derivatised oligosaccharide in a low mass range for fragment ions and DE-MALDI-TOF mass spectra were obtained using a portion of the derivatised oligosaccharides in a high mass range for molecular ions. No signals consistent with the presence of O-linked glycans were observed (data not shown).

Linkage Analysis of O-glycans from Glucocerebrosidase

Linkage analysis was carried out on the products of reductive elimination after permethylation. No signals consistent with the presence of typical O-linked glycans were observed (data not shown).

Figure 6:
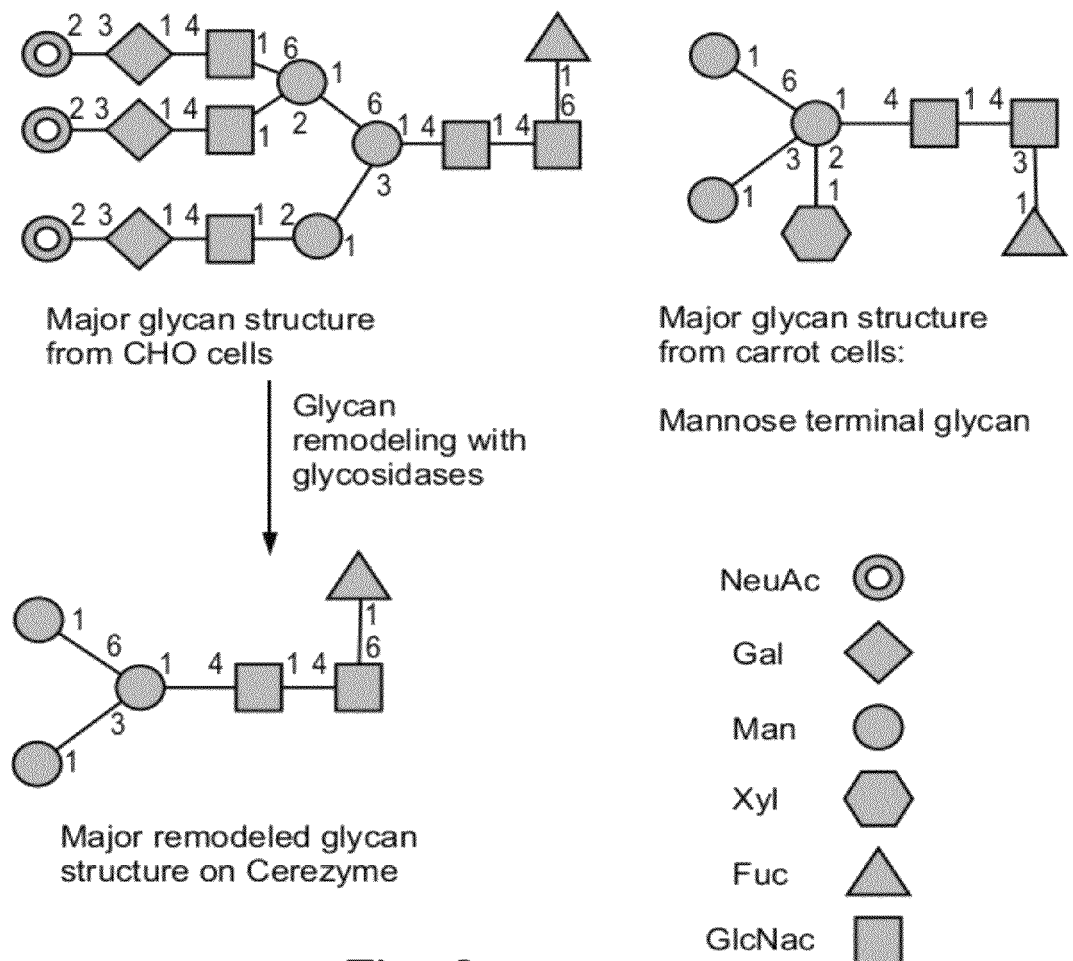
FIG. 6 shows comparative glycosylation structures for rGCD according to the present invention and that of Cerezyme™.

FIG. 6 shows some exemplary glycan structures as a comparison between GCD obtained from CHO (Chinese hamster ovary) cells, which are mammalian cells (Cerezyme™) and the GCD of the present invention, from carrot cells. As shown, remodeling of these structures is required to obtain exposed mannose residues for Cerezyme™. By contrast, such exposed mannose residues are directly obtained for the GCD obtained from plant cells according to the present invention, without requiring further manipulation, for example with glycosylases.

Figure 7:
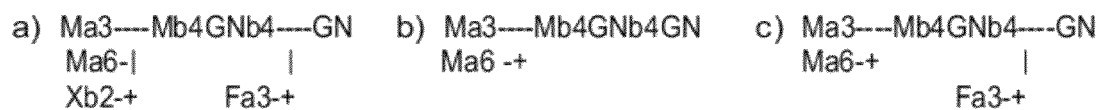
FIG. 7 shows glycosylation structures for rGCD according to the present invention.
Figure 8A:
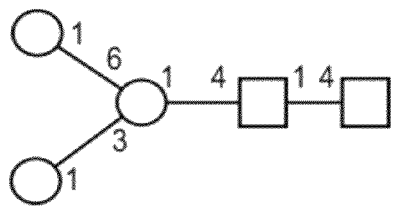
FIG. 8a-8d shows additional N-glycan glycosylation structures for rGCD according to the present invention.
Figure 8A:
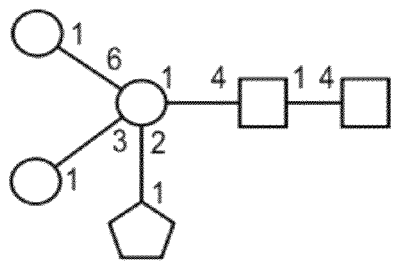
Figure 8A:
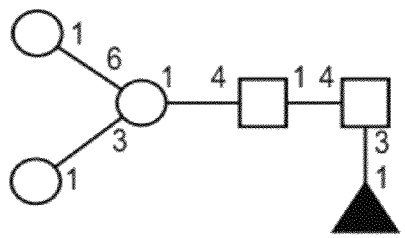
Figure 8A:
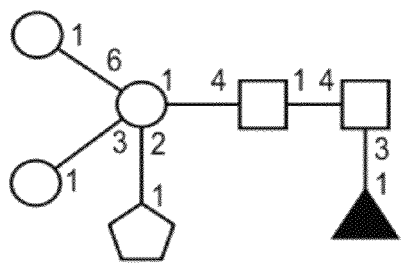
Figure 8B:
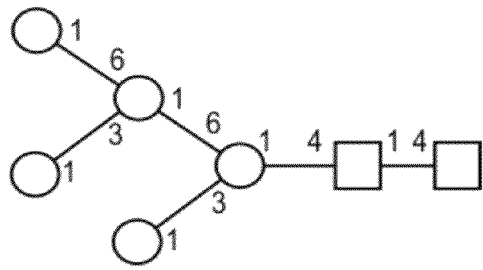
Figure 8B:
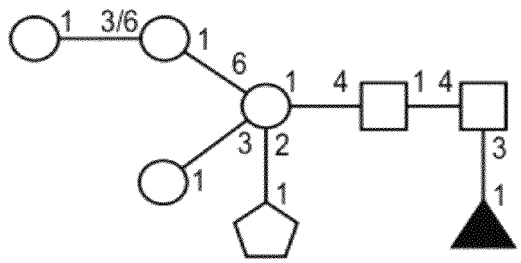
Figure 8B:
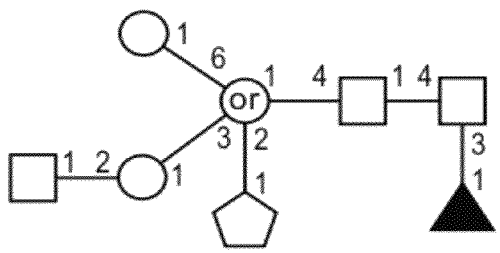
Figure 8B:
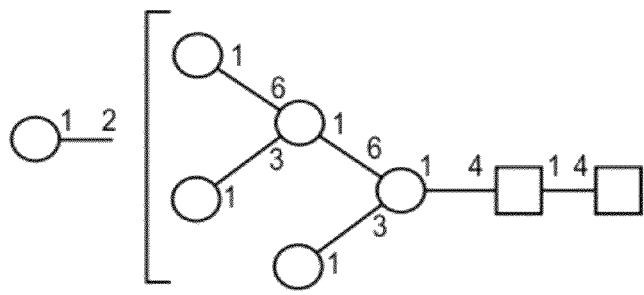
Figure 8C:
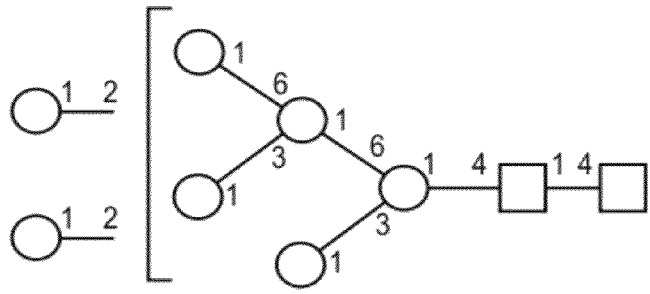
Figure 8C:
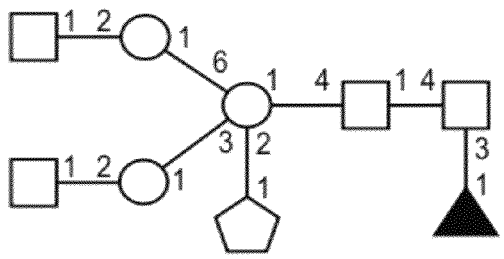
Figure 8C:
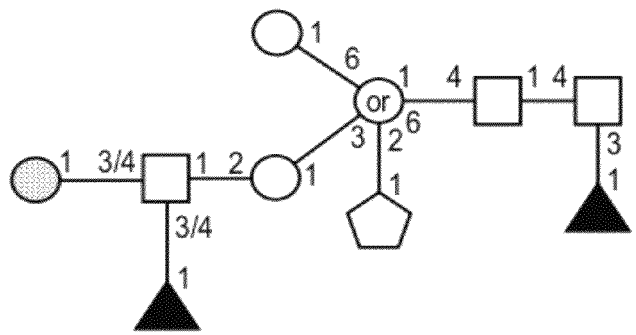
Figure 8C:
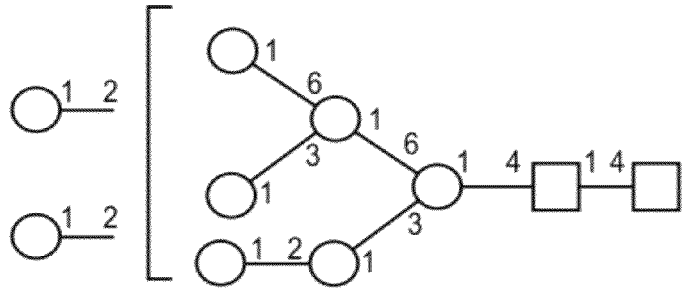
Figure 8D:
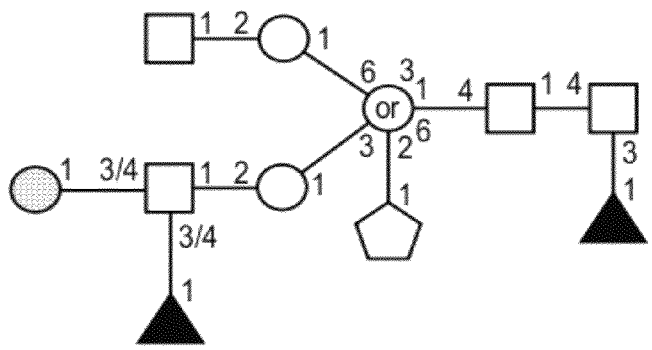
Figure 8D:
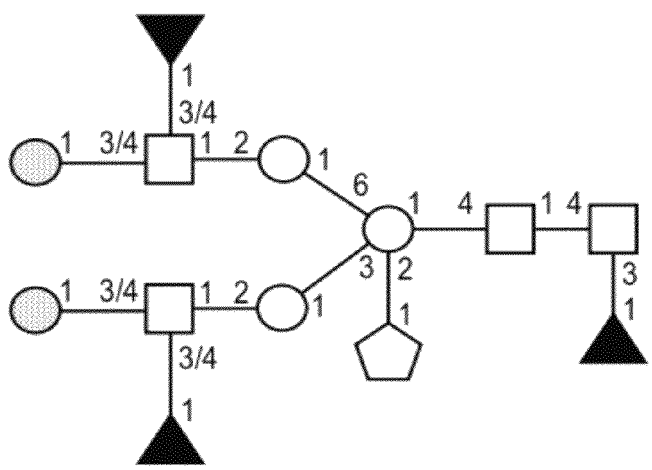

FIG. 7 represents the main glycan structure found in rGCD. FIG. 7 shows proposed structures of: a) the predominant oligosaccharide population found on hGC expressed in carrot cell suspension (1505.7 m/z); b) typical N-linked core; c) Fucosylated plant N-linked core. N-linked glycans are coupled to the protein via-Aspargine and through the reducing end of the GlcNac (GN) residue on the right hand of the diagrams. N plant glycosylation patterns, Fucose residues may be part of the core structure, bound to the first GlcNac using an alpha(1-3) glycosidic bond, while mammalian structures typically use the alpha(1-6) glycosidic bond.

FIGS. 8A-8D show all possible structures for the N-glycans detected on the rGCD protein according to the present invention.

The dominant glycan structure that was identified is the core glycan structure found in most plant glycoproteins from pea, rice, maize and other edible plants. This structure contains a core xylose residue as well as a core alpha-(1,3)-fucose. Work done by Bardor et al (33) shows that 50% of nonallergic blood donors have specific antibodies for core xylose in their sera, and 25% have specific antibodies to core alpha-(1,3)-fucose. However it is still to be studied whether such antibodies might introduce limitations to the use of plant-derived biopharmaceutical glycoproteins.

The minor glycan populations of the hGCD produced as described above were mainly high mannose structures Hex4HexNAc2 to Hex8HexNAc2. Among the complex structures exhibited structures such as Pent.deoxyHex2.Hex4.HexNAc3 and Pent.deoxyHex3.Hex5.HexNAc3. Pent.Hex3.HexNAc2 was detected in smaller proportions.

The major terminal monosaccharides are hexose (Mannose or Galactose) and N-acetylhexosamine, which is consistent with the presence of high mannose structures and partially processed complex structures.

With regard to O-linked oligosaccharide screening, no signals that are consistent with typical O-linked glycans were observed. GCD is known in the art to not have O-linked oligosaccharides, such that these results are consistent with the known glycosylation of GCD from other cell systems, including native GCD and recombinant GCD produced in mammalian culture systems. However, in the monosaccharide composition, signals consistent with Arabinose were detected.

An important point with regard to the present invention is that the hGCD protein N-glycan composition analysis showed that the majority of the N-glycans terminate with mannose residues. This agrees with the requirement for mannose terminating N-glycans assisting the uptake of therapeutic hGCD by the macrophage mannose receptor. However, neither native GCD nor recombinant GCD produced in mammalian cells is high mannose. Therefore, the present invention overcomes a significant drawback of commercially produced hGCD proteins, which is that these proteins are modified to terminate with mannose sugars, unlike the protein produced as described above.

Figure 10A:
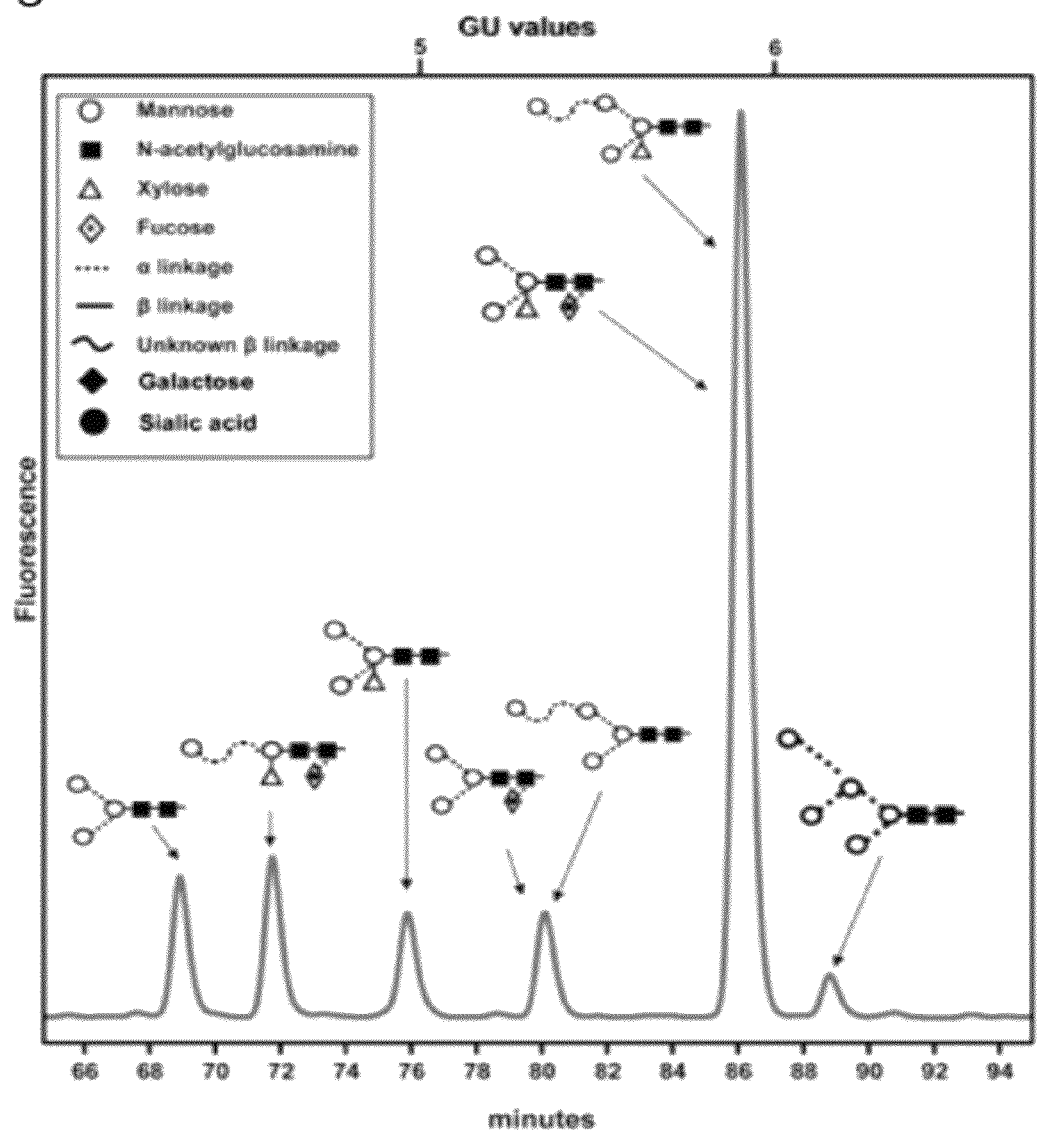
FIGS. 10a-10b are schematic representations of the glycan structures of the recombinant human GCD of the present invention.
Figure 10B:
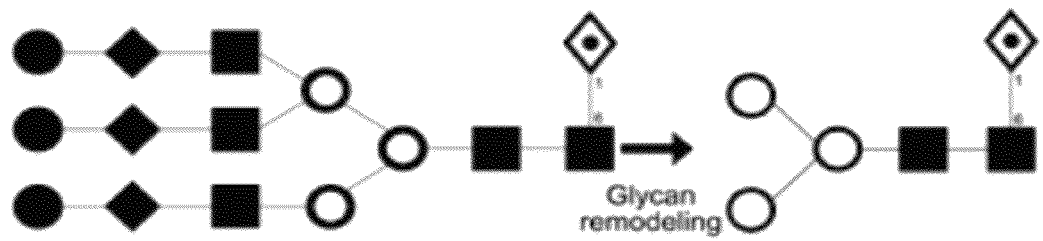
Figure 11:
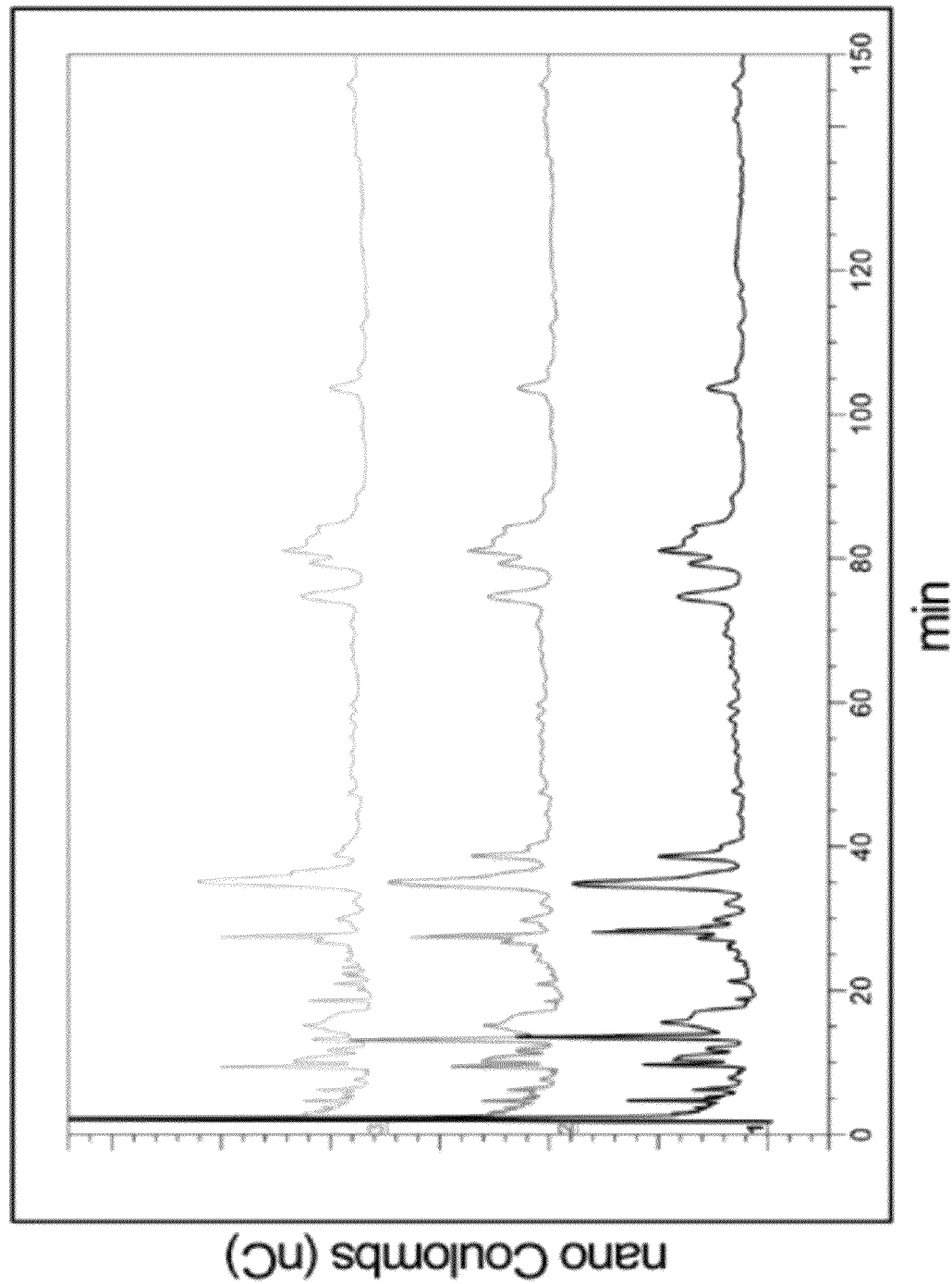
FIG. 11 is a HP-anion exchange chromatography analysis of the gycan profile of the recombinant human GCD of the present invention, showing the consistent and reproducible glycan structure of recombinant human GCD from batch to batch.

Further glycosylation analysis was performed on a purified human recombinant glucocerebrosidase prepared in plant cells. Glycosylation was analyzed (Glycobiology Center of the National Institute for Biotechnology (Ben Gurion University, Beer Sheba, Israel) to determine glycan structure and the glycan quantitative ratio using sequential digestion with various exoglycosidases (see Methods, above). In this analysis, it was found that the N-linked glycans have a main core of two GlcNAc residues and a 1-4 linked mannose, attached to two additional mannose residues in __1-3 and __1-6 linkages. The additional residues found are shown in FIG. 10a, which presents all structures and their relative amounts based upon HPLC, enzyme array digests and MALDI. FIG. 10b shows the glycan structure of Cerezyme® before and after in vitro enzymatic processing. Notably, analysis of the glycan structures of the GCD of the invention revealed that >90% of the glycans were mannose-rich, bearing exposed, terminal mannose residues (FIG. 10a), whereas in the case of Cerezyme®, mannose residues are exposed only after a complex in-vitro procedure (FIG. 10b). The dominant glycan in the GCD of the invention is the core structure found in most glycoproteins purified from pea, rice, maize and other edible plants. This structure contains a core _-(1,2)-xylose residue as well as a core _-(1,3)-fucose (FIG. 10a). The DE-MALDI-MS data contained no signals consistent with typical O-linked glycans. Further analysis of the glycan profiles for the GCD of the invention obtained from different production batches was performed in order to assess the batch-to-batch reproducibility of the GCD produced in the carrot cell system. As presented in FIG. 11, the population of glycans on plant GCD of the invention is highly reproducible between batches.

Example 6

Treatment with the Present Invention

The recombinant protein produced according to the present invention preferably comprises a suitably glycosylated protein produced by a plant cell culture, which is preferably a lysosomal enzyme for example, and/or a high mannose glycosylated protein.

According to preferred embodiments herein, the protein produced according to the present invention is suitable for treatment of a lysosomal-associated disease, such as a lysosomal storage disease for example.

The method of treatment optionally and preferably comprises: (a) providing a recombinant biologically active form of lysosomal enzyme purified from transformed plant root cells, and capable of efficiently targeting cells abnormally deficient in the lysosomal enzyme. This recombinant biologically active enzyme has exposed terminal mannose residues on appended oligosaccharides; and (b) administering a therapeutically effective amount of the recombinant biologically active lysosomal enzyme, or of composition comprising the same to the subject. In a preferred embodiment, the recombinant high mannose lysosomal enzyme used by the method of the invention may be produced by the host cell of the invention. Preferably, this host cell is a carrot cell.

By "mammalian subject" or "mammalian patient" is meant any mammal for which gene therapy is desired, including human, bovine, equine, canine, and feline subjects, most preferably, a human subject.

It should be noted that the term "treatment" also includes amelioration or alleviation of a pathological condition and/or one or more symptoms thereof, curing such a condition, or preventing the genesis of such a condition.

In another preferred embodiment, the lysosomal enzyme used by the method of the invention may be a high mannose enzyme comprising at least one oligosaccharide chain having an exposed mannose residue. This recombinant enzyme can bind to a mannose receptor on a target cell in a target site within a subject. More preferably, this recombinant lysosomal enzyme has increased affinity for these target cell, in comparison with the corresponding affinity of a naturally occurring lysosomal enzyme to the target cell. Therefore, each dose is dependent on the effective targeting of cells abnormally deficient in GCD and each dose of such form of GCD is substantially less than the dose of naturally occurring GCD that would otherwise be administered in a similar manner to achieve the therapeutic effect.

According to preferred embodiments of the present invention, the protein is suitable for the treatment of lysosomal storage diseases, such that the present invention also comprises a method for treating such diseases. Lysosomal storage diseases are a group of over 40 disorders which are the result of defects in genes encoding enzymes that break down glycolipid or polysaccharide waste products within the lysosomes of cells. The enzymatic products, e.g., sugars and lipids, are then recycled into new products. Each of these disorders results from an inherited autosomal or X-linked recessive trait which affects the levels of enzymes in the lysosome. Generally, there is no biological or functional activity of the affected enzymes in the cells and tissues of affected individuals. In such diseases the deficiency in enzyme function creates a progressive systemic deposition of lipid or carbohydrate substrate in lysosomes in cells in the body, eventually causing loss of organ function and death. The genetic etiology, clinical manifestations, molecular biology and possibility of the lysosomal storage diseases are detailed in Scriver et al. [Scriver et al. eds., The Metabolic and Molecular Basis of Inherited Disease, $7^{th}$ Ed., Vol. II, McGraw Hill, (1995)].

Examples of lysosomal storage diseases (and their associated deficient enzymes) include but are not limited to Fabry disease (α-galactosidase), Farber disease (ceramidase), Gaucher disease (glucocerebrosidase), $G_{m1}$ gangliosidosis (β-galactosidase), Tay-Sachs disease (β-hexosaminidase), Niemann-Pick disease (sphingomyelinase), Schindler disease (α.-N-acetylgalactosaminidase), Hunter syndrome (iduronate-2-sulfatase), Sly syndrome (β-glucuronidase), Hurler and Hurler/Scheie syndromes (iduronidase), and I-Cell/San Filipo syndrome (mannose 6-phosphate transporter).

Gaucher disease is the most common lysosomal storage disease in humans, with the highest frequency encountered in the Ashkenazi Jewish population. About 5,000 to 10,000 people in the United States are afflicted with this disease [Grabowski, Adv. Hum. Genet. 21:377-441 (1993)]. Gaucher disease results from a deficiency in glucocerebrosidase (hGCD; glucosylceramidase). This deficiency leads to an accumulation of the enzyme's substrate, glucocerebroside, in reticuloendothelial cells of the bone marrow, spleen and liver, resulting in significant skeletal complications such as bone marrow expansion and bone deterioration, and also hypersplenism, hepatomegaly, thrombocytopenia, anemia and lung complications [Grabowski, (1993) ibid.; Lee, Prog. Clin. Biol. Res. 95:177-217 (1982)].

More specifically, the lysosomal enzyme used by the method of the invention may be selected from the group consisting of glucocerebrosidase (GCD), acid sphingomyelinase, hexosaminidase, α-N-acetylgalactosaminidise, acid lipase, α-galactosidase, glucocerebrosidase, α-L-iduronidase, iduronate sulfatase, α-mannosidase or sialidase. Preferably, where the treated disease is Gaucher's disease, the lysosomal enzyme used by the method of the invention is glucocerebrosidase (GCD).

The protein of the present invention can be used to produce a pharmaceutical composition. Thus, according to another aspect of the present invention there is provided a pharmaceutical composition which includes, as an active ingredient thereof, a protein and a pharmaceutical acceptable carrier. As used herein a "pharmaceutical composition" refers to a preparation of one or more of the active ingredients described herein, such as a recombinant protein, with other chemical components such as traditional drugs, physiologically suitable carriers and excipients. The purpose of a pharmaceutical composition is to facilitate administration of a protein or cell to an organism. Pharmaceutical compositions of the present invention may be manufactured by processes well known in the art, e.g., by means of conventional mixing, dissolving, granulating, dragee-making, levigating, emulsifying, encapsulating, entrapping or lyophilizing processes.

In a preferred embodiment, the term "pharmaceutically acceptable" means approved by a regulatory agency of the Federal or a state government or listed in the U.S. Pharmacopeia or other generally recognized pharmacopeia for use in animals, and more particularly in humans. Hereinafter, the phrases "physiologically suitable carrier" and "pharmaceutically acceptable carrier" are interchangeably used and refer to an approved carrier or a diluent that does not cause significant irritation to an organism and does not abrogate the biological activity and properties of the administered conjugate.

The term "carrier" refers to a diluent, adjuvant, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like. The composition can be formulated as a suppository, with traditional binders and carriers such as triglycerides.

Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in "Remington's Pharmaceutical Sciences" by E. W. Martin. Such compositions will contain a therapeutically effective amount of the protein, preferably in purified form, together with a suitable amount of carrier so as to provide the form for proper administration to the patient. The formulation should be suitable for the mode of administration.

Herein the term "excipient" refers to an inert substance added to a pharmaceutical composition to further facilitate processes and administration of the active ingredients. Examples, without limitation, of excipients include calcium carbonate, calcium phosphate, various sugars and types of starch, cellulose derivatives, gelatin, vegetable oils and polyethylene glycols.

Further techniques for formulation and administration of active ingredients may be found in "Remington's Pharmaceutical Sciences," Mack Publishing Co., Easton, Pa., latest edition, which is incorporated herein by reference as if fully set forth herein.

The pharmaceutical compositions herein described may also comprise suitable solid or gel phase carriers or excipients. Examples of such carriers or excipients include, but are not limited to, calcium carbonate, calcium phosphate, various sugars, starches, cellulose derivatives, gelatin and polymers such as polyethylene glycols.

Suitable routes of administration may, for example, include oral, rectal, transmucosal, transdermal, intestinal or parenteral delivery, including intramuscular, subcutaneous and intramedullary injections as well as intrathecal, direct intraventricular, intravenous, intraperitoneal, intranasal, or intraocular injections.

Pharmaceutical compositions for use in accordance with the present invention thus may be formulated in conventional manner using one or more pharmaceutically acceptable carriers comprising excipients and auxiliaries, which facilitate processing of the active ingredients into preparations which, can be used pharmaceutically. Proper formulation is dependent upon the route of administration chosen.

For injection, the active ingredients of the invention may be formulated in aqueous solutions, preferably in physiologically compatible buffers such as Hank's solution, Ringer's solution, or physiological saline buffer. For transmucosal administration, penetrants are used in the formulation. Such penetrants are generally known in the art.

For oral administration, the active ingredients can be optionally formulated through administration of the whole cells producing a protein according to the present invention, such as GCD for example. The active ingredients can also be formulated by combining the active ingredients and/or the cells with pharmaceutically acceptable carriers well known in the art. Such carriers enable the active ingredients of the invention to be formulated as tablets, pills, dragees, capsules, liquids, gels, syrups, slurries, suspensions, and the like, for oral ingestion by a patient. Pharmacological preparations for oral use can be made using a solid excipient, optionally grinding the resulting mixture, and processing the mixture of granules, after adding suitable auxiliaries if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carbomethylcellulose; and/or physiologically acceptable polymers such as polyvinylpyrrolidone (PVP). If desired, disintegrating agents may be added, such as cross-linked polyvinyl pyrrolidone, agar, or alginic acid or a salt thereof such as sodium alginate.

Dragee cores are provided with suitable coatings. For this purpose, concentrated sugar solutions may be used which may optionally contain gum arabic, talc, polyvinyl pyrrolidone, carbopol gel, polyethylene glycol, titanium dioxide, lacquer solutions and suitable organic solvents or solvent mixtures. Dyestuffs or pigments may be added to the tablets or dragee coatings for identification or to characterize different combinations of active ingredient doses.

Pharmaceutical compositions, which can be used orally, include push-fit capsules made of gelatin as well as soft, sealed capsules made of gelatin and a plasticizer, such as glycerol or sorbitol. The push-fit capsules may contain the active ingredients in admixture with filler such as lactose, binders such as starches, lubricants such as talc or magnesium stearate and, optionally, stabilizers. In soft capsules, the active ingredients may be dissolved or suspended in suitable liquids, such as fatty oils, liquid paraffin, or liquid polyethylene glycols. In addition, stabilizers may be added. All formulations for oral administration should be in dosages suitable for the chosen route of administration.

For buccal administration, the compositions may take the form of tablets or lozenges formulated in conventional manner.

For administration by inhalation, the active ingredients for use according to the present invention are conveniently delivered in the form of an aerosol spray presentation from a pressurized pack or a nebulizer with the use of a suitable propellant, e.g., dichlorodifluoromethane, trichlorofluoromethane, dichloro-tetrafluoroethane or carbon dioxide. In the case of a pressurized aerosol, the dosage unit may be determined by providing a valve to deliver a metered amount. Capsules and cartridges of, e.g., gelatin for use in an inhaler or insufflator may be formulated containing a powder mix of the active ingredient and a suitable powder base such as lactose or starch.

The active ingredients described herein may be formulated for parenteral administration, e.g., by bolus injection or continuous infusion. Formulations for injection may be presented in unit dosage form, e.g., in ampoules or in multidose containers with optionally, an added preservative. The compositions may be suspensions, solutions or emulsions in oily or aqueous vehicles, and may contain formulatory agents such as suspending, stabilizing and/or dispersing agents.

Pharmaceutical compositions for parenteral administration include aqueous solutions of the active preparation in water-soluble form. Additionally, suspensions of the active ingredients may be prepared as appropriate oily injection suspensions. Suitable lipophilic solvents or vehicles include fatty oils such as sesame oil, or synthetic fatty acids esters such as ethyl oleate, triglycerides or liposomes. Aqueous injection suspensions may contain substances, which increase the viscosity of the suspension, such as sodium carboxymethyl cellulose, sorbitol or dextran. Optionally, the suspension may also contain suitable stabilizers or agents which increase the solubility of the active ingredients to allow for the preparation of highly concentrated solutions.

In a preferred embodiment, the composition is formulated in accordance with routine procedures as a pharmaceutical composition adapted for intravenous administration to human beings. Typically, pharmaceutical compositions for intravenous administration are solutions in sterile isotonic aqueous buffer. Generally, the ingredients are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The pharmaceutical compositions of the invention can be formulated as neutral or salt forms. Pharmaceutically acceptable salts include those formed with anions such as those derived from hydrochloric, phosphoric, acetic, oxalic, tartaric acids, etc., and those formed with cations such as those derived from sodium, potassium, ammonium, calcium, ferric hydroxides, isopropylamine, triethylamine, 2-ethylamino ethanol, histidine, procaine, etc.

The active ingredients of the present invention may also be formulated in rectal compositions such as suppositories or retention enemas, using, e.g., conventional suppository bases such as cocoa butter or other glycerides.

The pharmaceutical compositions herein described may also comprise suitable solid of gel phase carriers or excipients. Examples of such carriers or excipients include, but are not limited to, calcium carbonate, calcium phosphate, various sugars, starches, cellulose derivatives, gelatin and polymers such as polyethylene glycols.

The topical route is optionally performed, and is assisted by a topical carrier. The topical carrier is one which is generally suited for topical active ingredient administration and includes any such materials known in the art. The topical carrier is selected so as to provide the composition in the desired form, e.g., as a liquid or non-liquid carrier, lotion, cream, paste, gel, powder, ointment, solvent, liquid diluent, drops and the like, and may be comprised of a material of either naturally occurring or synthetic origin. It is essential, clearly, that the selected carrier does not adversely affect the active agent or other components of the topical formulation, and which is stable with respect to all components of the topical formulation. Examples of suitable topical carriers for use herein include water, alcohols and other nontoxic organic solvents, glycerin, mineral oil, silicone, petroleum jelly, lanolin, fatty acids, vegetable oils, parabens, waxes, and the like. Preferred formulations herein are colorless, odorless ointments, liquids, lotions, creams and gels.

Ointments are semisolid preparations, which are typically based on petrolatum or other petroleum derivatives. The specific ointment base to be used, as will be appreciated by those skilled in the art, is one that will provide for optimum active ingredients delivery, and, preferably, will provide for other desired characteristics as well, e.g., emolliency or the like. As with other carriers or vehicles, an ointment base should be inert, stable, nonirritating and nonsensitizing. As explained in Remington: The Science and Practice of Pharmacy, 19th Ed. (Easton, Pa.: Mack Publishing Co., 1995), at pages 1399-1404, ointment bases may be grouped in four classes: oleaginous bases; emulsifiable bases; emulsion bases; and water-soluble bases. Oleaginous ointment bases include, for example, vegetable oils, fats obtained from animals, and semisolid hydrocarbons obtained from petroleum. Emulsifiable ointment bases, also known as absorbent ointment bases, contain little or no water and include, for example, hydroxystearin sulfate, anhydrous lanolin and hydrophilic petrolatum. Emulsion ointment bases are either water-in-oil (W/O) emulsions or oil-in-water (O/W) emulsions, and include, for example, cetyl alcohol, glyceryl monostearate, lanolin and stearic acid. Preferred water-soluble ointment bases are prepared from polyethylene glycols of varying molecular weight; again, reference may be made to Remington: The Science and Practice of Pharmacy for further information.

Lotions are preparations to be applied to the skin surface without friction, and are typically liquid or semiliquid preparations, in which solid particles, including the active agent, are present in a water or alcohol base. Lotions are usually suspensions of solids, and may comprise a liquid oily emulsion of the oil-in-water type. Lotions are preferred formulations herein for treating large body areas, because of the ease of applying a more fluid composition. It is generally necessary that the insoluble matter in a lotion be finely divided. Lotions will typically contain suspending agents to produce better dispersions as well as active ingredients useful for localizing and holding the active agent in contact with the skin, e.g., methylcellulose, sodium carboxymethylcellulose, or the like.

Creams containing the selected active ingredients are, as known in the art, viscous liquid or semisolid emulsions, either oil-in-water or water-in-oil. Cream bases are water-washable, and contain an oil phase, an emulsifier and an aqueous phase. The oil phase, also sometimes called the "internal" phase, is generally comprised of petrolatum and a fatty alcohol such as cetyl or stearyl alcohol; the aqueous phase usually, although not necessarily, exceeds the oil phase in volume, and generally contains a humectant. The emulsifier in a cream formulation, as explained in Remington, supra, is generally a nonionic, anionic, cationic or amphoteric surfactant.

Gel formulations are preferred for application to the scalp. As will be appreciated by those working in the field of topical active ingredients formulation, gels are semisolid, suspension-type systems. Single-phase gels contain organic macro-molecules distributed substantially uniformly throughout the carrier liquid, which is typically aqueous, but also, preferably, contain an alcohol and, optionally, an oil.

Various additives, known to those skilled in the art, may be included in the topical formulations of the invention. For example, solvents may be used to solubilize certain active ingredients substances. Other optional additives include skin permeation enhancers, opacifiers, anti-oxidants, gelling agents, thickening agents, stabilizers, and the like.

The topical compositions of the present invention may also be delivered to the skin using conventional dermal-type patches or articles, wherein the active ingredients composition is contained within a laminated structure, that serves as a drug delivery device to be affixed to the skin. In such a structure, the active ingredients composition is contained in a layer, or "reservoir", underlying an upper backing layer. The laminated structure may contain a single reservoir, or it may contain multiple reservoirs. In one embodiment, the reservoir comprises a polymeric matrix of a pharmaceutically acceptable contact adhesive material that serves to affix the system to the skin during active ingredients delivery. Examples of suitable skin contact adhesive materials include, but are not limited to, polyethylenes, polysiloxanes, polyisobutylenes, polyacrylates, polyurethanes, and the like. The particular polymeric adhesive selected will depend on the particular active ingredients, vehicle, etc., i.e., the adhesive must be compatible with all components of the active ingredients-containing composition. Alternatively, the active ingredients-containing reservoir and skin contact adhesive are present as separate and distinct layers, with the adhesive underlying the reservoir which, in this case, may be either a polymeric matrix as described above, or it may be a liquid or hydrogel reservoir, or may take some other form.

The backing layer in these laminates, which serves as the upper surface of the device, functions as the primary structural element of the laminated structure and provides the device with much of its flexibility. The material selected for the backing material should be selected so that it is substantially impermeable to the active ingredients and to any other components of the active ingredients-containing composition, thus preventing loss of any components through the upper surface of the device. The backing layer may be either occlusive or non-occlusive, depending on whether it is desired that the skin become hydrated during active ingredients delivery. The backing is preferably made of a sheet or film of a preferably flexible elastomeric material. Examples of polymers that are suitable for the backing layer include polyethylene, polypropylene, and polyesters.

During storage and prior to use, the laminated structure includes a release liner. Immediately prior to use, this layer is removed from the device to expose the basal surface thereof, either the active ingredients reservoir or a separate contact adhesive layer, so that the system may be affixed to the skin. The release liner should be made from an active ingredients/vehicle impermeable material.

Such devices may be fabricated using conventional techniques, known in the art, for example by casting a fluid admixture of adhesive, active ingredients and vehicle onto the backing layer, followed by lamination of the release liner. Similarly, the adhesive mixture may be cast onto the release liner, followed by lamination of the backing layer. Alternatively, the active ingredients reservoir may be prepared in the absence of active ingredients or excipient, and then loaded by "soaking" in an active ingredients/vehicle mixture.

As with the topical formulations of the invention, the active ingredients composition contained within the active ingredients reservoirs of these laminated system may contain a number of components. In some cases, the active ingredients may be delivered "neat," i.e., in the absence of additional liquid. In most cases, however, the active ingredients will be dissolved, dispersed or suspended in a suitable pharmaceutically acceptable vehicle, typically a solvent or gel. Other components, which may be present, include preservatives, stabilizers, surfactants, and the like.

It should be noted that the protein of the invention, such as a high mannose lysosomal enzyme, is preferably administered to the patient in need in an effective amount. As used herein, "effective amount" means an amount necessary to achieve a selected result. For example, an effective amount of the composition of the invention may be selected for being useful for the treatment of a lysosomal storage disease.

Pharmaceutical compositions suitable for use in context of the present invention include compositions wherein the active ingredients are contained in an amount effective to achieve the intended purpose. More specifically, a therapeutically effective amount means an amount of active ingredient effective to prevent, alleviate or ameliorate symptoms of disease or prolong the survival of the subject being treated.

Determination of a therapeutically effective amount is well within the capability of those skilled in the art, especially in light of the detailed disclosure provided herein.

For any active ingredient used in the methods of the invention, the therapeutically effective amount or dose can be estimated initially from activity assays in animals. For example, a dose can be formulated in animal models to achieve a circulating concentration range that includes the $IC_{50}$ as determined by activity assays.

Toxicity and therapeutic efficacy of the active ingredients described herein can be determined by standard pharmaceutical procedures in experimental animals, e.g., by determining the $IC_{50}$ and the $LD_{50}$ (lethal dose causing death in 50% of the tested animals) for a subject active ingredient. The data obtained from these activity assays and animal studies can be used in formulating a range of dosage for use in human. For example, therapeutically effective doses suitable for treatment of genetic disorders can be determined from the experiments with animal models of these diseases.

The dosage may vary depending upon the dosage form employed and the route of administration utilized. The exact formulation, route of administration and dosage can be chosen by the individual physician in view of the patient's condition. (See e.g., Fingl, et al., 1975, in "The Pharmacological Basis of Therapeutics", Ch. 1 p. 1).

Dosage amount and interval may be adjusted individually to provide plasma levels of the active moiety which are sufficient to maintain the modulating effects, termed the minimal effective concentration (MEC). The MEC will vary for each preparation, but may optionally be estimated from whole animal data.

Dosage intervals can also be determined using the MEC value. Preparations may optionally be administered using a regimen, which maintains plasma levels above the MEC for 10-90% of the time, preferable between 30-90% and most preferably 50-90%.

Depending on the severity and responsiveness of the condition to be treated, dosing can also be a single administration of a slow release composition described hereinabove, with course of treatment lasting from several days to several weeks or until cure is effected or diminution of the disease state is achieved.

Compositions of the present invention may, if desired, be presented in a pack or dispenser device, such as an FDA approved kit, which may contain one or more unit dosage forms containing the active ingredient. The pack may, for example, comprise metal or plastic foil, such as a blister pack. The pack or dispenser device may be accompanied by instructions for administration. The pack or dispenser may also be accompanied by a notice associated with the container in a form prescribed by a governmental agency regulating the manufacture, use or sale of pharmaceuticals, which notice is reflective of approval by the agency of the form of the compositions or human or veterinary administration. Such notice, for example, may be of labeling approved by the U.S. Food and Drug Administration for prescription drugs or of an approved product insert. Compositions comprising an active ingredient of the invention formulated in a compatible pharmaceutical carrier may also be prepared, placed in an appropriate container, and labeled for treatment of an indicated condition.

As used herein, the term "modulate" includes substantially inhibiting, slowing or reversing the progression of a disease, substantially ameliorating clinical symptoms of a disease or condition, or substantially preventing the appearance of clinical symptoms of a disease or condition. A "modulator" therefore includes an agent which may modulate a disease or condition.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

REFERENCES

1. Ma, J. K. C., Drake, P. M. W., and Christou, P. (2003) *Nature reviews* 4, 794-805
2. Lerouge, P., Cabanes-Macheteau, M, Rayon, C, Fischette-Laine, A. C., Gomord, V, Faye, L. (1998) *Plant Mol Biol* 38, 31-48
3. Lee, R. E. (1982) *Prog Clin Biol Res* 95, 177-217
4. Grabowski, G. (1993) *Adv Hum Genet.* 21, 377-441
5. Grabowski, G. A., and Hopkin, R. J. (2003) *Annual Review of Genomics and Human Genetics* 4, 403-436
6. Sorge, J. W., C., Westwood, B., Beutler, E. (1985) *Proc Natl Acad Sci USA.* 82, 7289-7293
7. Berg-Fussman, A., Grace, M., Ioannou, Y., and Grabowski, G. (1993) *J. Biol. Chem.* 268, 14861-14866
8. Grace, M., Grabowski, G A. (1990) *Biochem Biophys Res Commun* 168, 771-777
9. Grace, M., Newman, K., Scheinker, V., Berg-Fussman, A., and Grabowski, G. (1994) *J. Biol. Chem.* 269, 2283-2291
10. Barton, N. W., Brady, R. O., Dambrosia, J. M., Di Bisceglie, A. M., Doppelt, S. H., Hill, S. C., Mankin, H. J., Murray, G. J., Parker, R. I., Argoff, C. E., et al. (1991) *N Engl J. Med.* 324, 1464-1470
11. Grabowski, G. A., Barton, N. W., Pastores, G., Dambrosia, J. M., Banerjee, T. K., McKee, M. A., Parker, C., Schiffmann, R., Hill, S. C., and Brady, R. O. (1995) *Ann Intern Med* 122, 33-39
12. Pastores, G. M., Sibille, A. R., Grabowski, G. A. (1993) *Blood* 82, 408-416.
13. Weinreb, N. J., Charrow, J, Andersson, H. C., Kaplan, P, Kolodny, E. H., Mistry, P, Pastores, G, Rosenbloom, B. E., Scott, C. R., Wappner, R. S., Zimran, A. (2002) *Am J Med* 113, 112-119
14. Bijsterbosch, M. K., Donker, W, van de Bilt, H, van Weely, S, van Berkel, T. J., Aerts, J M. (1996) *Eur J Biochem* 237, 344-349
15. Friedman, B., Vaddi, K., Preston, C., Mahon, E., Cataldo, J. R., and McPherson, J. M. (1999) *Blood* 93, 2807-2816
16. Furbish, F. S., Steer, C. J., Krett, N. L., Barranger, J. A. (1981) *Biochim Biophys Acta* 673, 425-434
17. Doebber, T., Wu, M., Bugianesi, R., Ponpipom, M., Furbish, F., Barranger, J., Brady, R., and Shen, T. (1982) *J. Biol. Chem.* 257, 2193-2199
18. Dwek, R. A., Butters, T. D., Platt, F. M., Zitzmann, N. (2002) *Nature reviews* 1, 65-75
19. Neuhaus, J. M., Rogers, J. C. (1998) *Plant Mol Biol* 38, 127-144
20. Vitale, A., and Galili, G. (2001) *Plant Physiol.* 125, 115-118
21. Hellens, R., Edwards, E A., Leyland, N. R., Bean, S., Mullineaux, P. M. (2000) *Plant Mol Biol* 42, 819-832
22. Wurtele, E. S., Bulka, K. (1989) Plant Sci 61, 253-262
23. den Dulk-Ras, A., Hooykaas, P. J. (1995) *Methods Mol. Biol.* 55, 63-72
24. Laemmli, U. K. (1970) *Nature reviews* 227, 680-685
25. Bradford, M. M. (1976) *Anal Biochem* 72, 248-254
26. Stahl, P. G. S. (1982) *J Cell Biol* 93, 49-56
27. Takasaki, S., Murray, G., Furbish, F., Brady, R., Barranger, J., and Kobata, A. (1984) *J. Biol. Chem.* 259, 10112-10117
28. Lerouge, P., Cabanes-Macheteau, M., Rayon, C., Fitchette-Laine, A. C., Gomord, V., and Faye, L. (1998) *Plant Mol. Biol.* 38, 31-48
29. Frigerio, L., Pastres, A., Prada, A., and Vitale, A. (2001) *Plant Cell* 13, 1109-1126
30. Frigerio, L., de Virgilio, M., Prada, A., Faoro, F., and Vitale, A. (1998) *Plant Cell* 10, 1031-1042
31. Hadlington J L, D. J. (2000) Curr Opin Plant Biol. 3, 461-468.
32. Okamoto, T., Shimada, T., Hara-Nishimura, I., Nishimura, M., and Minamikawa, T. (2003) Plant Physiol. 132, 1892-1900
33. Bardor, M., Faveeuw, C., Fitchette, A.-C., Gilbert, D., Galas, L., Trottein, F., Faye, L., and Lerouge, P. (2003) Glycobiology 13, 427-434

What is claimed is:

1. A recombinant human glucocerebrosidase protein which comprises the amino acid sequence consisting of human glucocerebrosidase linked at its C terminus to the vacuolar targeting signal peptide as set forth in SEQ ID NO: 2, and wherein said human glucocerebrosidase protein is glycosylated and comprises at least one exposed mannose, at least one fucose having an alpha (1-3) glycosidic bond and at least one xylose.

2. The recombinant human glucocerebrosidase protein of claim 1, wherein said amino acid sequence of human glucocerebrosidase is as set forth in SEQ ID NO: 8.

3. The recombinant human glucocerebrosidase protein of claim 1, wherein said human glucocerebrosidase protein is linked at its N terminus to an endoplasmic reticulum signal peptide.

4. The recombinant human glucocerebrosidase protein of claim 1 having glucocerebrosidase catalytic activity.

5. The recombinant human glucocerebrosidase protein of claim 1, wherein said glucocerebrosidase protein is an isolated protein.

6. A pharmaceutical composition comprising the recombinant human glucocerebrosidase protein of claim 1 and a pharmaceutically acceptable carrier.

* * * * *